(12) United States Patent
Dewolf, Jr. et al.

(10) Patent No.: US 6,951,729 B1
(45) Date of Patent: Oct. 4, 2005

(54) HIGH THROUGHPUT SCREENING METHOD FOR BIOLOGICAL AGENTS AFFECTING FATTY ACID BIOSYNTHESIS

(75) Inventors: Walter E Dewolf, Jr., Glenmoore, PA (US); Howard Kallender, Wayne, PA (US); John T Lonsdale, Exton, PA (US)

(73) Assignee: Affinium Pharmaceuticals, Inc., Toronto (CA)

( * ) Notice: Subject to any disclaimer, the term of this patent is extended or adjusted under 35 U.S.C. 154(b) by 411 days.

(21) Appl. No.: 10/089,019

(22) PCT Filed: Oct. 26, 2000

(86) PCT No.: PCT/US00/29451

§ 371 (c)(1),
(2), (4) Date: Mar. 25, 2002

(87) PCT Pub. No.: WO01/30988

PCT Pub. Date: May 3, 2001

Related U.S. Application Data

(60) Provisional application No. 60/161,775, filed on Oct. 27, 1999.

(51) Int. Cl.[7] .................................................. C12Q 1/48
(52) U.S. Cl. ............................................. 435/15; 435/4
(58) Field of Search ............................... 435/15, 4, 18, 435/25, 69.2

(56) References Cited

U.S. PATENT DOCUMENTS

| | | | |
|---|---|---|---|
| 5,539,132 A | 7/1996 | Royer et al. | 549/545 |
| 5,614,551 A | 3/1997 | Dick et al. | 514/454 |
| 5,759,837 A | 6/1998 | Kuhajda et al. | 435/193 |
| 5,965,402 A | 10/1999 | Black et al. | |
| 6,228,619 B1 | 5/2001 | Foster et al. | |
| 6,274,376 B1 | 8/2001 | Black et al. | |
| 6,294,357 B1 * | 9/2001 | Kallender et al. | 435/69.1 |
| 6,380,370 B1 | 4/2002 | Doucette-Stamm et al. | |
| 6,403,337 B1 | 6/2002 | Bailey et al. | |
| 6,432,670 B1 | 8/2002 | Payne et al. | |
| 6,475,751 B2 * | 11/2002 | Reynolds et al. | 435/15 |
| 6,593,114 B1 | 7/2003 | Kunsch et al. | |
| 6,613,553 B1 | 9/2003 | Rock et al. | |
| 2002/0076766 A1 | 6/2002 | Black et al. | |

FOREIGN PATENT DOCUMENTS

| | | |
|---|---|---|
| DE | 26 20 777 | 12/1977 |
| EP | 0 78 6519 A2 | 7/1997 |
| EP | 0 826 774 A2 | 4/1998 |
| JP | 10-174590 | 6/1998 |
| WO | WO 97/30070 | 8/1997 |
| WO | WO 97/30149 | 8/1997 |
| WO | WO 98/06734 | 2/1998 |
| WO | WO 98/18931 | 5/1998 |
| WO | WO 98/24475 | 6/1998 |
| WO | WO 98/26072 | 6/1998 |
| WO | WO 99/37800 * | 7/1999 |
| WO | WO 00/70017 | 11/2000 |
| WO | WO 01/48248 | 12/2000 |
| WO | WO 01/30988 | 5/2001 |
| WO | WO 01/49721 | 7/2001 |
| WO | WO 01/70995 | 9/2001 |
| WO | WO 02/31128 | 4/2002 |

OTHER PUBLICATIONS

Ward W. Kinetic and Structural Characteristics of the Inhibition of Enoyl (Acyl Carrier Protein) Reductase by Triclosan. Biochemistry 38(38)12514–12525, 1999.*
Rock, et al., "Preparative Enzymatic Synthesis and Hydrophobic Chromatography of Acyl–Acyl Carrier Protein", *The Journal of Biological Chemistry*, 254(15): 7123–7128 (1979).
Broadwater, et al., "Spinach Holo–Acyl Carrier Protein: Overproduction and Phosphopantetheinylation in *Escherichia coli* BL21 (DE3), in Vitro Acylation, and Enzymatic Desaturation of Histidine–Tagged Isoform I", Protein Expression and Purification, 15: 314–326 (1999).
Edwards, et al., "Cloning of the fabF gene in an expression vector and in vitro characterization of recombinant fabF and fabB encoded enzymes from *Escherichia coli*", FEBS Letters, 402: 62–66 (1997).
Rock, et al., "Acyl Carrier Protein from *Escherichia coli*", Methods in Enzymology, 71: 341–351 (1981).
Lambalot, et al., "Cloning, Overproduction, and Characterization of the *Escherichia coli* Holo–acyl Carrier Protein Synthase", *The Journal of Biological Chemistry*, 270(42): 24658–24661 (1995).
Bhargava et al., "Triclosan: Applications and Safety," American Journal of Infection Control, 24:209–218 (1998).
Rock et al., "Lipid Metabolism in Prokaryotes," Biochemistry of Lipids, Lipoproteins and Membranes, Elsevier Publishing Company Amsterdam, 35–74 (1996).
Rock et al., "*Escherichia coli* as a model for the regulation of dissociable (type II) fatty acid biosynthesis," Biochimica et Biophysica Acta, 1302:1–16 (1996).
Heath et al., "Mechanism of Triclosan Inhibition of Bacterial Fatty Acid Synthesis," The Journal of Biological Chemistry, 274(16):11110–11114 (1999).

(Continued)

Primary Examiner—Ralph Gitomer
(74) Attorney, Agent, or Firm—Foley Hoag, LLP

(57) ABSTRACT

Provided is a screening method for compounds affecting fatty acid biosynthesis, the method comprising: providing a reaction mixture comprising: an acyl carrier moiety or enzymes and precursors sufficient to generate the acyl carrier moiety; a bacterial enzymatic pathway comprising at least two consecutively acting enzymes selected from the group consisting of: malonyl-CoA:ACP transacylase, beta-ketoacyl-ACP synthase III, NADPH dependent beta-ketoacyl-ACP reductase, beta-hydroxylacyl-ACP dehydrase and enoyl-ACP reductase; and substrates and cofactors required for the operation of the enzymes; contacting the reaction mixture with a prospective bioactive agent; conducting a high throughput measurement of the activity of the enzymatic pathway; and determining if the contacting altered the activity of the enzymatic pathway.

17 Claims, 3 Drawing Sheets

OTHER PUBLICATIONS

Gadda et al., "Substrate Specificity of a Nitroalkane–Oxidizing Enzyme," Archives of Biochemistry and Biophysics, 363(2):309–313 (1999).

McMurray et al., "Triclosan targets lipid synthesis," Nature, 394:531–532 (1998).

Ross et al., "Molecular Cloning and Analysis of the Gene Encoding the NADH Oxidase from *Streptococcus faecalis* 10C1," Journal of Molecular Biology 227:658–671 (1992).

Bradford, Marion, "A Rapid and Sensitive Method for the Quantitation of Microgram Quantities of Protein Utilizing the Principle of Protein–Dye Binding," Analytical Biochemistry, 72:248–254 (1976).

Tchorzewski et al., "Unique primary structure of 2–nitropropane dioxygenase from *Hansenula mrakii*," European Journal of Biochemistry, 226:841–846 (1994).

Komuniecki et al., "Electron–transfer flavoprotein from anaerobic *Ascaris suum* mitochondria and its role in NADH-dependent 2–methyl branched–chain enoyl–CoA reduction," Biochimica et Biophysica Acta, 975:127–131 (1989).

Baker et al., "Enoyl–acyl–carrier–proteon reductase and *Mycobacterium tuberculosis* InhA do not conserve the Tyr–Xaa–Xaa–Xaa–Lys motif in mammalian 11β– and 17β–hydroxysteriod dehydrogenases and Drosophila alcohol dehydrogenase," Biochemical Journal, 309:1029–1030 (1995).

Gibson et al., "Contribution of NADH Oxidase to Aerobic Metabolism of *Streptococcus pyogenes*," Journal of Bacteriology, 182(2):448–455 (2000).

Boynton et al., "Cloning, Sequencing, and Expression of Clustered Genes Encoding β–Hydroxybutyryl–Coenzyme A (CoA) Dehydrogenase, Crotonase, and Butyrl–CoA Dehydrogenase from *Clostridium acetobutylicum* ATCC 824," Journal of Bacteriology, 178(11):3015–3024 (1996).

Heasley et al., "Kinetic Mechanism and Substrate Specificity of Nitroalkane Oxidase," Biochemical and Biophysical Research Communication, 225:6–10 (1996).

Havarstein et al., "An unmodified heptadecapeptide pheromone induces competence for genetic transformation in *Streptococcus pneumoniae*," Proceedings of the National Academy of Science USA, 92:11140–11144 (1995).

Deiz–Gonzalez et al., "NAD–Independent Lactate and Butyryl–CoA Dehydrogenases of Clostridium acetobutylicum P262," Current Microbiology, 34:162–166 (1997).

Slater–Radosti et al., "Biochemical and genetic characterization of the action of triclosan on *Staphylococcus aureus*," Journal of antimicrobial Chemotherapy, 48:1–6 (2001).

Heath et al., "A triclosan–resistant bacterial enzyme," Nature, 406:145–146 (2000).

Heath et al., "Broad Spectrum Antimicrobial Biocides Target the FabI Component of Fatty Acid Synthesis," The Journal of Biological Chemistry, 273(46):30316–30320 (1998).

Saito et al., "Genetic Evidence that Phosphatidylserine Synthase II Catalyzes the Conversion of Phosphatidylethanolamine to Phosphatidylserine in Chinese Hamster Ovary Cells," The Journal of Biological Chemistry, 273(27):17199–17205 (1998).

Bergler et al., "Protein EnvM is the NADH–dependent Enoyl–ACP Reductase (FabI) of *Escherichia coli*," The Journal of Biological Chemistry, 269(8):5493–5496 (1994).

Duran et al., "Characterization of cDNA Clones for the 2–Methyl Branched–chain Enoyl–CoA Reductase," The Journal of Biological Chemistry, 268(30):22391–22396 (1993).

Volkman et al., "Biosynthesis of D–Alanyl–Lipoteichoic Acid: The Teritary Structure of apo–D–Alanyl Carrier Protein," Biochemistry, 40:7964–7972 (2001).

Parkh et al., "Roles of Tyrosine 158 and Lysine 165 in the Catalytic Mechanism of InhA, the Enoyl–ACP Reductase from *Mycobacterium tuberculosis*." Biochemistry, 38:13623–13634 (1999).

Roujeinikova et al., "Crystallographic Analysis of Triclosan Bound to Enoyl Reductase," Journal of Molecular Biology, 294:527–535 (1999).

Heath et al., "Inhibition of *Staphylococcus aureus* NADPH-dependent Enoyl–Acyl Carrier Protein Reductase by Triclosan and Hexachlorophene," The Journal of Biological Chemistry, 275(7):4654–4659 (2000).

Heath et al., "Inhibition of β–Ketoacyl–Acyl Carrier Protein Synthase III (FabH) by Acyl–Acyl Carrier Protein in *Escherichia coli*," The Journal of Biological Chemistry, 271(18):10996–11000 (1996).

Heath et al., "Roles of the FabA and FabZ β–Hydroxyacyl–Acyl Carrier Protein Dehydratases in *Escherichia coli* Fatty Acid Biosynthesis," The Journal of Biological Chemistry, 271(44):27795–27801 (1996).

Heath et al., "The Enoyl–[acyl–carrier–protein] Reductases FabI and FabL from *Bacillus subtilis*," The Journal of Biological Chemistry, 275(51):40128–40133 (2000).

Heath et al., "Regulation of Fatty Acid Elongation and Initiation by Acyl–Acyl Carrier Protein in *Escherichia coli*," The Journal of Biological Chemistry, 271(4):1833–1836 (1996).

Bunzow et al., "Cloning and expression of a rat $D_2$ dopamine receptor cDNA," Nature, 336:783–787 (1988).

Whitfield et al., "Purification and Properties of Electron-transferring Flavoprotein and *Peptostreptococcus elsdenii*," The Journal of Biological Chemistry, 249(9):2801–2810 (1974).

Baldwin et al., "Electron transport in *Peptostreptococcus elsdenii*," Biochimica et Biophysica Acta, 92:421–432 (1964).

Egan et al., "Conditional mutations affecting the cell envelope of *Escherichia coli* K–12," Genetic Research, 21:139–152 (1973).

Bergler et al., "Sequences of the envM gene and of two mutated alleles in *Escherichia coli*", Journal of General Microbiology (1992), 138, pp. 2093–2100.

Broadwater et al., "Spinach Holo–Acyl Carrier Protein: Overproduction and Phosphopantetheinylation in *Escherichia coli* BL21(DE3), in Vitro Acylation, and Enzymatic Desaturation of Histidine–Tagged Isoform I1", Protein Expression and Purification 15, 314–326 (1999).

Edwards, et al., "Cloning of the fabF gene in an expression vector and in vitro characterization of recombinant fabF and fabB encoded enzymes from *Escherichia coli*", FEBS Letters, 402:62–66 (1997).

Grassberger et al., "Preparation and Antibacterial Activates of New 1,2,3–Diazaborine Derivatives and Analogues", Journal of Medicinal Chemistry, 1984, vol. 24, No. 8, pp. 947–953.

Gronowitz et al., "Antibacterial borazaro derivatives", Acta Pharm. Suecica 8, pp. 377–390 (1971).

Heath et al., "Enoyl–Acyl Carrier Protein Reductase (fabI) Plays a Determinant Role in Completing Cycles of Fatty Acid Elongation in *Escherichia coli*," The Journal of Biological Chemistry, 270(44):26538–26542 (1995).

Lam et al., "Effect of diazaborine derivative (Sa 84,474) on the virulence of *Escherichia coli*", Journal of Antimicrobial Chemotherapy (1987) 20, pp. 37–45.

Lambalot, et al., "Cloning, Over production, and Characterization of the *Escherichia coli* Holo–acyl Carrier Protein Synthase*", The Journal of Biological Chemistry, vol. 270, No. 42, pp. 24658–24661 (1995).

Ngo et al., "Computational complexity, protein structure prediction, and the Levinthal paradox", Chapter 14 in 'The Protein Folding Problem and Tertiary Structure Prediction', Merz et al. (eds.), Birkhauser, Boston, MA, pp. 433 & 492–495.

Rock et al., "Acyl Carrier Protein from *Escherichia coli*", Methods in Enzymology, 71:341–351 (1981).

Turnowsky et al., "envM genes of *Salmonella typhimurium* and *Escherichia coli*", Journal of Bacteriology, Dec. 1989 pp. 6555–6565.

Anon., "Triclosan–resistant Enzyme," (Jul. 17, 2000) Chemical & Engineering News, 78(29):39.

Revill et al., "Purification of a malonyltransferase from *Streptomyces coelicolor* A3(2) and analysis of its genetic information," Journal of Bacteriology, Jul. 1995 177(14):3947–3952, see abstract.

Cohen, J.S. et al. Oligodeoxynucleotides as antisense inhibitors of gene expression. Progress in Nucleic Acid Research and Molecular Biology. Jun. 1992, vol. 42, pp. 79–126, see entire document.

Marrakchi et al., Characterization of *Streptococcus pneumoniae* enoyl–(acyl–carrier protein) reductase (FabK), Biochem J., 370:1055–1062 (2003).

Roujeinikova et al., "Crystallographic Analysis of Triclosan Bound to Enoyl Reductase," J. Mol. Biol. 294:527–535 (1999).

Ward et al., "Kinetic and Structural Characteristics of the Inhibition of Enoyl (Acyl Carrier Protein) Reductase by Triclosan," Biochemistry 38:12514–12525 (1999).

* cited by examiner

SEQUENCE LISTING

```
<160> NUMBER OF SEQ ID NOS: 37

<210> SEQ ID NO 1
<211> LENGTH: 999
<212> TYPE: DNA
<213> ORGANISM: Staphylococcus aureus

<400> SEQUENCE: 1
atgggccatc atcatcatca tcatcatcat catcacagca gcggccatat cgaaggtcgt      60
catatgctcg agatgagtaa aacagcaatt atttttccgg gacaaggtgc ccaaaaagtt     120
ggtatggcac aagatttgtt taataacaat gatcaagcaa ctgaaatttt aacttcagca     180
gcaaagacgt tagactttga tattttagag acaatgttta ctgatgaaga aggtaaattg     240
ggtgaaactg aaaacacgca accagcttta ttgacgcata gttcggcatt attagcagcg     300
ctaaaaattt tgaatcctga ttttactatg gggcatagtt taggtgaata ttcaagttta     360
```

-continued

```
gttgcagctg acgtattatc atttgaagat gcagttaaaa ttgttagaaa acgtggtcaa    420
ttaatggcgc aagcatttcc tactggtgta ggaagcatgg ctgcagtatt gggattagat    480
tttgataaag tcgatgaaat ttgtaagtca ttatcatctg atgacaaaat aattgaacca    540
gcaaacatta attgcccagg tcaaattgtt gtttcaggtc acaaagcttt aattgatgag    600
ctagtagaaa aagtaaatc attaggtgca aacgtgtca tgcctttagc agtatctgga     660
ccattccatt catcgctaat gaaagtgatt gaagaagatt tttcaagtta cattaatcaa    720
tttgaatggc gtgatgctaa gtttcctgta gttcaaaatg taaatgcgca aggtgaaact    780
gacaaagaag taattaaatc taatatggtc aagcaattat attcaccagt acaattcatt    840
aactcaacag aatggctaat agaccaaggt gttgatcatt ttattgaaat tggtcctgga    900
aaagttttat ctggcttaat taaaaaaata aatagagatg ttaagttaac atcaattcaa    960
actttagaag atgtgaaagg atggaatgaa atgactaa                           999
```

<210> SEQ ID NO 2
<211> LENGTH: 332
<212> TYPE: PRT
<213> ORGANISM: Staphylococcus aureus

<400> SEQUENCE: 2

```
Met Gly His His His His His His His His Ser Ser Gly His
 1               5                  10                  15

Ile Glu Gly Arg His Met Leu Glu Met Ser Lys Thr Ala Ile Ile Phe
            20                  25                  30

Pro Gly Gln Gly Ala Gln Lys Val Gly Met Ala Gln Asp Leu Phe Asn
        35                  40                  45

Asn Asn Asp Gln Ala Thr Glu Ile Leu Thr Ser Ala Lys Thr Leu
    50                  55                  60

Asp Phe Asp Ile Leu Glu Thr Met Phe Thr Asp Glu Glu Gly Lys Leu
65                  70                  75                  80

Gly Glu Thr Glu Asn Thr Gln Pro Ala Leu Leu Thr His Ser Ser Ala
                85                  90                  95

Leu Leu Ala Ala Leu Lys Ile Leu Asn Pro Asp Phe Thr Met Gly His
            100                 105                 110

Ser Leu Gly Glu Tyr Ser Ser Leu Val Ala Ala Asp Val Leu Ser Phe
        115                 120                 125

Glu Asp Ala Val Lys Ile Val Arg Lys Arg Gly Gln Leu Met Ala Gln
    130                 135                 140

Ala Phe Pro Thr Gly Val Gly Ser Met Ala Ala Val Leu Gly Leu Asp
145                 150                 155                 160

Phe Asp Lys Val Asp Glu Ile Cys Lys Ser Leu Ser Ser Asp Asp Lys
                165                 170                 175

Ile Ile Glu Pro Ala Asn Ile Asn Cys Pro Gly Gln Ile Val Val Ser
            180                 185                 190

Gly His Lys Ala Leu Ile Asp Glu Leu Val Glu Lys Gly Lys Ser Leu
        195                 200                 205

Gly Ala Lys Arg Val Met Pro Leu Ala Val Ser Gly Pro Phe His Ser
    210                 215                 220

Ser Leu Met Lys Val Ile Glu Glu Asp Phe Ser Ser Tyr Ile Asn Gln
225                 230                 235                 240

Phe Glu Trp Arg Asp Ala Lys Phe Pro Val Val Gln Asn Val Asn Ala
                245                 250                 255

Gln Gly Glu Thr Asp Lys Glu Val Ile Lys Ser Asn Met Val Lys Gln
```

-continued

```
                    260                 265                 270
Leu Tyr Ser Pro Val Gln Phe Ile Asn Ser Thr Glu Trp Leu Ile Asp
        275                 280                 285
Gln Gly Val Asp His Phe Ile Glu Ile Gly Pro Gly Lys Val Leu Ser
    290                 295                 300
Gly Leu Ile Lys Lys Ile Asn Arg Asp Val Lys Leu Thr Ser Ile Gln
305                 310                 315                 320
Thr Leu Glu Asp Val Lys Gly Trp Asn Glu Asn Asp
                325                 330

<210> SEQ ID NO 3
<211> LENGTH: 312
<212> TYPE: PRT
<213> ORGANISM: Staphylococcus aureus

<400> SEQUENCE: 3

His Met Leu Glu Met Ser Lys Thr Ala Ile Ile Phe Pro Gly Gln Gly
1               5                   10                  15
Ala Gln Lys Val Gly Met Ala Gln Asp Leu Phe Asn Asn Asn Asp Gln
                20                  25                  30
Ala Thr Glu Ile Leu Thr Ser Ala Ala Lys Thr Leu Asp Phe Asp Ile
            35                  40                  45
Leu Glu Thr Met Phe Thr Asp Glu Glu Gly Lys Leu Gly Glu Thr Glu
        50                  55                  60
Asn Thr Gln Pro Ala Leu Leu Thr His Ser Ala Leu Leu Ala Ala
65                  70                  75                  80
Leu Lys Ile Leu Asn Pro Asp Phe Thr Met Gly His Ser Leu Gly Glu
                85                  90                  95
Tyr Ser Ser Leu Val Ala Ala Asp Val Leu Ser Phe Glu Asp Ala Val
                100                 105                 110
Lys Ile Val Arg Lys Arg Gly Gln Leu Met Ala Gln Ala Phe Pro Thr
            115                 120                 125
Gly Val Gly Ser Met Ala Ala Val Leu Gly Leu Asp Phe Asp Lys Val
        130                 135                 140
Asp Glu Ile Cys Lys Ser Leu Ser Ser Asp Asp Lys Ile Ile Glu Pro
145                 150                 155                 160
Ala Asn Ile Asn Cys Pro Gly Gln Ile Val Val Ser Gly His Lys Ala
                165                 170                 175
Leu Ile Asp Glu Leu Val Glu Lys Gly Lys Ser Leu Gly Ala Lys Arg
            180                 185                 190
Val Met Pro Leu Ala Val Ser Gly Pro Phe His Ser Ser Leu Met Lys
        195                 200                 205
Val Ile Glu Glu Asp Phe Ser Ser Tyr Ile Asn Gln Phe Glu Trp Arg
    210                 215                 220
Asp Ala Lys Phe Pro Val Val Gln Asn Val Asn Ala Gln Gly Glu Thr
225                 230                 235                 240
Asp Lys Glu Val Ile Lys Ser Asn Met Val Lys Gln Leu Tyr Ser Pro
                245                 250                 255
Val Gln Phe Ile Asn Ser Thr Glu Trp Leu Ile Asp Gln Gly Val Asp
                260                 265                 270
His Phe Ile Glu Ile Gly Pro Gly Lys Val Leu Ser Gly Leu Ile Lys
            275                 280                 285
Lys Ile Asn Arg Asp Val Lys Leu Thr Ser Ile Gln Thr Leu Glu Asp
        290                 295                 300
```

```
Val Lys Gly Trp Asn Glu Asn Asp
305                 310
```

```
<210> SEQ ID NO 4
<211> LENGTH: 1001
<212> TYPE: DNA
<213> ORGANISM: Staphylococcus aureus

<400> SEQUENCE: 4
```

| | | | | | |
|---|---|---|---|---|---|
| atgggcagca | gccatcatca | tcatcatcac | agcagcggcc | tggtgccgcg | cggcagccat | 60 |
| atgaacgtgg | gtattaaagg | ttttggtgca | tatgcaccag | aaaagattat | tgacaatgcc | 120 |
| tattttgagc | aatttttaga | tacatctgat | gaatggattt | ctaagatgac | tggaattaaa | 180 |
| gaaagacatt | gggcagatga | cgatcaagat | acttcagatt | tagcatatga | agcaagtgta | 240 |
| aaagcaatcg | ctgacgctgg | tattcagcct | gaagatatag | atatgataat | tgttgccaca | 300 |
| gcaactggag | atatgccatt | tccaactgtc | gcaaatatgt | tgcaagaacg | tttagggacg | 360 |
| ggcaaagttg | cctctatgga | tcaacttgca | gcatgttctg | gatttatgta | ttcaatgatt | 420 |
| acagctaaac | aatatgttca | atctggagat | tatcataata | ttttagttgt | cggtgcagat | 480 |
| aaattatcta | aataacaga | tttaactgac | cgttctactg | cagttctatt | tggagatggt | 540 |
| gcaggtgcgg | ttatcatcgg | tgaagtttca | gaaggcagag | gtattataag | ttatgaaatg | 600 |
| ggttctgatg | gcactggtgg | taaacattta | tatttagata | aagatactgg | taaactgaaa | 660 |
| atgaatggtc | gagaagtatt | taaatttgct | gttagaatta | tgggtgatgc | atcaacacgt | 720 |
| gtagttgaaa | aagcgaattt | aacatcagat | gatatagatt | tatttattcc | tcatcaagct | 780 |
| aatattagaa | ttatggaatc | agctagagaa | cgcttaggta | tttcaaaaga | caaaatgagt | 840 |
| gtttctgtaa | ataaatatgg | aaatacttca | gctgcgtcaa | tacctttaag | tatcgatcaa | 900 |
| gaattaaaaa | atggtaaact | caaagatgat | gatacaattg | ttcttgtcgg | attcggtggc | 960 |
| ggcctaactt | ggggcgcaat | gacaataaaa | tggggaaaat | a | | 1001 |

```
<210> SEQ ID NO 5
<211> LENGTH: 333
<212> TYPE: PRT
<213> ORGANISM: Staphylococcus aureus

<400> SEQUENCE: 5
```

```
Met Gly Ser Ser His His His His His Ser Ser Gly Leu Val Pro
 1               5                  10                  15

Arg Gly Ser His Met Asn Val Gly Ile Lys Gly Phe Gly Ala Tyr Ala
            20                  25                  30

Pro Glu Lys Ile Ile Asp Asn Ala Tyr Phe Glu Gln Phe Leu Asp Thr
        35                  40                  45

Ser Asp Glu Trp Ile Ser Lys Met Thr Gly Ile Lys Glu Arg His Trp
    50                  55                  60

Ala Asp Asp Gln Asp Thr Ser Asp Leu Ala Tyr Glu Ala Ser Val
65                  70                  75                  80

Lys Ala Ile Ala Asp Ala Gly Ile Gln Pro Glu Asp Ile Asp Met Ile
                85                  90                  95

Ile Val Ala Thr Ala Thr Gly Asp Met Pro Phe Pro Thr Val Ala Asn
            100                 105                 110

Met Leu Gln Glu Arg Leu Gly Thr Gly Lys Val Ala Ser Met Asp Gln
        115                 120                 125

Leu Ala Ala Cys Ser Gly Phe Met Tyr Ser Met Ile Thr Ala Lys Gln
    130                 135                 140
```

-continued

```
Tyr Val Gln Ser Gly Asp Tyr His Asn Ile Leu Val Val Gly Ala Asp
145                 150                 155                 160

Lys Leu Ser Lys Ile Thr Asp Leu Thr Asp Arg Ser Thr Ala Val Leu
            165                 170                 175

Phe Gly Asp Gly Ala Gly Ala Val Ile Ile Gly Glu Val Ser Glu Gly
            180                 185                 190

Arg Gly Ile Ile Ser Tyr Glu Met Gly Ser Asp Gly Thr Gly Gly Lys
            195                 200                 205

His Leu Tyr Leu Asp Lys Asp Thr Gly Lys Leu Lys Met Asn Gly Arg
    210                 215                 220

Glu Val Phe Lys Phe Ala Val Arg Ile Met Gly Asp Ala Ser Thr Arg
225                 230                 235                 240

Val Val Glu Lys Ala Asn Leu Thr Ser Asp Ile Asp Leu Phe Ile
            245                 250                 255

Pro His Gln Ala Asn Ile Arg Ile Met Glu Ser Ala Arg Glu Arg Leu
                260                 265                 270

Gly Ile Ser Lys Asp Lys Met Ser Val Ser Val Asn Lys Tyr Gly Asn
        275                 280                 285

Thr Ser Ala Ala Ser Ile Pro Leu Ser Ile Asp Gln Glu Leu Lys Asn
    290                 295                 300

Gly Lys Leu Lys Asp Asp Thr Ile Val Leu Val Gly Phe Gly Gly
305                 310                 315                 320

Gly Leu Thr Trp Gly Ala Met Thr Ile Lys Trp Gly Lys
            325                 330
```

<210> SEQ ID NO 6
<211> LENGTH: 315
<212> TYPE: PRT
<213> ORGANISM: Staphylococcus aureus

<400> SEQUENCE: 6

```
Gly Ser His Met Asn Val Gly Ile Lys Gly Phe Gly Ala Tyr Ala Pro
1               5                   10                  15

Glu Lys Ile Ile Asp Asn Ala Tyr Phe Glu Gln Phe Leu Asp Thr Ser
            20                  25                  30

Asp Glu Trp Ile Ser Lys Met Thr Gly Ile Lys Glu Arg His Trp Ala
        35                  40                  45

Asp Asp Asp Gln Asp Thr Ser Asp Leu Ala Glu Ala Ser Val Lys Ala
    50                  55                  60

Ile Ala Asp Ala Gly Ile Gln Pro Glu Asp Ile Asp Met Ile Ile Val
65                  70                  75                  80

Ala Thr Ala Thr Gly Asp Met Pro Phe Pro Thr Val Ala Asn Met Leu
                85                  90                  95

Gln Glu Arg Leu Gly Thr Gly Lys Val Ala Ser Met Asp Gln Leu Ala
            100                 105                 110

Ala Cys Ser Gly Phe Met Tyr Ser Met Ile Thr Ala Lys Gln Tyr Val
        115                 120                 125

Gln Ser Gly Asp Tyr His Asn Ile Leu Val Val Gly Ala Asp Lys Leu
    130                 135                 140

Ser Lys Ile Thr Asp Leu Thr Asp Arg Ser Thr Ala Val Leu Phe Gly
145                 150                 155                 160

Asp Gly Ala Gly Ala Val Ile Ile Gly Glu Val Ser Glu Gly Arg Gly
                165                 170                 175

Ile Ile Ser Tyr Glu Met Gly Ser Asp Gly Thr Gly Gly Lys His Leu
```

-continued

```
            180                 185                 190

Tyr Leu Asp Lys Asp Thr Gly Lys Leu Lys Met Asn Gly Arg Glu Val
        195                 200                 205

Phe Lys Phe Ala Val Arg Ile Met Gly Asp Ala Ser Thr Arg Val Val
    210                 215                 220

Glu Lys Ala Asn Leu Thr Ser Asp Asp Ile Asp Leu Phe Ile Pro His
225                 230                 235                 240

Gln Ala Asn Ile Arg Ile Met Glu Ser Ala Arg Glu Arg Leu Gly Ile
                245                 250                 255

Ser Lys Asp Lys Met Ser Val Ser Val Asn Lys Tyr Gly Asn Thr Ser
            260                 265                 270

Ala Ala Ser Ile Pro Leu Ser Ile Asp Gln Glu Leu Lys Asn Gly Lys
        275                 280                 285

Leu Lys Asp Asp Asp Thr Ile Val Leu Val Gly Phe Gly Gly Gly Leu
    290                 295                 300

Thr Trp Gly Ala Met Thr Ile Lys Trp Gly Lys
305                 310                 315

<210> SEQ ID NO 7
<211> LENGTH: 741
<212> TYPE: DNA
<213> ORGANISM: Staphylococcus aureus

<400> SEQUENCE: 7
atgaaaatga ctaagagtgc tttagtaaca ggtgcatcaa gaggaattgg acgtagtatt      60
gcgttacaat tagcagaaga aggatataat gtagcagtaa actatgcagg cagcaaagag     120
aaagctgaag cagtagtcga agaaatcaaa gctaaaggtg ttgacagttt tgcgattcaa     180
gcaaatgttg ccgatgctga tgaagttaaa gcaatgatta aagaagtagt tagccaattt     240
ggttctttag atgtcttagt aaataatgca ggtattactc gcgataattt attaatgcgt     300
atgaaagaac aagagtggga tgatgttatt gacacaaact taaaaggtgt atttaactgt     360
atccaaaaag caacaccaca aatgttaaga caacgtagtg gtgctatcat caatttatca     420
agtgttgttg gagcagtagg taatccggga caagcaaact atgttgcaac aaaagcaggt     480
gttattggtt taactaaatc tgcggcgcgt gaattagcat ctcgtggtat cactgtaaat     540
gcagttgcac ctggttttat tgtttctgat atgacagatg ctttaagtga tgagcttaaa     600
gaacaaatgt tgactcgaat tccgttagca cgttttggtc aagacacaga tattgctaat     660
acagtagcgt tcttagcatc agacaaagca aaatatatta caggtcaaac aatccatgta     720
aatggtggaa tgtacatgta a                                               741

<210> SEQ ID NO 8
<211> LENGTH: 246
<212> TYPE: PRT
<213> ORGANISM: Staphylococcus aureus

<400> SEQUENCE: 8

Met Lys Met Thr Lys Ser Ala Leu Val Thr Gly Ala Ser Arg Gly Ile
 1               5                  10                  15

Gly Arg Ser Ile Ala Leu Gln Leu Ala Glu Glu Gly Tyr Asn Val Ala
            20                  25                  30

Val Asn Tyr Ala Gly Ser Lys Glu Lys Ala Glu Ala Val Val Glu Glu
        35                  40                  45

Ile Lys Ala Lys Gly Val Asp Ser Phe Ala Ile Gln Ala Asn Val Ala
    50                  55                  60
```

```
Asp Ala Asp Glu Val Lys Ala Met Ile Lys Glu Val Val Ser Gln Phe
 65                  70                  75                  80

Gly Ser Leu Asp Val Leu Val Asn Asn Ala Gly Ile Thr Arg Asp Asn
                 85                  90                  95

Leu Leu Met Arg Met Lys Glu Gln Glu Trp Asp Val Ile Asp Thr
            100                 105                 110

Asn Leu Lys Gly Val Phe Asn Cys Ile Gln Lys Ala Thr Pro Gln Met
            115                 120                 125

Leu Arg Gln Arg Ser Gly Ala Ile Ile Asn Leu Ser Ser Val Val Gly
            130                 135                 140

Ala Val Gly Asn Pro Gly Gln Ala Asn Tyr Val Ala Thr Lys Ala Gly
145                 150                 155                 160

Val Ile Gly Leu Thr Lys Ser Ala Ala Arg Glu Leu Ala Ser Arg Gly
                165                 170                 175

Ile Thr Val Asn Ala Val Ala Pro Gly Phe Ile Val Ser Asp Met Thr
                180                 185                 190

Asp Ala Leu Ser Asp Glu Leu Lys Glu Gln Met Leu Thr Arg Ile Pro
            195                 200                 205

Leu Ala Arg Phe Gly Gln Asp Thr Asp Ile Ala Asn Thr Val Ala Phe
210                 215                 220

Leu Ala Ser Asp Lys Ala Lys Tyr Ile Thr Gly Gln Thr Ile His Val
225                 230                 235                 240

Asn Gly Gly Met Tyr Met
                245

<210> SEQ ID NO 9
<211> LENGTH: 501
<212> TYPE: DNA
<213> ORGANISM: Staphylococcus aureus

<400> SEQUENCE: 9
atgggcagca gccatcatca tcatcatcac agcagcggcc tggtgccgcg cggcagccat      60
atggaaacaa ttttgatta taaccaaatt aaacaaatta tacctcacag acagccattt     120
ttattaattg ataaagtagt tgaatatgaa gaaggtcaac gttgtgtggc tattaaacaa     180
gtatcaggaa acgaaccatt ctttcaaggg cattttcctg agtatgcggt aatgccaggc     240
gtattaatta ctgaagcgtt agctcaaaca ggtgcggtag ctatttttaaa tagtgaagaa     300 aataaaggta aaatcgcttt atttgctggt attgataaat gtcgttttaa acgtcaagta     360
gtacctggtg atactttaac gttggaagta gaaatcacta aaattaaagg accaatcggt     420
aaaggtaatg ctaaagctac tgtcgatggt caacttgctt gtagttgtga acttacattt     480
gcaattcaag atgtaaaata a                                               501

<210> SEQ ID NO 10
<211> LENGTH: 166
<212> TYPE: PRT
<213> ORGANISM: Staphylococcus aureus

<400> SEQUENCE: 10

Met Gly Ser Ser His His His His His His Ser Ser Gly Leu Val Pro
  1               5                  10                  15

Arg Gly Ser His Met Glu Thr Ile Phe Asp Tyr Asn Gln Ile Lys Gln
                 20                  25                  30

Ile Ile Pro His Arg Gln Pro Phe Leu Leu Ile Asp Lys Val Val Glu
            35                  40                  45
```

Tyr Glu Glu Gly Gln Arg Cys Val Ala Ile Lys Gln Val Ser Gly Asn
            50                  55                  60

Glu Pro Phe Phe Gln Gly His Phe Pro Glu Tyr Ala Val Met Pro Gly
 65                  70                  75                  80

Val Leu Ile Thr Glu Ala Leu Ala Gln Thr Gly Ala Val Ala Ile Leu
                85                  90                  95

Asn Ser Glu Glu Asn Lys Gly Lys Ile Ala Leu Phe Ala Gly Ile Asp
                100                 105                 110

Lys Cys Arg Phe Lys Arg Gln Val Val Pro Gly Asp Thr Leu Thr Leu
            115                 120                 125

Glu Val Glu Ile Thr Lys Ile Lys Gly Pro Ile Gly Lys Gly Asn Ala
130                 135                 140

Lys Ala Thr Val Asp Gly Gln Leu Ala Cys Ser Cys Glu Leu Thr Phe
145                 150                 155                 160

Ala Ile Gln Asp Val Lys
            165

<210> SEQ ID NO 11
<211> LENGTH: 774
<212> TYPE: DNA
<213> ORGANISM: Staphylococcus aureus

<400> SEQUENCE: 11
atgggcttaa atcttgaaaa caaaacatat gtcatcatgg gaatcgctaa taagcgtagt     60
attgcttttg gtgtcgctaa agttttagat caattaggtg ctaaattagt atttacttac    120
cgtaaagaac gtagccgtaa agagcttgaa aaattattag aacaattaaa tcaaccagaa    180
gcgcacttat atcaaattga tgttcaaagc gatgaagagg ttattaatgg ttttgagcaa    240
attggtaaag atgttggcaa tattgatggt gtatatcatt caatcgcatt tgctaatatg    300
gaagacttac gcggacgctt ttctgaaact tcacgtgaag gcttcttgtt agctcaagac    360
attagttctt actcattaac aattgtggct catgaagcta aaaaattaat gccagaaggt    420
ggtagcattg ttgcaacaac atatttaggt ggcgaattcg cagttcaaaa ttataatgtg    480
atgggtgttg ctaaagcgag cttagaagca atgttaaat atttagcatt agacttaggt    540
cctgataata ttcgcgttaa tgcaatttca gctggtccaa tccgtacatt aagtgcaaaa    600
ggtgtgggtg gttttcaatac aattcttaaa gaaatcgaag agcgtgcacc tttaaaacgt    660
aacgttgatc aagtagaagt aggtaaaaca gcggcttact trttaagtga cttatcaagt    720
ggcgttacag gtgaaaatat tcatgtagat agcggattcc acgcaattaa ataa          774

<210> SEQ ID NO 12
<211> LENGTH: 255
<212> TYPE: PRT
<213> ORGANISM: Staphylococcus aureus

<400> SEQUENCE: 12

Met Gly Leu Asn Leu Glu Asn Lys Thr Tyr Val Ile Met Gly Ile Ala
 1               5                   10                  15

Asn Lys Arg Ser Ile Ala Phe Gly Val Ala Lys Val Leu Asp Gln Leu
                20                  25                  30

Gly Ala Lys Leu Val Phe Thr Tyr Arg Lys Glu Arg Ser Arg Lys Glu
            35                  40                  45

Leu Glu Lys Leu Leu Glu Gln Leu Asn Gln Pro Glu Ala His Leu Tyr
 50                  55                  60

-continued

```
Gln Ile Asp Val Gln Ser Asp Glu Val Ile Asn Gly Phe Glu Gln
 65                  70                  75                  80

Ile Gly Lys Asp Val Gly Asn Ile Asp Gly Val Tyr His Ser Ile Ala
                 85                  90                  95

Phe Ala Asn Met Glu Asp Leu Arg Gly Arg Phe Ser Glu Thr Ser Arg
            100                 105                 110

Glu Gly Phe Leu Leu Ala Gln Asp Ile Ser Ser Tyr Ser Leu Thr Ile
        115                 120                 125

Val Ala His Glu Ala Lys Lys Leu Met Pro Glu Gly Gly Ser Ile Val
    130                 135                 140

Ala Thr Thr Tyr Leu Gly Gly Glu Phe Ala Val Gln Asn Tyr Asn Val
145                 150                 155                 160

Met Gly Val Ala Lys Ala Ser Leu Glu Ala Asn Val Lys Tyr Leu Ala
                165                 170                 175

Leu Asp Leu Gly Pro Asp Asn Ile Arg Val Asn Ala Ile Ser Ala Gly
            180                 185                 190

Pro Ile Arg Thr Leu Ser Ala Lys Gly Val Gly Gly Phe Asn Thr Ile
        195                 200                 205

Leu Lys Glu Ile Glu Glu Arg Ala Pro Leu Lys Arg Asn Val Asp Gln
    210                 215                 220

Val Glu Val Gly Lys Thr Ala Ala Tyr Leu Leu Ser Asp Leu Ser Ser
225                 230                 235                 240

Gly Val Thr Gly Glu Asn Ile His Val Asp Ser Gly Phe His Ala
                245                 250                 255
```

<210> SEQ ID NO 13
<211> LENGTH: 1245
<212> TYPE: DNA
<213> ORGANISM: Staphylococcus aureus

<400> SEQUENCE: 13

| | | |
|---|---|---|
| atgagtcaaa ataaaagagt agttattaca ggtatgggag ccctttctcc aatcggtaat | 60 |
| gatgtcaaaa caacatggga gaatgctcta aaaggcgtaa atggtatcga taaaattaca | 120 |
| cgtatcgata ctgaacctta tagcgttcac ttagcaggag aacttaaaaa ctttaatatt | 180 |
| gaagatcata tcgacaaaaa agaagcgcgt cgtatggata gatttactca atatgcaatt | 240 |
| gtagcagcta gagaggctgt taaagatgcg caattagata tcaatgataa tactgcagat | 300 |
| cgaatcggtg tatggattgg ttctggtatc ggtggtatgg aaacatttga aattgcacat | 360 |
| aaacaattaa tggataaagg cccaagacgt gtgagtccat ttttcgtacc aatgttaatt | 420 |
| cctgatatgg caactgggca agtatcaatt gacttaggtg caaaaggacc aaatggtgca | 480 |
| acagttacag catgtgcaac aggtacaaac tcaatcggaa agcatttaa aattgtgcaa | 540 |
| cgcggtgatg cagatgcaat gattactggt ggtacggaag ctccaatcac tcatatggca | 600 |
| attgcaggtt tcagtgcaag tcgagcgctt tctacaaatg atgacattga acagcatgt | 660 |
| cgtccattcc aagaaggtag agacggtttt gttatgggtg aaggtgctgg tattttagta | 720 |
| atcgaatctt tagaatcagc acaagctcga ggtgccaata tttatgctga gatagttggc | 780 |
| tatggtacta caggtgatgc ttatcatatt acagcgccag ctccagaagg tgaaggcggt | 840 |
| tctagagcaa tgcaagcagc tatggatgat gctggtattg aacctaaaga tgtacaatac | 900 |
| ttaaatgccc atggtacaag tactcctgtt ggtgacttaa atgaagttaa agctattaaa | 960 |
| aatacatttg gtgaagcagc taaacactta aaagttagct caacaaaatc aatgactggt | 1020 |
| cacttacttg gtgcaacagg tggaattgaa gcaatcttct cagcgctttc aattaaagac | 1080 |

```
tctaaagtcg caccgacaat acatgcggta acaccagacc cagaatgtga tttggatatt    1140
gttccaaatg aagcgcaaga ccttgatatt acttatgcaa tgagtaatag cttaggattc    1200
ggtggacata acgcagtatt agtattcaag aaatttgaag cataa                    1245
```

<210> SEQ ID NO 14
<211> LENGTH: 414
<212> TYPE: PRT
<213> ORGANISM: Staphylococcus aureus

<400> SEQUENCE: 14

```
Met Ser Gln Asn Lys Arg Val Val Ile Thr Gly Met Gly Ala Leu Ser
 1               5                  10                  15

Pro Ile Gly Asn Asp Val Lys Thr Thr Trp Glu Asn Ala Leu Lys Gly
             20                  25                  30

Val Asn Gly Ile Asp Lys Ile Thr Arg Ile Asp Thr Glu Pro Tyr Ser
         35                  40                  45

Val His Leu Ala Gly Glu Leu Lys Asn Phe Asn Ile Glu Asp His Ile
     50                  55                  60

Asp Lys Lys Glu Ala Arg Arg Met Asp Arg Phe Thr Gln Tyr Ala Ile
 65                  70                  75                  80

Val Ala Ala Arg Glu Ala Val Lys Asp Ala Gln Leu Asp Ile Asn Asp
                 85                  90                  95

Asn Thr Ala Asp Arg Ile Gly Val Trp Ile Gly Ser Gly Ile Gly Gly
            100                 105                 110

Met Glu Thr Phe Glu Ile Ala His Lys Gln Leu Met Asp Lys Gly Pro
        115                 120                 125

Arg Arg Val Ser Pro Phe Phe Val Pro Met Leu Ile Pro Asp Met Ala
    130                 135                 140

Thr Gly Gln Val Ser Ile Asp Leu Gly Ala Lys Gly Pro Asn Gly Ala
145                 150                 155                 160

Thr Val Thr Ala Cys Ala Thr Gly Thr Asn Ser Ile Gly Glu Ala Phe
                165                 170                 175

Lys Ile Val Gln Arg Gly Asp Ala Asp Ala Met Ile Thr Gly Gly Thr
            180                 185                 190

Glu Ala Pro Ile Thr His Met Ala Ile Ala Gly Phe Ser Ala Ser Arg
        195                 200                 205

Ala Leu Ser Thr Asn Asp Asp Ile Glu Thr Ala Cys Arg Pro Phe Gln
    210                 215                 220

Glu Gly Arg Asp Gly Phe Val Met Gly Glu Gly Ala Gly Ile Leu Val
225                 230                 235                 240

Ile Glu Ser Leu Glu Ser Ala Gln Ala Arg Gly Ala Asn Ile Tyr Ala
                245                 250                 255

Glu Ile Val Gly Tyr Gly Thr Thr Gly Asp Ala Tyr His Ile Thr Ala
            260                 265                 270

Pro Ala Pro Glu Gly Glu Gly Gly Ser Arg Ala Met Gln Ala Ala Met
        275                 280                 285

Asp Asp Ala Gly Ile Glu Pro Lys Asp Val Gln Tyr Leu Asn Ala His
    290                 295                 300

Gly Thr Ser Thr Pro Val Gly Asp Leu Asn Glu Val Lys Ala Ile Lys
305                 310                 315                 320

Asn Thr Phe Gly Glu Ala Ala Lys His Leu Lys Val Ser Ser Thr Lys
                325                 330                 335

Ser Met Thr Gly His Leu Leu Gly Ala Thr Gly Gly Ile Glu Ala Ile
```

-continued

```
                340                 345                 350
        Phe Ser Ala Leu Ser Ile Lys Asp Ser Lys Val Ala Pro Thr Ile His
                    355                 360                 365

Ala Val Thr Pro Asp Pro Glu Cys Asp Leu Asp Ile Val Pro Asn Glu
            370                 375                 380

Ala Gln Asp Leu Asp Ile Thr Tyr Ala Met Ser Asn Ser Leu Gly Phe
        385                 390                 395                 400

Gly Gly His Asn Ala Val Leu Val Phe Lys Lys Phe Glu Ala
                        405                 410
```

<210> SEQ ID NO 15
<211> LENGTH: 975
<212> TYPE: DNA
<213> ORGANISM: Streptococcus pneumoniae

<400> SEQUENCE: 15

| | | | | | |
|---|---|---|---|---|---|
| atggcttttg | caaaaataag | tcaggttgct | cattatgtgc | cagagcaagt | ggttacaaat | 60 |
| cacgacttgg | ctcagattat | ggataccaat | gatgagtgga | tttcaagtcg | aacgggaata | 120 |
| cgacaaaggc | atatttcaag | aacagaatct | accagtgatt | tggctacaga | ggttgctaag | 180 |
| aaactgatgg | caaaagctgg | aataacagga | aagaactgg | attttatcat | cctagctacc | 240 |
| attactccag | attcgatgat | gccctctaca | gctgctcgtg | ttcaagctaa | tattggcgct | 300 |
| aataaagcct | tgcttttga | cttaaccgcg | gcttgcagtg | gatttgtatt | tgctctttca | 360 |
| actgctgaaa | agtttatcgc | ttctggtcgc | tttcaaaaag | gcttggtgat | ggtagtgaa | 420 |
| accctctcta | aggcagtcga | ttggtcggat | cgatcaacag | ctgtgttgtt | tggagatggt | 480 |
| gctggtggtg | tcttgttaga | agctagcgag | caagagcatt | tcttagctga | gagtcttaat | 540 |
| agcgatggaa | gtcgcagcga | gtgtttaact | tatgggcatt | caggtttgca | ttctccattt | 600 |
| tcagatcaag | aaagtgcaga | ttcgtttttg | aagatggatg | gacgcacagt | ctttgatttt | 660 |
| gccattcgag | atgtagccaa | gtctatcaag | cagactattg | atgaatctcc | tatagaggtg | 720 |
| acagacttgg | attatctgct | acttcatcaa | gccaatgacc | gtattttgga | taagatggct | 780 |
| agaaaaattg | gtgttgaccg | agccaaactt | ccagccaata | tgatggaata | tggcaatacc | 840 |
| agtgcagcca | gtatcccgat | tttactttca | gagtgtgtag | aacaaggtct | catccctta | 900 |
| gatggtagcc | agactgttct | tctatcaggc | ttcggtggag | gcttgacctg | gggcacgctc | 960 |
| attcttacaa | tttag | | | | | 975 |

<210> SEQ ID NO 16
<211> LENGTH: 324
<212> TYPE: PRT
<213> ORGANISM: Streptococcus pneumoniae

<400> SEQUENCE: 16

```
        Met Ala Phe Ala Lys Ile Ser Gln Val Ala His Tyr Val Pro Glu Gln
        1               5                   10                  15

Val Val Thr Asn His Asp Leu Ala Gln Ile Met Asp Thr Asn Asp Glu
                        20                  25                  30

Trp Ile Ser Ser Arg Thr Gly Ile Arg Gln Arg His Ile Ser Arg Thr
                    35                  40                  45

Glu Ser Thr Ser Asp Leu Ala Thr Glu Val Ala Lys Lys Leu Met Ala
                50                  55                  60

Lys Ala Gly Ile Thr Gly Lys Glu Leu Asp Phe Ile Ile Leu Ala Thr
        65                  70                  75                  80
```

```
Ile Thr Pro Asp Ser Met Met Pro Ser Thr Ala Ala Arg Val Gln Ala
                85                  90                  95

Asn Ile Gly Ala Asn Lys Ala Phe Ala Phe Asp Leu Thr Ala Ala Cys
            100                 105                 110

Ser Gly Phe Val Phe Ala Leu Ser Thr Ala Glu Lys Phe Ile Ala Ser
        115                 120                 125

Gly Arg Phe Gln Lys Gly Leu Val Ile Gly Ser Glu Thr Leu Ser Lys
    130                 135                 140

Ala Val Asp Trp Ser Asp Arg Ser Thr Ala Val Leu Phe Gly Asp Gly
145                 150                 155                 160

Ala Gly Gly Val Leu Leu Glu Ala Ser Glu Gln Glu His Phe Leu Ala
                165                 170                 175

Glu Ser Leu Asn Ser Asp Gly Ser Arg Ser Glu Cys Leu Thr Tyr Gly
            180                 185                 190

His Ser Gly Leu His Ser Pro Phe Ser Asp Gln Glu Ser Ala Asp Ser
        195                 200                 205

Phe Leu Lys Met Asp Gly Arg Thr Val Phe Asp Phe Ala Ile Arg Asp
    210                 215                 220

Val Ala Lys Ser Ile Lys Gln Thr Ile Asp Glu Ser Pro Ile Glu Val
225                 230                 235                 240

Thr Asp Leu Asp Tyr Leu Leu Leu His Gln Ala Asn Asp Arg Ile Leu
                245                 250                 255

Asp Lys Met Ala Arg Lys Ile Gly Val Asp Arg Ala Lys Leu Pro Ala
            260                 265                 270

Asn Met Met Glu Tyr Gly Asn Thr Ser Ala Ala Ser Ile Pro Ile Leu
        275                 280                 285

Leu Ser Glu Cys Val Glu Gln Gly Leu Ile Pro Leu Asp Gly Ser Gln
    290                 295                 300

Thr Val Leu Leu Ser Gly Phe Gly Gly Gly Leu Thr Trp Gly Thr Leu
305                 310                 315                 320

Ile Leu Thr Ile

<210> SEQ ID NO 17
<211> LENGTH: 483
<212> TYPE: DNA
<213> ORGANISM: Streptococcus pneumoniae

<400> SEQUENCE: 17
atgggcagca gccatcatca tcatcatcac agcagcggcc tggtgccgcg cggcagccat      60
atgatcgata ttcaaggaat caaagaagct cttccccacc gttatcctat gcttctagtg     120
gaccgtgtct tggaagtgag cgaggatacc attgttgcta tcaaaaatgt gaccatcaac     180 gagccttttct ttaacggcca ctttcctcaa tacccagtta tgccaggtgt tgtgattatg    240
gaagccttgg cgcaaactgc cggtgtgttg gagttatcaa aacctgaaaa taaggaaaa      300 ctggtctttt acgctggtat ggacaaggtt aagttcaaga agcaagttgt accaggcgac     360
caattggtta tgacagcgac ttttgtaaaa cgtcgtggca ccatagctgt ggttgaagca     420
aaggctgaag tggatggcaa gcttgcagcc agtggtaccc ttactttgc aattgggaac     480 taa                                                                    483

<210> SEQ ID NO 18
<211> LENGTH: 160
<212> TYPE: PRT
<213> ORGANISM: Streptococcus pneumoniae
```

```
<400> SEQUENCE: 18

Met Gly Ser Ser His His His His His His Ser Ser Gly Leu Val Pro
1               5                   10                  15

Arg Gly Ser His Met Ile Asp Ile Gln Gly Ile Lys Glu Ala Leu Pro
            20                  25                  30

His Arg Tyr Pro Met Leu Leu Val Asp Arg Val Leu Glu Val Ser Glu
        35                  40                  45

Asp Thr Ile Val Ala Ile Lys Asn Val Thr Ile Asn Glu Pro Phe Phe
    50                  55                  60

Asn Gly His Phe Pro Gln Tyr Pro Val Met Pro Gly Val Val Ile Met
65                  70                  75                  80

Glu Ala Leu Ala Gln Thr Ala Gly Val Leu Glu Leu Ser Lys Pro Glu
                85                  90                  95

Asn Lys Gly Lys Leu Val Phe Tyr Ala Gly Met Asp Lys Val Lys Phe
            100                 105                 110

Lys Lys Gln Val Val Pro Gly Asp Gln Leu Val Met Thr Ala Thr Phe
        115                 120                 125

Val Lys Arg Arg Gly Thr Ile Ala Val Val Glu Ala Lys Ala Glu Val
    130                 135                 140

Asp Gly Lys Leu Ala Ala Ser Gly Thr Leu Thr Phe Ala Ile Gly Asn
145                 150                 155                 160

<210> SEQ ID NO 19
<211> LENGTH: 1296
<212> TYPE: DNA
<213> ORGANISM: Streptococcus pneumoniae

<400> SEQUENCE: 19
atgggcagca gccatcatca tcatcatcac agcagcggcc tggtgccgcg cggcagccat      60
atgaaactga tcgtgtagt ggtaacaggt tatggagtaa catctccaat cggaaataca     120
ccagaagaat tttgaatag tttagcaact gggaaaatcg gcattggtgg cattacaaaa     180
tttgatcata gtgactttga tgtgcataat gcggcagaaa tccaagattt tccgttcgat     240
aaatactttg taaaaaaga taccaaccgt tttgataact attctttata tgccttgtat     300
gcagcccaag aggctgtaaa tcatgccaat cttgatgtag aggctcttaa tagggatcgt     360
tttggtgtta tcgttgcatc tggtattggt ggaatcaagg aaattgaaga tcaggtactt     420
cgccttcatg aaaaaggacc caaacgtgtc aaaccaatga ctcttccaaa agctttacca     480
aatatggctt ctgggaatgt agccatgcgt tttggtgcaa acggtgtttg taaatctatc     540
aatactgcct gctcttcatc aaatgatgcg attgggatg ccttccgctc cattaagttt     600
ggtttccaag atgtgatgtt ggtgggagga acagaagctt ctatcacacc tttttgccatc    660 gctggtttcc aagccttaac agctctctct actacagagg atccaactcg tgcttcgatc     720
ccatttgata aggatcgcaa tgggtttgtt atgggtgaag gttcagggat gttggttcta     780
gaaagtcttg aacacgctga aaaacgtgga gctactatcc tggctgaagt ggttggttac     840
ggaaatactt gtgatgccta ccacatgact tctccacatc cagaaggtca gggagctatc     900
aaggccatca aactagcctt ggaagaagct gagatttctc cagagcaagt agcctatgtc     960
aatgctcacg gaacgtcaac tcctgccaat gaaaaggag aaagtggtgc tatcgtagct    1020
gttcttggta aggaagtacc tgtatcatca accaagtctt ttacaggaca tttgctgggg    1080
gctgcgggtg cagtagaagc tatcgtcacc atcgaagcta tgcgtcataa ctttgtacca    1140
atgacagctg gacaagtgaa agtatcagat tatatcgaag ctaatgtcgt ttatggacaa    1200
```

```
ggcttggaga aagaaattcc atacgctatt tcaaatactt ttggttttgg aggccacaat    1260
gcagttcttg ctttcaaacg ttgggagaat cgttaa                              1296
```

<210> SEQ ID NO 20
<211> LENGTH: 431
<212> TYPE: PRT
<213> ORGANISM: Streptococcus pneumoniae

<400> SEQUENCE: 20

```
Met Gly Ser Ser His His His His His His Ser Ser Gly Leu Val Pro
  1               5                  10                  15

Arg Gly Ser His Met Lys Leu Asn Arg Val Val Thr Gly Tyr Gly
             20                  25                  30

Val Thr Ser Pro Ile Gly Asn Thr Pro Glu Glu Phe Trp Asn Ser Leu
         35                  40                  45

Ala Thr Gly Lys Ile Gly Ile Gly Gly Ile Thr Lys Phe Asp His Ser
     50                  55                  60

Asp Phe Asp Val His Asn Ala Ala Glu Ile Gln Asp Phe Pro Phe Asp
 65                  70                  75                  80

Lys Tyr Phe Val Lys Lys Asp Thr Asn Arg Phe Asp Asn Tyr Ser Leu
                 85                  90                  95

Tyr Ala Leu Tyr Ala Ala Gln Glu Ala Val Asn His Ala Asn Leu Asp
            100                 105                 110

Val Glu Ala Leu Asn Arg Asp Arg Phe Gly Val Ile Val Ala Ser Gly
        115                 120                 125

Ile Gly Gly Ile Lys Glu Ile Glu Asp Gln Val Leu Arg Leu His Glu
    130                 135                 140

Lys Gly Pro Lys Arg Val Lys Pro Met Thr Leu Pro Lys Ala Leu Pro
145                 150                 155                 160

Asn Met Ala Ser Gly Asn Val Ala Met Arg Phe Gly Ala Asn Gly Val
                165                 170                 175

Cys Lys Ser Ile Asn Thr Ala Cys Ser Ser Asn Asp Ala Ile Gly
            180                 185                 190

Asp Ala Phe Arg Ser Ile Lys Phe Gly Phe Gln Asp Val Met Leu Val
        195                 200                 205

Gly Gly Thr Glu Ala Ser Ile Thr Pro Phe Ala Ile Ala Gly Phe Gln
    210                 215                 220

Ala Leu Thr Ala Leu Ser Thr Thr Glu Asp Pro Thr Arg Ala Ser Ile
225                 230                 235                 240

Pro Phe Asp Lys Asp Arg Asn Gly Phe Val Met Gly Glu Gly Ser Gly
                245                 250                 255

Met Leu Val Leu Glu Ser Leu Glu His Ala Glu Lys Arg Gly Ala Thr
            260                 265                 270

Ile Leu Ala Glu Val Val Gly Tyr Gly Asn Thr Cys Asp Ala Tyr His
        275                 280                 285

Met Thr Ser Pro His Pro Glu Gly Gln Gly Ala Ile Lys Ala Ile Lys
    290                 295                 300

Leu Ala Leu Glu Glu Ala Glu Ile Ser Pro Glu Gln Val Ala Tyr Val
305                 310                 315                 320

Asn Ala His Gly Thr Ser Thr Pro Ala Asn Glu Lys Gly Glu Ser Gly
                325                 330                 335

Ala Ile Val Ala Val Leu Gly Lys Glu Val Pro Val Ser Ser Thr Lys
            340                 345                 350
```

```
Ser Phe Thr Gly His Leu Leu Gly Ala Ala Gly Ala Val Glu Ala Ile
        355                 360                 365

Val Thr Ile Glu Ala Met Arg His Asn Phe Val Pro Met Thr Ala Gly
    370                 375                 380

Thr Ser Glu Val Ser Asp Tyr Ile Glu Ala Asn Val Tyr Gly Gln
385                 390                 395                 400

Gly Leu Glu Lys Glu Ile Pro Tyr Ala Ile Ser Asn Thr Phe Gly Phe
                405                 410                 415

Gly Gly His Asn Ala Val Leu Ala Phe Lys Arg Trp Glu Asn Arg
            420                 425                 430

<210> SEQ ID NO 21
<211> LENGTH: 1273
<212> TYPE: DNA
<213> ORGANISM: Escherichia coli

<400> SEQUENCE: 21
tcgcgattga acaggcagtg caggcggtgc agcgacaagt tcctcagcga attgccgctc      60
gcctggaatc tgtataccca gctggttttg agctgctgga cggtggcaaa agcggaactc    120
tgcggtagca ggacgctgcc agcgaactcg cagtttgcaa gtgacggtat ataaccgaaa    180
agtgactgag cgtacatgta tacgaagatt attggtactg gcagctatct gcccgaacaa    240
gtgcggacaa acgccgattt ggaaaaaatg gtggacacct ctgacgagtg gattgtcact    300
cgtaccggta tccgcgaacg ccacattgcc gcgccaaacg aaaccgtttc aaccatgggc    360
tttgaagcgg cgacacgcgc aattgagatg gcgggcattg agaaagacca gattggcctg    420
atcgttgtgg caacgacttc tgctacgcac gctttcccga gcgcagcttg tcagattcaa    480
agcatgttgg gcattaaagg ttgcccggca tttgacgttg cagcagcctg cgcaggtttc    540
acctatgcat taagcgtagc cgatcaaatc gtgaaatctg ggcggtgaa gtatgctctg    600 gtcgtcggtt ccgatgtact ggcgcgcacc tgcgatccaa ccgatcgtgg gactattatt    660
atttttggcg atggcgcggg cgctgcggtg ctggctgcct ctgaagagcc gggaatcatt    720
tccacccatc tgcatgccga cggtagttat ggtgaattgc tgacgctgcc aaacgccgac    780
cgcgtgaatc cagagaattc aattcatctg acgatggcgg gcaacgaagt cttcaaggtt    840
gcggtaacgg aactggcgca catcgttgat gagacgctgg cggcgaataa tcttgaccgt    900
tctcaactgg actggctggt tccgcatcag gctaacctgc gtattatcag tgcaacggcg    960
aaaaaactcg gtatgtctat ggataatgtc gtggtgacgc tggatcgcca cggtaatacc   1020
tctgcggcct ctgtcccgtg cgcgctggat gaagctgtac gcgacgggcg cattaagccg   1080
gggcagttgg ttctgcttga agcctttggc ggtggattca cctggggctc cgcgctggtt   1140
cgtttctagg ataaggatta aaacatgacg caatttgcat ttgtgttccc tggacagggt   1200
tctcaaaccg ttggaatgct ggctgatatg gcggcgagct atccaattgt cgaagaaacg   1260
tttgctgaag ctt                                                      1273

<210> SEQ ID NO 22
<211> LENGTH: 317
<212> TYPE: PRT
<213> ORGANISM: Escherichia coli

<400> SEQUENCE: 22

Met Tyr Thr Lys Ile Ile Gly Thr Gly Ser Tyr Leu Pro Glu Gln Val
1               5                   10                  15

Arg Thr Asn Ala Asp Leu Glu Lys Met Val Asp Thr Ser Asp Glu Trp
```

```
                20                  25                  30
Ile Val Thr Arg Thr Gly Ile Arg Glu Arg His Ile Ala Ala Pro Asn
         35                  40                  45

Glu Thr Val Ser Thr Met Gly Phe Glu Ala Ala Thr Arg Ala Ile Glu
 50                  55                  60

Met Ala Gly Ile Glu Lys Asp Gln Ile Gly Leu Ile Val Ala Thr
65                   70                  75                  80

Thr Ser Ala Thr His Ala Phe Pro Ser Ala Cys Gln Ile Gln Ser
             85                  90                  95

Met Leu Gly Ile Lys Gly Cys Pro Ala Phe Asp Val Ala Ala Cys
            100                 105                 110

Ala Gly Phe Thr Tyr Ala Leu Ser Val Ala Asp Gln Tyr Val Lys Ser
            115                 120                 125

Gly Ala Val Lys Tyr Ala Leu Val Val Gly Ser Asp Val Leu Ala Arg
            130                 135                 140

Thr Cys Asp Pro Thr Asp Arg Gly Thr Ile Ile Ile Phe Gly Asp Gly
145                 150                 155                 160

Ala Gly Ala Ala Val Leu Ala Ala Ser Glu Glu Pro Gly Ile Ile Ser
                165                 170                 175

Thr His Leu His Ala Asp Gly Ser Tyr Gly Glu Leu Leu Thr Leu Pro
                180                 185                 190

Asn Ala Asp Arg Val Asn Pro Glu Asn Ser Ile His Leu Thr Met Ala
            195                 200                 205

Gly Asn Glu Val Phe Lys Val Ala Val Thr Glu Leu Ala His Ile Val
210                 215                 220

Asp Glu Thr Leu Ala Ala Asn Asn Leu Asp Arg Ser Gln Leu Asp Trp
225                 230                 235                 240

Leu Val Pro His Gln Ala Asn Leu Arg Ile Ile Ser Ala Thr Ala Lys
                245                 250                 255

Lys Leu Gly Met Ser Met Asp Asn Val Val Val Thr Leu Asp Arg His
                260                 265                 270

Gly Asn Thr Ser Ala Ala Ser Val Pro Cys Ala Leu Asp Glu Ala Val
            275                 280                 285

Arg Asp Gly Arg Ile Lys Pro Gly Gln Leu Val Leu Leu Glu Ala Phe
290                 295                 300

Gly Gly Gly Phe Thr Trp Gly Ser Ala Leu Val Arg Phe
305                 310                 315

<210> SEQ ID NO 23
<211> LENGTH: 789
<212> TYPE: DNA
<213> ORGANISM: Escherichia coli

<400> SEQUENCE: 23
atgggttttc tttccggtaa gcgcattctg gtaaccggtg ttgccagcaa actatccatc      60
gcctacggta tcgctcaggc gatgcaccgc gaaggagctg aactggcatt cacctaccag    120
aacgacaaac tgaaaggccg cgtagaagaa tttgccgctc aattgggttc tgacatcgtt    180
ctgcagtgcg atgttgcaga agatgccagc atcgacacca tgttcgctga actggggaaa    240
gtttggccga aatttgacgg tttcgtacac tctattggtt ttgcacctgg cgatcagctg    300
gatggtgact atgttaacgc cgttacccgt gaaggcttca aaattgccca cgacatcagc    360
tcctacagct tcgttgcaat ggcaaaagct gccgctcca tgctgaatcc gggttctgcc     420
ctgctgaccc tttcctacct tggcgctgag cgcgctatcc cgaactacaa cgttatgggt    480
```

```
ctggcaaaag cgtctctgga agcgaacgtg cgctatatgg cgaacgcgat gggtccggaa    540
ggtgtgcgtg ttaacgccat ctctgctggt ccgatccgta ctctggcggc ctccggtatc    600
aaagacttcc gcaaaatgct ggctcattgc gaagccgtta ccccgattcg ccgtaccgtt    660
actattgaag atgtgggtaa ctctgcggca ttcctgtgct ccgatctctc tgccggtatc    720
tccggtgaag tggtccacgt tgacggcggt ttcagcattg ctgcaatgaa cgaactcgaa    780
ctgaaataa                                                            789
```

<210> SEQ ID NO 24
<211> LENGTH: 262
<212> TYPE: PRT
<213> ORGANISM: Escherichia coli

<400> SEQUENCE: 24

```
Met Gly Phe Leu Ser Gly Lys Arg Ile Leu Val Thr Gly Val Ala Ser
  1               5                  10                  15

Lys Leu Ser Ile Ala Tyr Gly Ile Ala Gln Ala Met His Arg Glu Gly
                 20                  25                  30

Ala Glu Leu Ala Phe Thr Tyr Gln Asn Asp Lys Leu Lys Gly Arg Val
             35                  40                  45

Glu Glu Phe Ala Ala Gln Leu Gly Ser Asp Ile Val Leu Gln Cys Asp
         50                  55                  60

Val Ala Glu Asp Ala Ser Ile Asp Thr Met Phe Ala Glu Leu Gly Lys
 65                  70                  75                  80

Val Trp Pro Lys Phe Asp Gly Phe Val His Ser Ile Gly Phe Ala Pro
                 85                  90                  95

Gly Asp Gln Leu Asp Gly Asp Tyr Val Asn Ala Val Thr Arg Glu Gly
            100                 105                 110

Phe Lys Ile Ala His Asp Ile Ser Ser Tyr Ser Phe Val Ala Met Ala
        115                 120                 125

Lys Ala Cys Arg Ser Met Leu Asn Pro Gly Ser Ala Leu Leu Thr Leu
    130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Val Arg Val Asn Ala Ile Ser Ala Gly Pro Ile
            180                 185                 190

Arg Thr Leu Ala Ala Ser Gly Ile Lys Asp Phe Arg Lys Met Leu Ala
        195                 200                 205

His Cys Glu Ala Val Thr Pro Ile Arg Arg Thr Val Thr Ile Glu Asp
    210                 215                 220

Val Gly Asn Ser Ala Ala Phe Leu Cys Ser Asp Leu Ser Ala Gly Ile
225                 230                 235                 240

Ser Gly Glu Val Val His Val Asp Gly Gly Phe Ser Ile Ala Ala Met
                245                 250                 255

Asn Glu Leu Glu Leu Lys
            260
```

<210> SEQ ID NO 25
<211> LENGTH: 234
<212> TYPE: DNA
<213> ORGANISM: Staphylococcus aureus

<400> SEQUENCE: 25

```
atggaaaatt tcgataaagt aaagatatc atcgttgacc gtttaggtgt agacgctgat      60
aaagtaactg aagatgcatc tttcaaagat gatttaggcg ctgactcact tgatatcgct    120
gaattagtaa tggaattaga agacgagttt ggtactgaaa ttcctgatga agaagctgaa    180
aaaatcaaca ctgttggtga tgctgttaaa tttattaaca gtcttgaaaa ataa          234
```

<210> SEQ ID NO 26
<211> LENGTH: 77
<212> TYPE: PRT
<213> ORGANISM: Staphylococcus aureus

<400> SEQUENCE: 26

```
Met Glu Asn Phe Asp Lys Val Lys Asp Ile Ile Val Asp Arg Leu Gly
 1               5                  10                  15

Val Asp Ala Asp Lys Val Thr Glu Asp Ala Ser Phe Lys Asp Asp Leu
            20                  25                  30

Gly Ala Asp Ser Leu Asp Ile Ala Glu Leu Val Met Glu Leu Glu Asp
        35                  40                  45

Glu Phe Gly Thr Glu Ile Pro Asp Glu Glu Ala Glu Lys Ile Asn Thr
    50                  55                  60

Val Gly Asp Ala Val Lys Phe Ile Asn Ser Leu Glu Lys
65                  70                  75
```

<210> SEQ ID NO 27
<211> LENGTH: 234
<212> TYPE: DNA
<213> ORGANISM: Streptococcus pneumoniae

<400> SEQUENCE: 27

```
atgaaagaaa agaaattttt tgacagtatt gtgaccatta tccaagagcg acagggagag    60
gactttgtcg tgacagaatc cttgagtctg aaagacgact ggatgctga ctcagttgat    120 ttgatggagt ttatcttgac gctggaggat gaatttagta tcgaaatcag cgatgaggaa    180
attgaccaac tccaaagtgt aggagatgtg gttaaaatca ttcaaggaaa atag          234
```

<210> SEQ ID NO 28
<211> LENGTH: 77
<212> TYPE: PRT
<213> ORGANISM: Streptococcus pneumoniae

<400> SEQUENCE: 28

```
Met Lys Glu Lys Glu Ile Phe Asp Ser Ile Val Thr Ile Ile Gln Glu
 1               5                  10                  15

Arg Gln Gly Glu Asp Phe Val Val Thr Glu Ser Leu Ser Leu Lys Asp
            20                  25                  30

Asp Leu Asp Ala Asp Ser Val Asp Leu Met Glu Phe Ile Leu Thr Leu
        35                  40                  45

Glu Asp Glu Phe Ser Ile Glu Ile Ser Asp Glu Glu Ile Asp Gln Leu
    50                  55                  60

Gln Ser Val Gly Asp Val Val Lys Ile Ile Gln Gly Lys
65                  70                  75
```

<210> SEQ ID NO 29
<211> LENGTH: 225
<212> TYPE: DNA
<213> ORGANISM: Streptococcus pneumoniae

<400> SEQUENCE: 29

```
atggcagtat tgaaaaagt acaagaaatt atcgttgaag aacttggaaa agacgcatca      60
gaagtaacac ttgaatcaac tttttgatgat ttggacgcag attcattgga cttgttccaa   120
gtaatctcag aaatcgaaga tgcttttgat atccaaatcg aagcagaaaa tgacttgaaa    180
acagttggtg acttggttgc ttacgttgaa gagcaagcaa aataa                    225
```

<210> SEQ ID NO 30
<211> LENGTH: 74
<212> TYPE: PRT
<213> ORGANISM: Streptococcus pnuemoniae

<400> SEQUENCE: 30

```
Met Ala Val Phe Glu Lys Val Gln Glu Ile Ile Val Glu Glu Leu Gly
  1               5                  10                  15

Lys Asp Ala Ser Glu Val Thr Leu Glu Ser Thr Phe Asp Asp Leu Asp
             20                  25                  30

Ala Asp Ser Leu Asp Leu Phe Gln Val Ile Ser Glu Ile Glu Asp Ala
         35                  40                  45

Phe Asp Ile Gln Ile Glu Ala Glu Asn Asp Leu Lys Thr Val Gly Asp
     50                  55                  60

Leu Val Ala Tyr Val Glu Glu Gln Ala Lys
 65                  70
```

<210> SEQ ID NO 31
<211> LENGTH: 951
<212> TYPE: DNA
<213> ORGANISM: Haemophilus influenzae

<400> SEQUENCE: 31

```
atgaatagta gaattttatc caccggtagc tatctgccga gccatattcg cacaaatgcg    60
gatttagaaa aaatggttga tacatcagat gaatggattg tcactcgttc tggtatccgt   120
gaacgtcgta tcgcagcgga agatgaaact gttgcaacaa tgggatttga agcggcaaaa   180
aatgcgatcg aagctgctca aattaatcct caagatattg aactgattat tgttgcaact   240
acaagtcact cacatgctta ccaagtgcgg cttgccaagt gcaaggtttt attaaatatt   300
gatgatgcga tttcttttga tttagccgca gcttgcacag gctttgtcta tgctttgagc   360
gtagctgatc aatttattcg tgcaggcaaa gtgaaaaaag ccttagtgat aggctcagat   420
ctcaattctc gtaaattaga tgaaacagat cgcagcactg ttgtgctatt tggtgatggt   480
gcgggtgctg taattttaga agcgagtgaa caagaaggaa ttatctccac ccatttacac   540
gcttcagcaa ataaaaataa tgcccttgtt ttagctcagc cagaacgtgg tatagaaaaa   600
tctggctata tcgagatgca aggtaacgaa acgttcaaat tggcagttcg tgaactttca   660
aatgtagtgg aggaaacact ttcagccaat aatttagata aaaagatttt agactggctt   720
gtgccacacc aagcaaattt acgtattatt acagcgacag ctaaaaaatt agaaatggat   780
atgtcgcaag tggtggtaac gttagataaa tacgctaata acagtgcagc aacagtgcct   840
gtcgctttag atgaggctgt tcgagatggc cgtattcaac gtgggcagtt actattatta   900
gaagcctttg gcggtggttg gacttggggt tcagcgttag tgagatttta g            951
```

<210> SEQ ID NO 32
<211> LENGTH: 316
<212> TYPE: PRT
<213> ORGANISM: Haemophilus influenzae

<400> SEQUENCE: 32

```
Met Asn Ser Arg Ile Leu Ser Thr Gly Ser Tyr Leu Pro Ser His Ile
1               5                   10                  15

Arg Thr Asn Ala Asp Leu Glu Lys Met Val Asp Thr Ser Asp Glu Trp
            20                  25                  30

Ile Val Thr Arg Ser Gly Ile Arg Glu Arg Ile Ala Ala Glu Asp
        35                  40                  45

Glu Thr Val Ala Thr Met Gly Phe Glu Ala Ala Lys Asn Ala Ile Glu
50                      55                  60

Ala Ala Gln Ile Asn Pro Gln Asp Ile Glu Leu Ile Val Ala Thr
65                  70                  75                  80

Thr Ser His Ser His Ala Tyr Pro Ser Ala Cys Gln Val Gln Gly
                85                  90                  95

Leu Leu Asn Ile Asp Asp Ala Ile Ser Phe Asp Leu Ala Ala Cys
                100                 105                 110

Thr Gly Phe Val Tyr Ala Leu Ser Val Ala Asp Gln Phe Ile Arg Ala
            115                 120                 125

Gly Lys Val Lys Lys Ala Leu Val Ile Gly Ser Asp Leu Asn Ser Arg
    130                 135                 140

Lys Leu Asp Glu Thr Asp Arg Ser Thr Val Val Leu Phe Gly Asp Gly
145                 150                 155                 160

Ala Gly Ala Val Ile Leu Glu Ala Ser Glu Gln Glu Gly Ile Ile Ser
                165                 170                 175

Thr His Leu His Ala Ser Ala Asn Lys Asn Asn Ala Leu Val Leu Ala
            180                 185                 190

Gln Pro Glu Arg Gly Ile Glu Lys Ser Gly Tyr Ile Glu Met Gln Gly
        195                 200                 205

Asn Glu Thr Phe Lys Leu Ala Val Arg Glu Leu Ser Asn Val Val Glu
    210                 215                 220

Glu Thr Leu Ser Ala Asn Asn Leu Asp Lys Lys Asp Leu Asp Trp Leu
225                 230                 235                 240

Val Pro His Gln Ala Asn Leu Arg Ile Ile Thr Ala Thr Ala Lys Lys
                245                 250                 255

Leu Glu Met Asp Met Ser Gln Val Val Val Thr Leu Asp Lys Tyr Ala
            260                 265                 270

Asn Asn Ser Ala Ala Thr Val Pro Val Ala Leu Asp Glu Ala Val Arg
        275                 280                 285

Asp Gly Arg Ile Gln Arg Gly Gln Leu Leu Leu Glu Ala Phe Gly
    290                 295                 300

Gly Gly Trp Thr Trp Gly Ser Ala Leu Val Arg Phe
305                 310                 315
```

<210> SEQ ID NO 33
<211> LENGTH: 233
<212> TYPE: DNA
<213> ORGANISM: Escherichia coli

<400> SEQUENCE: 33

| | | | | |
|---|---|---|---|---|
| atgagcacta | tcgaagaacg | cgttaagaaa | attatcggcg | aacagctggg cgttaagcag | 60 |
| gaagaagtta | ccaacaatgc | ttctttcgtt | gaagacctgg | cgcgggattc tcttgacacc | 120 |
| gttgagctgg | taatggctct | ggagaagagt | ttgatactga | gattccggac gaagaagctg | 180 |
| agaaaatcac | caccgttcag | gctgccattg | attacatcaa | cggccaccag gcg | 233 |

<210> SEQ ID NO 34
<211> LENGTH: 78

-continued

```
<212> TYPE: PRT
<213> ORGANISM: Escherichia coli

<400> SEQUENCE: 34

Met Ser Thr Ile Glu Glu Arg Val Lys Lys Ile Ile Gly Gln Leu
1               5                   10                  15

Gly Val Lys Gln Glu Glu Val Thr Asn Asn Ala Ser Phe Val Glu Asp
            20                  25                  30

Leu Gly Ala Asp Ser Leu Asp Thr Val Glu Leu Val Met Ala Leu Glu
        35                  40                  45

Glu Glu Phe Asp Thr Glu Ile Pro Asp Glu Ala Glu Lys Ile Thr
50                  55                  60

Thr Val Gln Ala Ala Ile Asp Tyr Ile Asn Gly His Gln Ala
65                  70                  75

<210> SEQ ID NO 35
<211> LENGTH: 29
<212> TYPE: DNA
<213> ORGANISM: Streptococcus pnuemoniae

<400> SEQUENCE: 35
aggttggagg ccatatgaaa acgcgtatt                                29

<210> SEQ ID NO 36
<211> LENGTH: 29
<212> TYPE: DNA
<213> ORGANISM: Streptococcus pneumoniae

<400> SEQUENCE: 36
ggcggatcct tagtcatttc ttacaactc                                29

<210> SEQ ID NO 37
<211> LENGTH: 324
<212> TYPE: PRT
<213> ORGANISM: Streptococcus pneumoniae

<400> SEQUENCE: 37

Met Lys Thr Arg Ile Thr Glu Leu Leu Lys Ile Asp Tyr Pro Ile Phe
1               5                   10                  15

Gln Gly Gly Met Ala Trp Val Ala Asp Gly Asp Leu Ala Gly Ala Val
            20                  25                  30

Ser Lys Ala Gly Gly Leu Gly Ile Ile Gly Gly Asn Ala Pro Lys
        35                  40                  45

Glu Val Val Lys Ala Asn Ile Asp Lys Ile Lys Ser Leu Thr Asp Lys
50                  55                  60

Pro Phe Gly Val Asn Ile Met Leu Leu Ser Pro Phe Val Glu Asp Ile
65                  70                  75                  80

Val Asp Leu Val Ile Glu Glu Gly Val Lys Val Thr Thr Gly Ala
            85                  90                  95

Gly Asn Pro Ser Lys Tyr Met Glu Arg Phe His Glu Ala Gly Ile Ile
            100                 105                 110

Val Ile Pro Val Val Pro Ser Val Ala Leu Ala Lys Arg Met Glu Lys
        115                 120                 125

Ile Gly Ala Asp Ala Val Ile Ala Glu Gly Met Glu Ala Gly Gly His
    130                 135                 140

Ile Gly Lys Leu Thr Thr Met Thr Leu Val Arg Gln Val Ala Thr Ala
145                 150                 155                 160

Ile Ser Ile Pro Val Ile Ala Ala Gly Gly Ile Ala Asp Gly Glu Gly
```

-continued

```
                165                 170                 175
Ala Ala Ala Gly Phe Met Leu Gly Ala Glu Ala Val Gln Val Gly Thr
            180                 185                 190
Arg Phe Val Val Ala Lys Glu Ser Asn Ala His Pro Asn Tyr Lys Glu
            195                 200                 205
Lys Ile Leu Lys Ala Arg Asp Ile Asp Thr Thr Ile Ser Ala Gln His
            210                 215                 220
Phe Gly His Ala Val Arg Ala Ile Lys Asn Gln Leu Thr Arg Asp Phe
225                 230                 235                 240
Glu Leu Ala Glu Lys Asp Ala Phe Lys Gln Glu Asp Pro Asp Leu Glu
            245                 250                 255
Ile Phe Glu Gln Met Gly Ala Gly Ala Leu Ala Lys Ala Val Val His
            260                 265                 270
Gly Asp Val Asp Gly Gly Ser Val Met Ala Gly Gln Ile Ala Gly Leu
            275                 280                 285
Val Ser Lys Glu Glu Thr Ala Glu Glu Ile Leu Lys Asp Leu Tyr Tyr
    290                 295                 300
Gly Ala Ala Lys Lys Ile Gln Glu Glu Ala Ser Arg Trp Ala Gly Val
305                 310                 315                 320
Val Arg Asn Asp
```

HIGH THROUGHPUT SCREENING METHOD FOR BIOLOGICAL AGENTS AFFECTING FATTY ACID BIOSYNTHESIS

The current application is a 371 filing of PCT/US00/29451 filed Oct. 26, 2000, which claims priority to U.S. provisional application 60/161,775, filed Oct. 27, 1999; both applications are hereby incorporated by reference in their entirety.

FIELD OF THE INVENTION

The present invention relates to fatty acid synthesis pathway reagents, including isolated pathway enzymes and substrates. Also provide are methods using such reagents to identify bioactive agents affecting fatty acid synthesis.

BACKGROUND OF THE INVENTION

The pathway for the biosynthesis of saturated fatty acids is very similar in prokaryotes and eukaryotes. However, the organization of the biosynthetic apparatus is very different. Vertebrates possess a type I fatty acid synthase (herein "FAS") in which all of the enzymatic activities are encoded on one multifunctional polypeptide, the mature protein being a homodimer. The acyl carrier protein (herein "ACP") is an integral part of the complex. In contrast, in most bacterial and plant FASs (type II) each of the reactions are catalyzed by distinct monofunctional enzymes and the ACP is a discrete protein. Mycobacteria are unique in that they possess both type I and II FASs. There appears to be considerable potential for selective inhibition of the bacterial systems by broad-spectrum antibacterial agents (Rock, C. & Cronan, J. 1996, *Biochimica et Biophysica Acta* 1302, 1–16; Jackowski, S. 1992. In *Emerging Targets in Antibacterial and Antifungal Chemotherapy*, Ed. J. Sutcliffe & N. Georgopapadakou, Chapman & Hall, New York; Jackowski, S. et al. (1989), *J. Biol. Chem.* 264, 7624–7629.)

In the biosynthetic cycle, malonyl-ACP is synthesized from ACP and malonyl-CoA by FabD, malonyl CoA:ACP transacylase. Then, malonyl-ACP is condensed with acetyl-CoA by FabH, acetoacetyl-ACP synthase III. The next step in the elongation cycle is ketoester reduction by β-ketoacyl-ACP reductase (herein "FabG"). Subsequent dehydration by β-hydroxyacyl-ACP dehydrase (herein either "FabA" or "FabZ," which are distinct enzymes) leads to trans-2-enoyl-ACP which is in turn converted to acyl-ACP by enoyl-ACP reductase (herein "FabI"). In subsequent rounds malonyl-ACP is condensed with the growing-chain acyl-ACP (herein "FabB" or "FabF," synthases I and IL respectively). Note that gram negative bacteria such as *E. coli* and *Haemophilus influenzae* have FabB and FabF enzymes, while at least certain gram positive bacteria, such as staphylococci and streptococci, have only one corresponding enzyme which is most homologous to FabF but functions as FabB. The further rounds of this cycle, adding two carbon atoms per cycle, eventually lead to palmitoyl-ACP whereupon the cycle is stopped largely due to feedback inhibition of FabH and I by palmitoyl-ACP (Heath, et al, (1996), *J. Biol. Chem.* 271, 1833–1836). The sequence of the *E. coli* apo-ACP has been described by Rawlings and Cronan (Rawlings, M. and Cronan, J. E., Jr. [1992] *J. Biol. Chem.* 267, 5751–5754). Moreover, the structures of the acyl-ACP's have been summarized in a review article: Prescott, D. J. and Vagelos, P. R. (1972) *Adv. Enzymol.* 36, 269–311. Briefly, all of the acyl-ACP's are variants of holo-ACP in which the phosphopanteteinyl group is conjugated with various acyl groups as defined elsewhere herein. The cycle is illustrated in FIG. 1.

Cerulenin and thiolactomycin are potent inhibitors of bacterial fatty acid biosynthesis. Extensive work with these inhibitors has proved that this biosynthetic pathway is essential for bacterial viability. No marketed antibiotics are targeted against fatty acid biosynthesis, therefore it is unlikely that novel antibiotics would be rendered inactive by known antibiotic resistance mechanisms. There is an unmet need for developing new classes of antibiotic compounds, such as those that target bacterial FAS.

Moreover, while acyl-ACP's are known, there is no method for efficiently producing such compounds. In view of their many uses, such as in assays of antibiotic screening using the FAS pathway, there is an unmet need in the art for such methods.

SUMMARY OF THE INVENTION

The present invention provides a method for the attachment of a phosphopantetheinyl prosthetic group to apo-ACP, preferably at a serine, especially at $Ser_{37}$ of *E. coli* apo-ACP.

Further method are also provided for making Apo-ACP, holo-ACP, and acetyl-ACP.

The invention still further provided a method for the conversion of malonyl-CoA to malonyl-ACP via FabD transacylase.

Another method of the invention provides the synthesis of D-3-Hydroxybutyryl-ACP from malonyl-ACP, the synthesis of crotonoyl-ACP, the syntheseis of butyryl-ACP The invention also provides a high throughput screening method for biological agents affecting fatty acid biosynthesis, the method comprising: (A) providing a reaction mixture comprising: (1) (a) an acyl carrier moiety or (b) enzymes and precursers sufficient to generate the acyl carrier moiety; (2) a bacterial enzymatic pathway comprising at least two (preferably three, four or five) consecutively acting enzymes selected from the group consisting of: (a) malonyl-CoA:ACP transacylase, (b) β-ketoacyl-ACP synthase III, (c) NADPH-dependent β-ketoacyl-ACP reductase, (d) β-hydroxyacyl-ACP dehydrase, and (e) enoyl-ACP reductase; and (3) substrates and cofactors required for the operation of the enzymes; (B) contacting the reaction mixture with a prospective bioactive agent; (C) conducting a high throughput measurement of the activity of the enzymatic pathway; and (D) determining if the contacting altered the activity of the enzymatic pathway.

The invention further provides a screening method for biological agents affecting fatty acid biosynthesis: (A) providing a reaction mixture comprising: (1) (a) an acyl carrier moiety or (b) enzymes and precursers sufficient to generate the acyl carrier moiety; (2) a bacterial enzymatic pathway comprising at least two consecutively acting enzymes selected from: (a) malonyl-CoA:ACP transacylase, (b) β-ketoacyl-ACP synthase III, (c) NADPH-dependent β-ketoacyl-ACP reductase, (d) β-hydroxyacyl-ACP dehydrase, and (e) enoyl-ACP reductase; and (3) substrates and cofactors required for the operation of the enzymes; (B) contacting the reaction mixture with a prospective bioactive agent; (C) measuring the activity of the enzymatic pathway; and (D) determining if the contacting altered the activity of the enzymatic pathway, wherein at least one of the following applies: (1) the enoyl-ACP reductase is a NADH-specific enoyl-ACP reductase; or (2) the β-ketoacyl-ACP synthase III is a β-ketoacyl-ACP synthase III derived from *E. coli*. or *H. influenzae;* or (3) NADPH is provided to the reacting step in a constant amount such that the NADH consumption by enoyl-ACP reductase (FabI) can be quantitated accurately and without interference, or an amount effective to reduce NADH consumption by more NADPH-dependent enzymes (such as NADPH-dependent β-ketoacyl-ACP reductase (fabG)); or (4) the NADPH-dependent β-ketoacyl-ACP reductase is derived from *Streptococcus, Staphylococcus* or *Pseudomonas*.

DETAILED DESCRIPTION OF THE INVENTION

Figure 1:
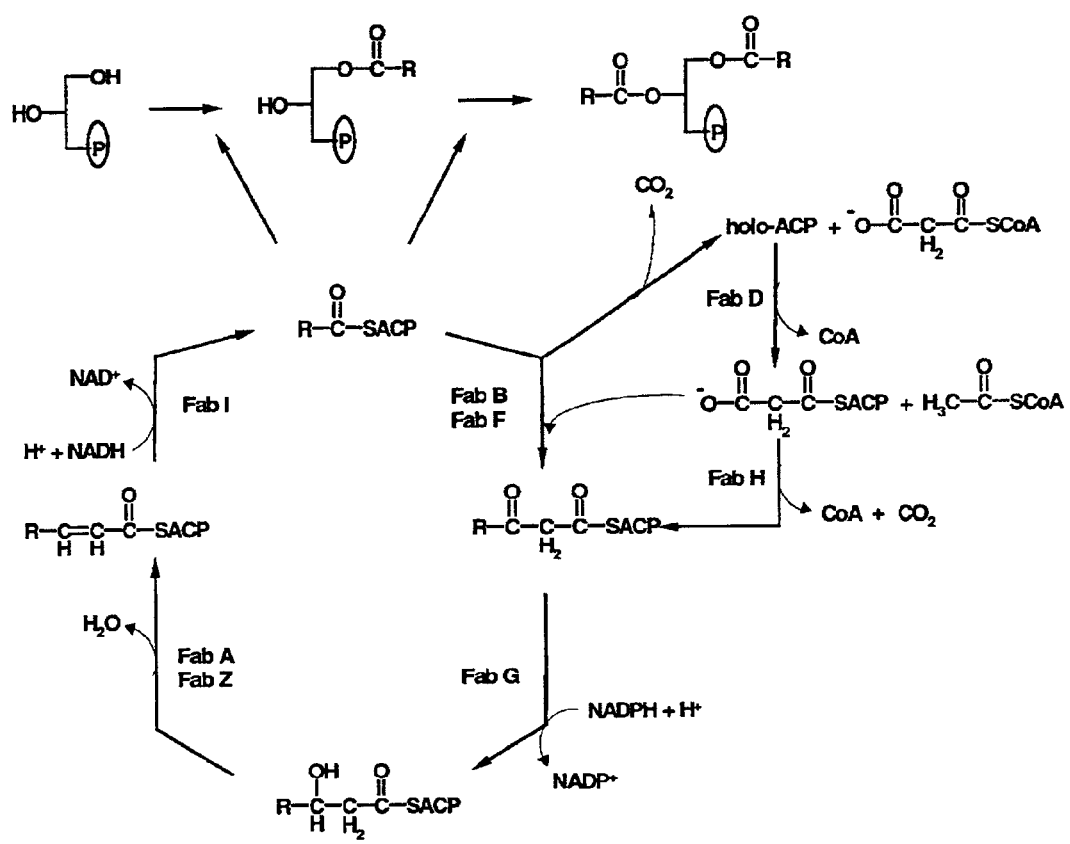
FIG. 1 illustrates the enzyme cycle of FAS, type II.

The invention provides methods for making acyl-ACP's. Apo-ACP is needed for the production of certain acyl-ACP's. In preferred methods *E. coli* apo-ACP may be used. The polynucleotide and polypeptide sequences of *E. coli* apo-ACP are shown below.

Nucleotide Sequence of *E. coli* ACP [SEQ ID NO: 33]:
ATGAGCACTATCGAAGAACGCGTTAA-
GAAAATATCGGCGAACAGCTGGGCGT-
TAAGCAGGAAGAAGT TACCAACAATGCT-
TCTTTCGTTGAAGACCTGGGCGCGGATTCTCTTG
ACACCGTTGAGCTGGTAATGG CTCTGAGAA-
GAGTTTGATACTGAGATTC-
CGGACGAAGAAGCTGAGAAAATCACCAC-
CGTTCAGGCTG CCATTGATTACATCAACGGCCAC-
CAGGCG Protein Sequence of *E. coli* ACP [SEQ ID NO: 34]:
MSTIEERVKKIIGEQLGVKQEEVTNNASDFVEDLGAD
<u>S</u>LDTVELVMALEEEFDTEIPDEEAEKITTVQAAIDYI
NGHQA A preferred method of the invention provides for the attachment of a phosphopantetheinyl prosthetic group to apo-ACP. An example of such attachment is shown in the *E. coli* apo-ACP protein, which indicates the position for the attachment of the phosphopantetheinyl prosthetic group (underlined and in bold).

Structures of acyl-ACP's are known in the art (see, for example, Prescott, D. J. and Vagelos, P. R. (1972) *Adv. Enzylmol.* 36, 269–311). These acyl-ACP's are variants of holo-ACP comprising a phosphopantetheinyl group conjugated with acyl groups. Holo-ACP is derived from apo-ACP. Apo-ACP is a preferred starting material in the methods of the invention. In another preferred embodiment, $Ser_{37}$ (underlined and in bold) is conjugated to the phosphopantetheinyl moiety of coenzyme A. The structure of holo-ACP is shown below in Table 1.

TABLE 1

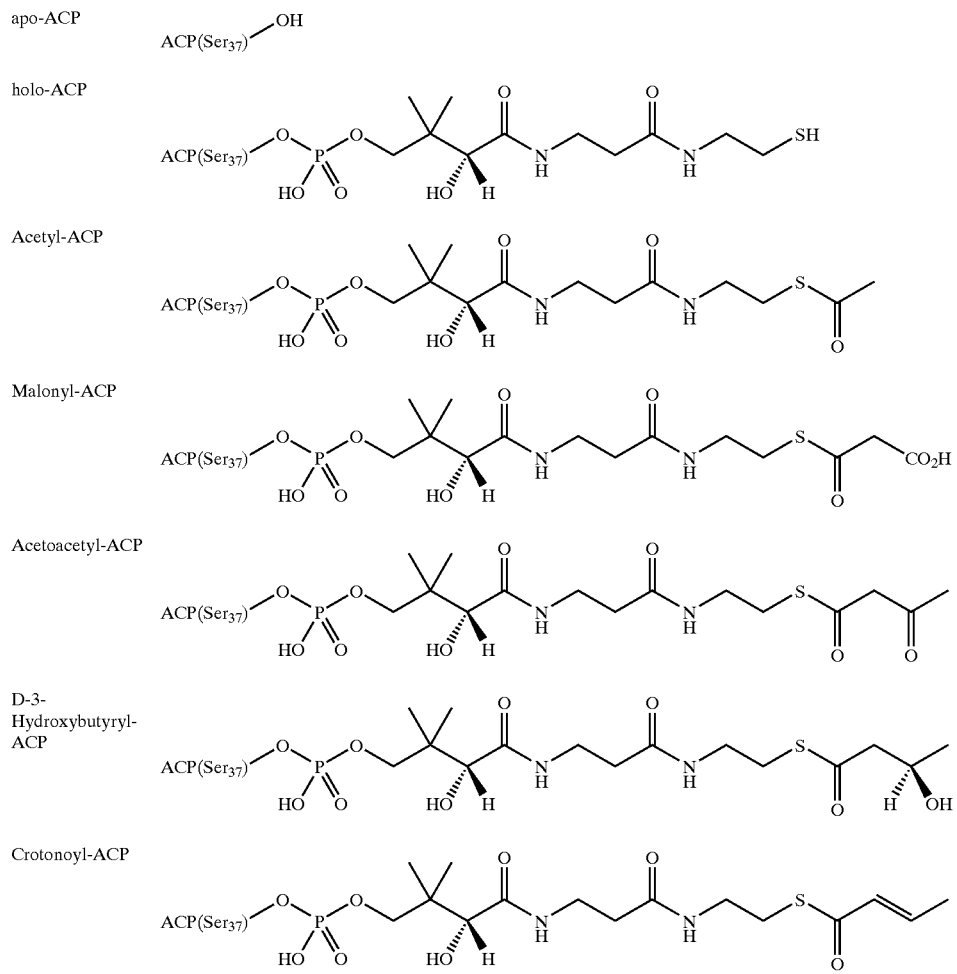

Structures of the Various Acyl-A-ACP's

TABLE 1-continued

Structures of the Various Acyl-A-ACP's

Butyryl-ACP

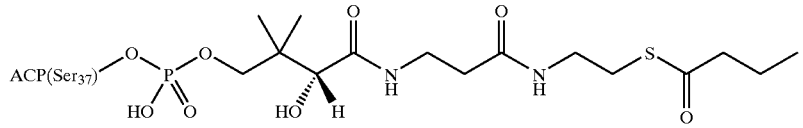

Apo-ACP may be produced as set forth herein, such as, for example, by overexpression in an *E. coli* expression system. The protein may be isolated and partially purified, followed by further purification, such as using HPLC.

Holo-ACP may be synthesized as set forth herein, such as by isolation from bacteria. Once isolated, Holo-ACP synthesis may be confirmed by FPLC, and the functionality as a substrate tested using an FabD reaction, an example of which is set forth elsewhere herein.

Acetyl-ACP may be synthesized as set forth herein. In a preferred method, acetyl-ACP is synthesized via an ACP synthase reaction, an example of which is set forth elsewhere herein. Acetyl-ACP may then be purified by FPLC, or another purification method. While acetyl-ACP is not known to be an intermediate of fatty acid biosynthesis, the invention provides that it is an inhibitor of FabH.

A reaction converting malonyl-CoA to malonyl-ACP via FabD transacylase activity is provided, whereby ACP's are separated from reducing agent, and then malonyl-ACP is concentrated using known methods.

Reaction mixtures contained buffer, malonyl-CoA, apo-ACP, and ACP synthase. In a preferred embodiment, progress of the reaction may be monitored, such as by FPLC, assess conversion of apo-ACP to malonyl-ACP.

Apo-ACP, ACP synthase and buffer are combined and incubated. Acetoacetyl-CoA is added and incubated. Formation of acetoacetyl-ACP may be monitored, such as by mass spectral analysis, or another known method, to assess reaction completion. The reaction mixture may be purified by chromatography.

D3-Hydroxybutyryl-ACP was synthesized from malonyl-ACP in a coupled enzyme system comprising buffer, malonyl-ACP, acetyl-CoA, NADPH, FabH enzyme and FabG enzyme. In a preferred method, the reaction was initiated by addition of FabH enzyme. The product of the reaction is purified as described above for apo-ACP, or as described elsewhere herein. The concentration of the D3-hydroxybutyryl-ACP may be determined by amino acid analysis or by using a functional assay consisting of FabZ coupled through FabI.

Synthesis of crotonoyl-ACP was carried out using apo-ACP in buffer, to which is added crotonoyl-CoA and ACP synthase. Reaction completion may be measured using any known method, such as by mass spectrometry. In a preferred embodiment, conversion is complete when no detectable by-products are observed. The reaction mixture may then be purified, such as by using a column. Isolated crotonoyl-ACP is obtained carried out as set forth elsewhere herein for apo-ACP.

Butyryl-ACP is synthesized in reaction mixtures comprising buffer butyryl-CoA, apo-ACP, and ACP synthase, preferably in total volumes up to 50 ML Conversion of apo-ACP to butyryl-ACP is achieved in the above reaction, and reaction progression may be measured, such as by FPLC. For example, FPLC will show disappearance of apo-ACP substrate and emergence of a new product peak. Following purification, such as by FPLC, butyryl-ACP may be quantitated, such as by measuring its absorbance, preferably at 280 nm, or in a functional assay, such as utilizing malonyl-ACP and a FabF/FabG coupled, spectrophotometric assay measuring the disappearance of NADPH, preferably at 340 nm.

A FabD enzymatic assay may be carried out as follows. Labeled malonyl-ACP formation is specifically measured using labeled malonyl-CoA and holo-ACP. The substrate labeled malonyl-CoA and labeled malonyl-ACP may be differentiated via their chemical or physical characteristics, such as by solubility in TCA. Reaction conditions typically are preferably comprise buffer, malonyl-CoA, labeled malonyl-CoA, and holo-ACP. In a preferred method, FabD enzyme is added last to start the reaction. The reaction is stopped, and the proportion of products and remaining reagents is assessed, such as by using a filter assay of TCA precipitates.

Another method provided by the invention is a coupled assay. This assay relies, in part, on the observation that a product of a malonyl-CoA:ACP transacylase reaction is free coenzyme A. This fact is exploited by coupling a FabD reaction with an excess of β-ketoglutarate dehydrogenase. Preferred reaction mixtures comprise $NAD^+$, β-ketoglutaric acid, β-ketoglutarate dehydrogenase, malonyl-CoA, holo-ACP and FabD. $NAD^+$ reduction may be followed, such as spectroscopically, preferably at 340 nm.

A preferred FabH assay of the invention follows the incorporation of labeled acetyl-CoA versus labeled acetoacetyl-ACP. In general, assay mixtures comprise either labeled acetyl-CoA and malonyl-ACP, or variable concentrations of substrate. in a preferred embodiment, reactions are initiated by the addition of FabH. Reactions are preferably terminated either by adding sample aliquots from reaction tubes comprising TCA and BSA, or by adding TCA and BSA directly into a reaction plate. Proteins in the stopped reactions are recovered by filtration, or using another known method, and the amount of the protein of interest is detected, or quantitated.

The invention further provides a FabH coupled assay. The FabH/FabG coupled assay is preferably performed in a reaction mixture comprising malonyl-ACP, acetyl-CoA, NADPH and FabG. In a preferred embodiment, the reaction mixture is then incubated at an appropriate temperature, and FabH is added to start the reaction.

A still further embodiment of the invention is a FabG screening assay. This assay is run using reaction mixtures comprising buffer, NADPH, acetoacetyl-ACP, and FabG enzyme. It is preferred that the NADPH is preincubated with the FabG prior to their addition to the assay vessel.

A FabZ/I coupled assay is also provided by the invention. This assay uses FabZ and FabI enzymes. It is preferred that the assay is performed using a reaction mixture comprising buffer, NADH, FabI and FabZ. It is preferred that a substrate, 3-OH-butyryl-ACP, is diluted in buffer and incubated at the appropriate temperature. It is further preferred that the reaction is started by adding 3-OH-butyryl-ACP to the reaction mixture.

A FabI screening assay is also provided wherein assay mixtures comprise NaADA, ADA ("ADA" is N-[2-acetamido]-2-iminodiacetic acid), crotonoyl-ACP, NADPH, and an appropriate dilution Fab I. It is preferred that inhibitors are provided at concentrations varied over the range of 0.01–10 μM. The consumption of NADPH may be monitored by following the change in absorbance, preferably at 340 nm.

A FabF screening assay is also provided using a FabG coupled system comprising NADPH, malonyl-ACP, butyryl-ACP, and FabG enzyme. Compounds are added to the above mixture, and the reaction is started, preferably by the addition of FabF enzyme. Incubations are carried out, during which time the consumption of NADPH may be monitored, preferably optically at 340 nm.

The acyl-ACP's and the FAS pathway enzymes of the invention may be obtained from any organism provided herein; however, it is preferred that they are obtained from *Escherichia coli* and/or pathogenic bacteria.

The invention also relates to polypeptides and polynucleotides of the Fab (fatty acid biosynthesis) family, hereinafter referred to as "fab", as described in greater detail below, and methods of using such polynucleotides and polypeptides in screening for agonists and antagonists. In particular, the invention relates to polypeptides and polynucleotides of a fab of an organism of the invention, preferably *streptococci, staphylococci, Escherichia coli* or *Haemophilus influenzae*, that is related by amino acid sequence homology to fab polypeptide. The invention relates especially to fab having a nucleotide and amino acid sequences set out in Table 2 as SEQ ID NO: 1, 4, 7, 9, 11, 13, 15, 17, 19, 21, 23, 25, 27, 29 or 31 and SEQ ID NO: 2, 3, 5, 6, 8, 10, 12, 14, 16, 18, 20, 22, 24, 26, 28, 30 or 32 respectively. Note that sequences recited in the Sequence Listing below as "DNA" represent an exemplification of the invention, since those of ordinary skill will recognize that such sequences can be usefully employed in polynucleotides in general, including ribopolynucleotides. Note that for the present purposes "fab" polypeptides and polynucleotides include ACP polypeptides and polynucleotides, particularly those more specifically described elsewhere herein. In another aspect, the invention encompasses each nucleic acid or protein sequence described herein, as well as the vectors and host cells described.

TABLE 2

Fab Polynucleotide and Polypeptide Sequences

*Staphylococcus aureus* WCUH29 His6-fabD polynucleotide sequence [SEQ ID NO: 1]
(999 base pairs, including stop codon).
5'-ATGGGCCATCATCATCATCATCATCATCATCATCACAGCAGCGGCCATATCGAAGGTCG
TCATATGCTCGAGATGAGTAAAACAGCAATTATTTTTCCGGGACAAGGTGCCCAAAAAGTTGGTATG
GCACAAGATTTGTTTAATAACAATGATCAAGCAACTGAAATTTTAACTTCAGCAGCAAAGACGTTAG
ACTTTGATATTTTAGAGACAATGTTTACTGATGAAGAAGGTAAATTGGGTGAAACTGAAAACACGCA
ACCAGCTTTATTGACGCATAGTTCGGCATTATTAGCAGCGCTAAAAATTTTGAATCCTGATTTTACT
ATGGGGCATAGTTTAGGTGAATATTCAAGTTTAGTTGCAGCTGACGTATTATCATTTGAAGATGCAG
TTAAAATTGTTAGAAAACGTGGTCAATTAATGGCGCAAGCATTTCCTACTGGTGTAGGAAGCATGGC
TGCAGTATTGGGATTAGATTTTGATAAAGTCGATGAAATTTGTAAGTCATTATCATCTGATGACAAA
ATAATTGAACCAGCAAACATTAATTGCCCAGGTCAAATTGTTGTTTCAGGTCACAAAGCTTTAATTG
ATGAGCTAGTAGAAAAAGGTAAATCATTAGGTGCAAAACGTGTCATGCCTTTAGCAGTATCTGGACC
ATTCCATTCATCGCTAATGAAAGTGATTGAAGAAGATTTTTCAAGTTACATTAATCAATTTGAATGG
CGTGATGCTAAGTTTCCTGTAGTTCAAAATGTAAATGCGCAAGGTGAAACTGACAAAGAAGTAATTA
AATCTAATATGGTCAAGCAATTATATTCACCAGTACAATTCATTAACTCAACAGAATGGCTAATAGA
CCAAGGTGTTGATCATTTTATTGAAATTGGTCCTGGAAAAGTTTTATCTGGCTTAATTAAAAAAATA
AATAGAGATGTTAAGTTAACATCAATTCAAACTTTAGAAGATGTGAAAGGATGGAATGAAAATGACT
AA-3'

*Staphylococcus aureus* WCUH29 His6-fabD polypeptide sequence with His tag
deduced from a polynucleotide sequence in this table [SEQ ID NO: 2] (332 amino acids).
Note that Met 25 can serve as the initiation codon, particularly if the expression vector is
engineered with an appropriate ribosome binding site.
NH$_2$-MGHHHHHHHHHHSSGHIEGRHMLEMSKTAIIFPGQGAQKVGMAQDLFNNNDQATEILT
SAAKTLDFDILETMFTDEEGKLGETENTQPALLTHSSALLAALKILNPDFTMGHSLGEYSSLVAADV
LSFEDAVKIVRKRGQLMAQAFPTGVGSMAAVLGLDFDKVDEICKSLSSDDKIIEPANINCPGQIVVS
GHKALIDELVEKGKSLGAKRVMPLAVSGPFHSSLMKVIEEDFSSYINQFEWRDAKFPVVQNVNAQGE
TDKEVIKSNMVKQLYSPVQFINSTEWLIDQGVDHFIEIGPGKVLSGLIKKINRDVKLTSIQTLEDVK
GWNEND-COOH

*Staphylococcus aureus* WCUH29 fabD polypeptide sequence without His tag
deduced from a polynucleotide sequence in this table [SEQ ID NO:3] (312 amino acids), as
obtained from SEQ ID NO:2 by proteolysis with factor Xa.
NH$_2$-HMLEMSKTAIIFPGQGAQKVGMAQDLFNNNDQATEILTSAAKTLDFDILETMFTDEEGKLG
ETENTQPALLTHSSALLAALKILNPDFTMGHSLGEYSSLVAADVLSFEDAVKIVRKRGQLMAQAFPT
GVGSMAAVLGLDFDKVDEICKSLSSDDKIIEPANINCPGQIVVSGHKALIDELVEKGKSLGAKRVMP
LAVSGPFHSSLMKVIEEDFSSYINQFEWRDAKFPVVQNVNAQGETDKEVIKSNMVKQLYSPVQFINS
TEWLIDQGVDHFIEIGPGKVLSGLIKKINRDVKLTSIQTLEDVKGWNEND-COOH

*Staphylococcus aureus* WCUH29 His6-fabH polynucleotide sequence [SEQ ID NO:4]
(1001 base pairs including stop codon).
5'-ATGGGCAGCAGCCATCATCATCATCATCACAGCAGCGGCCTGGTGCCGCGCGGCAGC
CATATGAACGTGGGTATTAAAGGTTTTGGTGCATATGCACCAGAAAAGATTATTGACAATGCCTATT
TTGAGCAATTTTTAGATACATCTGATGAATGGATTTCTAAGATGACTGGAATTAAAGAAAGACATTG
GGCAGATGACGATCAAGATACTTCAGATTTAGCATATGAAGCAAGTGTAAAAGCAATCGCTGACGCT TABLE 2-continued Fab Polynucleotide and Polypeptide Sequences GGTATTCAGCCTGAAGATATAGATATGATAATTGTTGCCACAGCAACTGGAGATATGCCATTTCCAA
CTGTCGCAAATATGTTGCAAGAACGTTTAGGGACGGGCAAAGTTGCCTCTATGGATCAACTTGCAGC
ATGTTCTGGATTTATGTATTCAATGATTACAGCTAAACAATATGTTCAATCTGGAGATTATCATAAT
ATTTTAGTTGTCGGTGCAGATAAATTATCTAAAATAACAGATTTAACTGACCGTTCTACTGCAGTTC
TATTTGGAGATGGTGCAGGTGCGGTTATCATCGGTGAAGTTTCAGAAGGCAGAGGTATTATAAGTTA
TGAAATGGGTTCTGATGGCACTGGTGGTAAACATTTATATTTAGATAAAGATACTGGTAAACTGAAA
ATGAATGGTCGAGAAGTATTTAAATTTGCTGTTAGAATTATGGGTGATGCATCAACACGTGTAGTTG
AAAAAGCGAATTTAACATCAGATGATATAGATTTATTTATTCCTCATCAAGCTAATATTAGAATTAT
GGAATCAGCTAGAGAACGCTTAGGTATTTCAAAAGACAAAATGAGTGTTTCTGTAAATAAATATGGA
AATACTTCAGCTGCGTCAATACCTTTAAGTATCGATCAAGAATTAAAAAATGGTAAACTCAAAGATG
ATGACAATTGTTCTTGTCGGATTCGGTGGCGGCCTAACTTGGGCGCAATGACAATAAAATGGGG
AAAATA-3'

Staphylococcus aureus WCUH29 His6-fabH polypeptide sequence with His tag
deduced from a polynucleotide sequence in this table [SEQ ID NO:5] (333 amino acids).
Note that Met 21 can serve as the initiation codon, particularly if the expression vector is
engineered with an appropriate ribosome binding site.
NH$_2$-MGSSHHHHHHSSGLVPRGSHMNVGIKGFGAYAPEKIIDNAYFEQFLDTSDEWISKMTGIKE
RHWADDDQDTSDLAYEASVKAIADAGIQPEDIDMIIVATATGDMPFPTVANMLQERLGTGKVASMDQ
LAACSGFMYSMITAKQYVQSGDYHNILVVGADKLSKITDLTDRSTAVLFGDGAGAVIIGEVSEGRGI
ISYEMGSDGTGGKHLYLDKDTGKLKMNGREVFKFAVRIMGDASTRVVEKANLTSDDIDLFIPHQANI
RIMESARERLGISKDKMSVSVNKYGNTSAASIPLSIDQELKNGKLKDDDTIVLVGFGGGLTWGAMTI
KWGK-COOH Staphylococcus aureus WCUH29 fabH polypeptide sequence without His tag
deduced from a polynucleotide sequence in this table [SEQ ID NO:6] (315 amino acids), as
obtained from SEQ ID NO:2 by proteolysis with thrombin.
NH$_2$-GSHMNVGIKGFGAYAPEKIIDNAYFEQFLDTSDEWISKMTGIKERHWADDDQDTSDLAEA
SVKAIADAGIQPEDIDMIIVATATGDMPFPTVANMLQERLGTGKVASMDQLAACSGFMYSMITAKQY
VQSGDYHNILVVGADKLSKITDLTDRSTAVLFGDGAGAVIIGEVSEGRGIISYEMGSDGTGGKHLYL
DKDTGKLKMNGREVFKFAVRIMGDASTRVVEKANLTSDDIDLFIPHQANIRIMESARERLGISKDKM
SVSVNKYGNTSAASIPLSIDQELKNGKLKDDDTIVLVGFGGGLTWGAMTIK
WGK-COOH Staphylococcus aureus WCUH29 fabG polynucleotide sequence [SEQ ID NO:7]
(741 base pairs including stop codon).
5'-ATGAAAATGACTAAGAGTGCTTTAGTAACAGGTGCATCAAGAGGAATTGGACGTAGTA
TTGCGTTACAATTAGCAGAAGAAGGATATAATGTAGCAGTAAACTATGCAGGCAGCAAAGAGAAAGC
TGAAGCAGTAGTCGAAGAAATCAAAGCTAAAGGTGTTGACAGTTTTGCGATTCAAGCAAATGTTGCC
GATGCTGATGAAGTTAAAGCAATGATTAAAGAAGTAGTTAGCCAATTTGGTTCTTTAGATGTCTTAG
TAAATAATGCAGGTATTACTCGCGATAATTTATTAATGCGTATGAAAGAACAAGAGTGGGATGATGT
TATTGACACAAACTTAAAAGGTGTATTTAACTGTATCCAAAAAGCAACACCACAAATGTTAAGACAA
CGTAGTGGTGCTATCATCAATTTATCAAGTGTTGTTGGAGCAGTAGGTAATCCGGGACAAGCAAACT
ATGTTGCAACAAAAGCAGGTGTTATTGGTTTAACTAAATCTGCGGCGCGTGAATTAGCATCTCGTGG
TATCACTGTAAATGCAGTTGCACCTGGTTTTATTGTTTCTGATATGACAGATGCTTTAAGTGATGAG
CTTAAAGAACAAATGTTGACTCGAATTCCGTTAGCACGTTTTGGTCAAGACACAGATATTGCTAATA
CAGTAGCGTTCTTAGCATCAGACAAAGCAAAATATATTACAGGTCAAACAATCCATGTAAATGGTGG
AATGTACATGTAA-3'

Staphylococcus aureus WCUH29 fabG polypeptide sequence deduced from a
polynucleotide sequence in this table [SEQ ID NO:8] (246 amino acids).
NH$_2$-MKMTKSALVTGASRGIGRSIALQLAEEGYNVAVNYAGSKEKAEAVVEEIKAKGVDSFAIQ
ANVADADEVKAMIKEVVSQFGSLDVLVNNAGITRDNLLMRMKEQEWDDVIDTNLKGVFNCIQKATPQ
MLRQRSGAIINLSSVVGAVGNPGQANYVATKAGVIGLTKSAARELASRGITVNAVAPGFIVSDMTDA
LSDELKEQMLTRIPLARFGQDTDIANTVAFLASDKAKYITGQTIHVNGGMYM-COOH Staphylococcus aureus WCUH29 His6-fabZ polynucleotide sequence [SEQ ID NO:9]
(501 base pairs including stop codon).
5'-ATGGGCAGCAGCCATCATCATCATCATCACAGCAGCGGCCTGGTGCCGCGCGGCAGCC
ATATGGAAACAATTTTTGATTATAACCAAATTAAACAAATTATACCTCACAGACAGCCATTTTTATT
AATTGATAAAGTAGTTGAATATGAAGAAGGTCAACGTTGTGTGGCTATTAAACAAGTATCAGGAAAC
GAACCATTCTTTCAAGGGCATTTTCCTGAGTATGCGGTAATGCCAGGCGTATTAATTACTGAAGCGT
TAGCTCAAACAGGTGCGGTAGCTATTTTAAATAGTGAAGAAAATAAAGGTAAAATCGCTTTATTTGC
TGGTATTGATAAATGTCGTTTTAAACGTCAAGTAGTACCTGGTGATACTTTAACGTTGGAAGTAGAA
ATCACTAAAATTAAAGGACCAATCGGTAAAGGTAATGCTAAAGCTACTGTCGATGGTCAACTTGCTT
GTAGTTGTGAACTTACATTTGCAATTCAAGATGTAAAATAA-3'

Staphylococcus aureus His6-fabZ polypeptide sequence deduced from a
polypeptide sequence in this table [SEQ ID NO: 10] (166 amino acids). Note that Met 21
can serve as the initiation codon, particularly if the expression vector is engineered with an
appropriate ribosome binding site.
NH$_2$-MGSSHHHHHHSSGLVPRGSHMETIFDYNQIKQIIPHRQPFLLIDKVVEYEEGQRCVAIKQVS
GNEPFFQGHFPEYAVMPGVLITEALAQTGAVAILNSEENKGKIALFAGIDKCRFKRQVVPGDTLTLE
VEITKIKGPIGKGNAKATVDGQLACSCELTFAIQDVK-COOH Staphylococcus aureus fabI polynucleotide sequence [SEQ ID NO: 11] (774 base
pairs including stop codon).

TABLE 2-continued

Fab Polynucleotide and Polypeptide Sequences

5'-ATGGGCTTAAATCTTGAAAACAAAACATATGTCATCATGGGAATCGCTAATAAGCGTA
GTATTGCTTTTGGTGTCGCTAAAGTTTTAGATCAATTAGGTGCTAAATTAGTATTTACTTACCGTAA
AGAACGTAGCCGTAAAGAGCTTGAAAAATTATTAGAACAATTAAATCAACCAGAAGCGCACTTATAT
CAAATTGATGTTCAAAGCGATGAAGAGGTTATTAATGGTTTTGAGCAAATTGGTAAAGATGTTGGCA
ATATTGATGGTGTATATCATTCAATCGCATTTGCTAATATGGAAGACTTACGCGGACGCTTTCTGA
AACTTCACGTGAAGGCTTCTTGTTAGCTCAAGACATTAGTTCTTACTCATTAACAATTGTGGCTCAT
GAAGCTAAAAAATTAATGCCAGAAGGTGGTAGCATTGTTGCAACAACATATTTAGGTGGCGAATTCG
CAGTTCAAAATTATAATGTGATGGGTGTTGCTAAAGCGAGCTTAGAAGCAAATGTTAAATATTTAGC
ATTAGACTTAGGTCCTGATAATATTCGCGTTAATGCAATTTCAGCTGGTCCAATCCGTACATTAAGT
GCAAAAGGTGTGGGTGGTTTCAATACAATTCTTAAAGAAATCGAAGAGCGTGCACCTTTAAAACGTA
ACGTTGATCAAGTAGAAGTAGGTAAAACAGCGGCTTACTTRTTAAGTGACTTATCAAGTGGCGTTAC
AGGTGAAAATATTCATGTAGATAGCGGATTCCACGCAATTAAATAA-3'

*Staphylococcus aureus* fabI polypeptide sequence deduced from a polynucleotide
sequence in this table [SEQ ID NO: 12] (257 amino acids).
NH$_2$-MGLNLENKTYVIMGIANKRSIAFGVAKVLDQLGAKLVFTYRKERSRKELEKLLEQLNQPE
AHLYQIDVQSDEEVINGFEQIGKDVGNIDGVYHSIAFANMEDLRGRFSETSREGFLLAQDISSYSLT
IVAHEAKKLMPEGGSIVATTYLGGEFAVQNYNVMGVAKASLEANVKYLALDLGPDNIRVNAISAGPI
RTLSAKGVGGFNTILKEIEERAPLKRNVDQVEVGKTAAYLLSDLSSGVTGENIHVDSGFHAIK-
COOH

*Staphylococcus aureus* fabF polynucleotide sequence [SEQ ID NO: 13] (1245 base
pairs, including stop codon).
5'-
ATGAGTCAAAATAAAAGAGTAGTTATTACAGGTATGGGAGCCCTTTCTCCAATCGGTAATGATGTCAA
AACAACATGGGAGAATGCTCTAAAAGGCGTAAATGGTATCGATAAAATTACACGTATCGATACTGAACC
TTATAGCGTTCACTTAGCAGGAGAACTTAAAAACTTTAATATTGAAGATCATATCGACAAAAAAGAAGC
GCGTCGTATGGATAGATTTACTCAATATGCAATTGTAGCAGCTAGAGAGGCTGTTAAAGATGCGCAATT
AGATATCAATGATAATACTGCAGATCGAATCGGTGTATGGATTGGTTCTGGTATCGGTGGTATGGAAAC
ATTTGAAATTGCACATAAACAATTAATGGATAAAGGCCCAAGACGTGTGAGTCCATTTTTCGTACCAAT
GTTAATTCCTGATATGGCAACTGGGCAAGTATCAATTGACTTAGGTGCAAAAGGACCAAATGGTGCAAC
AGTTACAGCATGTGCAACAGGTACAAACTCAATCGGAGAAGCATTTAAAATTGTGCAACGCGGTGATGC
AGATGCAATGATTACTGGTGGTACGGAAGCTCCAATCACTCATATGGCAATTGCAGGTTTCAGTGCAAG
TCGAGCGCTTTCTACAAATGATGACATTGAAACAGCATGTCGTCCATTCCAAGAAGGTAGAGACGGTTT
TGTTATGGGTGAAGGTGCTGGTATTTTAGTAATCGAATCTTTAGAATCAGCACAAGCTCGAGGTGCCAA
TATTTATGCTGAGATAGTTGGCTATGGTACTACAGGTGATGCTTATCATATTACAGCGCCAGCTCCAGA
AGGTGAAGGCGGTTCTAGAGCAATGCAAGCAGCTATGGATGATGCTGGTATTGAACCTAAAGATGTACA
ATACTTAAATGCCCATGGTACAAGTACTCCTGTTGGTGACTTAAATGAAGTTAAAGCTATTAAAAATAC
ATTTGGTGAAGCAGCTAAACACTTAAAAGTTAGCTCAACAAAATCAATGACTGGTCACTTACTTGGTGC
AACAGGTGGAATTGAAGCAATCTTCTCAGCGCTTTCAATTAAAGACTCTAAAGTCGCACCGACAATACA
TGCGGTAACACCAGACCCAGAATGTGATTTGGATATTGTTCCAAATGAAGCGCAAGACCTTGATATTAC
TTATGCAATGAGTAATAGCTTAGGATTCGGTGGACATAACGCAGTATTAGTATTCAAGAAATTTGAAGC
ATAA-3'

*Staphylococcus aureus* fabF polypeptide sequence deduced from a polynucleotide
sequence in this [SEQ ID NO: 14] (414 amino acids).
NH$_2$-MSQNKRVVITGMGALSPIGNDVKTTWENALKGVNGIDKITRIDTEPYSVHLAGELKNFNIEDHID
KKEARRMDRFTQYAIVAAREAVKDAQLDINDNTADRIGVWIGSGIGGMETFEIAHKQLMDKGPRRVSPF
FVPMLIPDMATGQVSIDLGAKGPNGATVTACATGTNSIGEAFKIVQRGDADAMITGGTEAPITHMAIAG
FSASRALSTNDDIETACRPFQEGRDGFVMGEGAGILVIESLESAQARGANIYAEIVGYGTTGDAYHITA
PAPEGEGGSRAMQAAMDDAGIEPKDVQYLNAHGTSTPVGDLNEVKAIKNTFGEAAKHLKVSSTKSMTGH
LLGATGGIEAIFSALSIKDSKVAPTIHAVTPDPECDLDIVPNEAQDLDITYAMSNSLGFGGHNAVLVFK
KFEA-COOH

*Streptococcus Pneumoniae* FabH polynucleotide sequence [SEQ ID NO: 15] (975
base pairs including stop codon).
5'-ATGGCTTTTGCAAAAATAAGTCAGGTTGCTCATTATGTGCCAGAGCAAGTGGTTACAAA
TCACGACTTGGCTCAGATTATGGATACCAATGATGAGTGGATTTCAAGTCGAACGGGAATACGACAA
AGGCATATTTCAAGAACAGAATCTACCAGTGATTTGGCTACAGAGGTTGCTAAGAAACTGATGGCAA
AAGCTGGAATAACAGGAAAAGAACTGGATTTTATCATCCTAGCTACCATTACTCCAGATTCGATGAT
GCCCTCTACAGCTGCTCGTGTTCAAGCTAATATTGGCGCTAATAAAGCCTTTGCTTTTGACTTAACC
GCGGCTTGCAGTGGATTTGTATTTGCTCTTTCAACTGCTGAAAAGTTTATCGCTTCTGGTCGCTTTC
AAAAAGGCTTGGTGATTGGTAGTGAAACCCTCTCTAAGGCAGTCGATTGGTCGGATCGATCAACAGC
TGTGTTTGTTTGGAGATGGTGCTGGTGGTGTCTTGTTAGAAGCTAGCGAGCAAGAGCATTTCTTAGCT
GAGAGTCTTAATAGCGATGGAAGTCGCAGCGAGTGTTTAACTTATGGGCATTCAGGTTTGCATTCTC
CATTTTCAGATCAAGAAGTGCAGATTCGTTTTTGAAGATGGATGGACGCACAGTCTTTGATTTTGC
CATTCGAGATGTAGCCAAGTCTATCAAGCAGACTATTGATGAATCTCCTATAGAGGTGACAGACTTG
GATTATCTGCTACTTCATCAAGCCAATGACCGTATTTTGGATAAGATGCCTAGAAAAATTGGTGTTG
ACCGAGCCAAACTTCCAGCCAATATGATGGAATATGGCAATACCAGTGCAGCCAGTATCCCGATTTT
ACTTTCAGAGTGTGTAGAACAAGGTCTCATCCCTTTAGATGGTAGCCAGACTGTTCTTCTATCAGGC
TTCGGTGGAGGCTTGACCTGGGGCACGCTCATTCTTACAATTTAG-3'

*Streptococcus Pneumoniae* fabH polypeptide sequence deduced from a
polynucleotide sequence in this table [SEQ ID NO: 16] (324 amino acids).
NH$_2$-MAFAKISQVAHYVPEQVVTNHDLAQIMDTNDEWISSRTGIRQRHISRTESTSDLATEVAKK
LMAKAGITGKELDFIILATITPDSMMPSTAARVQANIGANKAFAFDLTAACSGFVFALSTAEKFIAS
GRFQKGLVIGSETLSKAVDWSDRSTAVLFGDGAGGVLLEASEQEHFLAESLNSDGSRSECLTYGHSG TABLE 2-continued Fab Polynucleotide and Polypeptide Sequences LHSPFSDQESADSFLKMDGRTVFDFAIRDVAKSIKQTIDESPIEVTDLDYLLLHQANDRILDKMARK
IGVDRAKLPANMMEYGNTSAASIPILLSECVEQGLIPLDGSQTVLLSGFGGGLTWGTLILTI-COOH

*Streptococcus Pneumoniae* fabZ polynucleotide sequence, with N-terminal His6
tag [SEQ ID NO: 17] (483 base pairs including stop codon).
5'-ATGGGCAGCAGCCATCATCATCATCATCACAGCAGCGGCCTGGTGCCGCGCGGCAGCCA
TATGATCGATATTCAAGGAATCAAAGAAGCTCTTCCCCACCGTTATCCTATGCTTCTAGTGGACCGT
GTCTTGGAAGTGAGCGAGGATACCATTGTTGCTATCAAAAATGTGACCATCAACGAGCCTTTCTTTA
ACGGCCACTTTCCTCAATACCCAGTTATGCCAGGTGTTGTGATTATGGAAGCCTTGGCGCAAACTGC
CGGTGTGTTGGAGTTATCAAAACCTGAAAATAAAGGAAAACTGGTCTTTTACGCTGGTATGGACAAG
GTTAAGTTCAAGAAGCAAGTTGTACCAGGCGACCAATTGGTTATGACAGCGACTTTTGTAAAACGTC
GTGGCACCATAGCTGTGGTTGAAGCAAAGGCTGAAGTGGATGGCAAGCTTGCAGCCAGTGGTACCCT
TACTTTTGCAATTGGGAACTAA-3'

*Streptococcus Pneumoniae* 100993 H6-fabZ polypeptide sequence deduced from a
polynucleotide sequence in this table [SEQ ID NO: 18] (160 amino acids). Note that Met
21 can serve as the initiation codon, particularly if the expression vector is engineered with
an appropriate ribosome binding site.
NH$_2$-MGSSHHHHHHSSGLVPRGSHMIDIQGIKEALPHRYPMLLVDRVLEVSEDTIVAIKNVTINEP
FFNGHFPQYPVMPGVVIMEALAQTAGVLELSKPENKGKLVFYAGMDKVKFKKQVVPGDQLVMTATFV
KRRGTAIVVEAKAEVDGKLAASGTLTFAIGN-COOH

*Streptococcus Pneumoniae* fabF polynucleotide sequence with N-term His6 tag
[SEQ ID NO: 19] (1,296 base pairs including stop codon).
5'-ATGGGCAGCAGCCATCATCATCATCATCACAGCAGCGGCCTGGTGCCGCGCGGCAGCCA
TATGAAACTgAATCGtGTAGTGGTAACAGGTTATGGAGTAACATCTCCAATCGGAAATACACCAGAA
GAATTTTGGAATAGTTTAGCAACTGGGAAAATCGGCATTGGTGGCATTACAAAATTTGATCATAGTG
ACTTTGATGTGCATAATGCGGCAGAAATCCAAGATTTTCCGTTCGATAAATACTTTGTAAAAAAAGA
TACCAACCGTTTTGATAACTATTCTTTATATGCCTTGTATGCAGCCCAAGAGGCTGTAAATCATGCC
AATCTTGATGTAGAGGCTCTTAATAGGGATCGTTTTGGTGTTATCGTTGCATCTGGTATTGGTGGAA
TCAAGGAAATTGAAGATCAGGTACTTCGCCTTCATGAAAAAGGACCCAAACGTGTCAAACCAATGAC
TCTTCCAAAAGCTTTACCAAATATGGCTTCTGGGAATGTAGCCATGCGTTTTGGTGCAAACGGTGTT
TGTAAATCTATCAATACTGCCTGCTCTTCATCAAATGATGCGATTGGGGATGCCTTCCGCTCCATTA
AGTTTGGTTTCCAAGATGTGATGTTGGTGGGAGGAACAGAAGCTTCTATCACACCTTTTGCCATCGC
TGGTTTCCAAGCCTTAACAGCTCTCTACTACAGAGGATCCAACTCGTGCTTCGATCCCATTTGAT
AAGGATCGCAATGGGTTTGTTATGGGTGAAGGTTCAGGGATGTTGGTTCTAGAAAGTCTTGAACACG
CTGAAAACGTGGAGCTACTATCCTGGCTGAAGTGGTTGGTTACGGAAATACTTGTGATGCCTACCA
CATGACTTCTCCACATCCAGAAGGTCAGGGAGCTATCAAGGCCATCAAACTAGCCTTGGAAGAAGCT
GAGATTTCTCCAGAGCAAGTAGCCTATGTCAATGCTCACGGAACGTCAACTCCTGCCAATGAAAAAG
GAGAAAGTGGTGCTATCGTAGCTGTTCTTGGTAAGGAAGTACCTGTATCATCAACCAAGTCTTTTAC
AGGACATTTGCTGGGGCTGCGGGTGCAGTAGAAGCTATCGTCACCATCGAAGCTATGCGTCATAAC
TTTGTACCAATGACAGCTGGGACAAGTGAAGTATCAGATTATATCGAAGCTAATGTCGTTTATGGAC
AAGGCTTGGAGAAAGAAATTCCATACGCTATTTCAAATACTTTTGGTTTTGGAGGCCACAATGCAGT
TCTTGCTTTCAAACGTTGGGAGAATCGTTAA-3'

*Streptococcus Pneumoniae* fabF polypeptide sequence deduced from a
polynucleotide sequence in this table [SEQ ID NO: 20] (431 amino acids). Note that Met
21 can serve as the initiation codon, particularly if the expression vector is engineered with
an appropriate ribosome binding site.
NH$_2$-MGSSHHHHHHSSGLVPRGSHMKLNRVVVTGYGVTSPIGNTPEEFWNSLATGKIGIGGITKF
DHSDFDVHNAAEIQDFPFDKYFVKKDTNRFDNYSLYALYAAQEAVNHANLDVEALNRDRFGVIVASG
IGGIKEIEDQVLRLHEKGPKRVKPMTLPKALPNMASGNVAMRFGANGVCKSINTACSSSNDAIGDAF
RSIKFGFQDVMLVGGTEASITPFAIAGFQALTALSTTEDPTRASIPFDKDRNGFVMGEGSGMLVLES
LEHAEKRGATILAEVVGYGNTCDAYHMTSPHPEGQGAIKAIKLALEEAEISPEQVAYVNAHGTSTPA
NEKGESGAIVAVLGKEVPVSSTKSFTGHLLGAAGAVEAIVTIEAMRHNFVPMTAGTSEVSDYIEANV
VYGQGLEKEIPYAISNTFGFGGHNAVLAFKRWENR-COOH

*Escherichia coli* FabH ORF polynucleotide sequence [SEQ ID NO: 21]. See, Tsay
et al., J. Biol. Chem. 267:6807-6814, 1992. (1,273 base pairs, including stop codon)
5'-TCGCGATTGAACAGGCAGTGCAGGCGGTGCAGCGACAAGTTCCTCAGCGAATTGCCGC
TCGCCTGGAATCTGTATACCCAGCTGGTTTTGAGCTGCTGGACGGTGGCAAAAGCGGAACTCTGCGGT
AGCAGGACGCTGCCAGCGAACTCGCAGTTTGCAAGTGACGGTATATAACCGAAAAGTGACTGAGCGTA
CATGTATACGAAGATTATTGGTACTGGCAGCTATCTGCCCGAACAAGTGCGGACAAACGCCGATTTGG
AAAAAATGGTGGACACCTCTGACGAGTGGATTGTCACTCGTACCGCGAACGCCACATTGCC
GCGCCAAACGAAACCGTTTCAACCATGGGCTTTGAAGCGGCGACACGCGCAATTGAGATGGCGGGCAT
TGAGAAAGACCAGATTGGCCTGATCGTTGTGGCAACGACTTCTGCTACGCACGCTTTCCCGAGCGCAG
CTTGTCAGATTCAAAGCATGTTGGGCATTAAAGGTTGCCCGGCATTTGACGTTGCAGCAGCCTGCGCA
GGTTTCACCTATGCATTAAGCGTAGCCGATCAATACGTGAAATCTGGGGCGGTGAAGTATGCTCTGGT
CGTCGGTTCCGATGTACTGGCGCGCACCTGCGATCCAACCGATCGTGGGACTATTATTATTTTTGGCG
ATGGCGCGGGCGCTGCGGTGCTGGCTGCCTCTGAAGAGCCGGGAATCATTTCCACCCATCTGCATGCC
GACGGTAGTTATGGTGAATTGCTGACGCTGCCAAACGCCGACCGCGTGAATCCAGAGAATTCAATTCA
TCTGACGATGGCGGGCAACGAAGTCTTCAAGGTTGCGGTAACGGAACTGGCCGACATCGTTGATGAGA
CGCTGGCGGCGAATAATCTTGACCGTTCTCAACTGGACTGGCTGGTTCCGCATCAGGCTAACCTGCGT
ATTATCAGTGCAACGGCGAAAAAACTCGGTATGTCTATGGATAATGTCGTGGTGACGCTGGATCGCCA
CGGTAATACCTCTGCGGCCTCTGTCCCGTGCGCGCTGGATGAAGCTGTACGCGACGGGCGCATTAAGC
CGGGGCAGTTGGTTCTGCTTGAAGCCTTTGGCGGTGGATTCACCTGGGGCTCCGCGCTGGTTCGTTTC
TAGGATAAGGATTAAAACATGACGCAATTTGCATTTGTGTTCCCTGGACAGGGTTCTCAAACCGTTGG TABLE 2-continued Fab Polynucleotide and Polypeptide Sequences

AATGCTGGCTGATATGGCGGCGAGCTATCCAATTGTCGAAGAAACGTTTGCTGAAGCTT-3'

*Escherichia coli* FabH polypeptide sequence deduced from a polynucleotide sequence in this table [SEQ ID NO: 22].
NH$_2$-
MYTKIIGTGSYLPEQVRTNADLEKMVDTSDEWIVTRTGIRERHIAAPNETVSTMGFEAATRAIEMA
GIEKDQIGLIVVATTSATHAFPSAACQIQSMLGIKGCPAFDVAAACAGFTYALSVADQYVKSGAVKYA
LVVGSDVLARTCDPTDRGTIIIFGDGAGAAVLAASEEPGIISTHLHADGSYGELLTLPNADRVNPENS
IHLTMAGNEVFKVAVTELAHIVDETLAANNLDRSQLDWLVPHQANLRIISATAKKLGMSMDNVVVTLD
RHGNTSAASVPCALDEAVRDGRIKPGQLVLLEAFGGGFTWGSALVRF-COOH

*Escherichia coli* FabI ORF polynucleotide sequence [SEQ ID NO: 23] (789 base pairs including stop codon).
5'-ATGGGTTTTCTTTCCGGTAAGCGCATTCTGGTAACCGGTGTTGCCAGCAAACTATCCATC
GCCTACGGTATCGCTCAGGCGATGCACCGCGAAGGAGCTGAACTGGCATTCACCTACCAGAACGACA
AACTGAAAGGCCGCGTAGAAGAATTTGCCGCTCAATTGGGTTCTGACATCGTTCTGCAGTGCGATGT
TGCAGAAGATGCCAGCATCGACACCATGTTCGCTGAACTGGGGAAAGTTTGGCCGAAATTTGACGGT
TTCGTACACTCTATTGGTTTTGCACCTGGCGATCAGCTGGATGGTGACTATGTTAACGCCGTTACCC
GTGAAGGCTTCAAAATTGCCCACGACATCAGCTCCTACAGCTTCGTTGCAATGGCAAAAGCTTGCCG
CTCCATGCTGAATCCGGGTTCTGCCCTGCTGACCCTTTCCTACCTTGGCGCTGAGCGCGCTATCCCG
AACTACAACGTTATGGGTCTGGCAAAAGCGTCTCTGGAAGCGAACGTGCGCTATATGGCGAACGCGA
TGGGTCCGGAAGGTGTGCGTGTTAACGCCATCTCTGCTGGTCCGATCCGTACTCTGGCGGCCTCCGG
TATCAAAGACTTCCGCAAAATGCTGGCTCATTGCGAAGCCGTTACCCCGATTCGCCGTACCGTTACT
ATTGAAGATGTGGGTAACTCTGCGGCATTCCTGTGCTCCGATCTCTCTGCCGGTATCTCCGGTGAAG
TGGTCCACGTTGACGGCGGTTTCAGCATTGCTGCAATGAACGAACTGAACTGAAATAA-3'

*Escherichia coli* FabI polypeptide sequence deduced from a polynucleotide sequence in this table [SEQ ID NO: 24] (262 amino acids).
NH$_2$-MGFLSGKRILVTGVASKLSIAYGIAQAMHREGAELAFTYQNDKLKGRVEEFAAQLGSDIV
LQCDVAEDASIDTMFAELGKVWPKFDGFVHSIGFAPGDQLDGDYVNAVTREGFKIAHDISSYSFVAM
AKACRSMLNPGSALLTLSYLGAERAIPNYNVMGLAKASLEANVRYMANAMGPEGVRVNAISAGPIRT
LAASGIKDFRKMLAHCEAVTPIRRTVTIEDVGNSAAFLCSDLSAGISGEVVHVDGGFSIAAMNELEL
K-COOH

*Staphylococcus aureus* WCUH29 ACP DNA polynucleotide sequence [SEQ ID NO: 25] (234 base pairs including stop codon).
5'-
ATGGAAAATTTCGATAAAGTAAAAGATATCATCGTTGACCGTTTAGGTGTAGACGCTGATAAAGTAAC
TGAAGATGCATCTTTCAAAGATGATTTAGGCGCTGACTCACTTGATATCGCTGAATTAGTAATGGAAT
TAGAAGACGAGTTTGGTACTGAAATTCCTGATGAAGAAGCTGAAAAAATCAACACTGTTGGTGATGCT
GTTAAATTTATTAACAGTCTTGAAAAATAA-3'

*Staphylococcus aureus* WCUH29 ACP polypeptide sequence deduced from a polynucleotide sequence in this table [SEQ ID NO: 26] (262 amino acids).
NH$_2$-
MENFDKVKDIIVDRLGVDADKVTEDASFKDDLGADSLDIAELVMELEDEFGTEIPDEEAEKINTVG
DAVKFINSLEK-COOH

*Streptococcus Pneumoniae* ACP DNA polynucleotide sequence [SEQ ID NO: 27] (234 base pairs including stop codon).
5'-
ATGAAAGAAAAAGAAATTTTTGACAGTATTGTGACCATTATCCAAGAGCGACAGGGAGAGGACTTT
GTCGTGACAGAATCCTTGAGTCTGAAAGACGACTTGGATGCTGACTCAGTTGATTTGATGGAGTTTAT
CTTGACGCTGGAGGATGAATTTAGTATCGAAATCAGCGATGAGGAAATTGACCAACTCCAAAGTGTAG
GAGATGTGGTTAAAATCATTCAAGGAAAATAG-3'

*Streptococcus Pneumoniae* ACP polypeptide sequence deduced from a polynucleotide sequence in this table [SEQ ID NO: 28] (77 amino acids).
NH$_2$-MKEKEIFDSIVTIIQERQGEDFVVTESLSLKDDLDADSVDLMEFILTLEDEFSIEISDEEID
QLQSVGDVVKIIQGK-COOH

*Streptococcus Pneumoniae* ACP2 DNA polynucleotide sequence [SEQ ID NO: 29] (225 base pairs including stop codon).
5'-
ATGGCAGTATTTGAAAAAGTACAAGAAATTATCGTTGAAGAACTTGGAAAAGACGCATCAGAAGTA
ACACTTGAATCAACTTTTGATGATTTGGACGCAGATTCATTGGACTTGTTCCAAGTAATCTCAGAAAT
CGAAGATGCTTTTGATATCCAAATCGAAGCAGAAAATGACTTGAAAACAGTTGGTGACTTGGTTGCTT
ACGTTGAAGAGCAAGCAAAATAA-3'

*Streptococcus Pneumoniae* ACP2 polypeptide sequence deduced from a polynucleotide sequence in this table [SEQ ID NO: 30] (74 amino acids).
NH$_2$-
MAVFEKVQEIIVEELGKDASEVTLESTFDDLDADSLDLFQVISEIEDAFDIQIEAENDLKTVGDLV
AYVEEQAK-COOH

*H. influenzae* (strain 689) FabH polynucleotide sequence [SEQ ID NO:31] (951 base pairs including stop codon).

TABLE 2-continued

Fab Polynucleotide and Polypeptide Sequences

5'-ATGAATAGTAGAATTTTATCCACCGGTAGCTATCTGCCGAGCCATATTCGCACAAATGCGGATTT
AGAAAAAATGGTTGATACATCAGATGAATGGATTGTCACTCGTTCTGGTATCCGTGAACGTCGTATCG
CAGCGGAAGATGAAACTGTTGCAACAATGGGATTTGAAGCGGCAAAAAATGCGATCGAAGCTGCTCAA
ATTAATCCTCAAGATATTGAACTGATTATTGTTGCAACTACAAGTCACTCACATGCTTATCCAAGTGC
GGCTTGCCAAGTGCAAGGTTTATTAAATATTGATGATGCGATTTCTTTTGATTTAGCCGCAGCTTGCA
CAGGCTTTGTCTATGCTTTGAGCGTAGCTGATCAATTTATTCGTGCAGGCAAAGTGAAAAAAGCCTTA
GTGATAGGCTCAGATCTCAATTCTCGTAAATTAGATGAAACAGATCGCAGCACTGTTGTGCTATTTGG
TGATGGTGCGGGTGCTGTAATTTTAGAAGCGAGTGAACAAGAAGGAATTATCTCCACCCATTTACACG
CTTCAGCAAATAAAAATAATGCCCTTGTTTTAGCTCAGCCAGAACGTGGTATAGAAAAATCTGGCTAT
ATCGAGATGCAAGGTAACGAAACGTTCAAATTGGCAGTTCGTGAACTTTCAAATGTAGTGGAGGAAAC
ACTTTCAGCCAATAATTTAGATAAAAAAGATTTAGACTGGCTTGTGCCACACCAAGCAAATTTACGTA
TTATTACAGCGACAGCTAAAAAATTAGAAATGGATATGTCGCAAGTGGTGGTAACGTTAGATAAATAC
GCTAATAACAGTGCAGCAACAGTGCCTGTCGCTTTAGATGAGGCTGTTCGAGATGGCCGTATTCAACG
TGGGCAGTTACTATTATTAGAAGCCTTTGGCGGTGGTTGGACTTGGGGTTCAGCGTTAGTGAGATTTT
AG-3'

H. influenzae (strain 689) FabH polypeptide sequence deduced from a
polynucleotide sequence in this table [SEQ ID NO:32] (316 amino acids).
NH₂-MNSRILSTGSYLPSHIRTNADLEKMVDTSDEWIVTRSGIRERRIAAEDETV
ATMGFEAAKNAIEAAQINPQDIELIIVATTSHSHAYPSAACQVQGLLNIDDAISFDLAAACTGFVYAL
SVADQFIRAGKVKKALVIGSDLNSRKLDETDRSTVVLFGDG
AGAVILEASEQEGIISTHLHASANKNNALVLAQPERGIEKSGYIEMQGNETFKLAVRELSNVVEETLS
ANNLDKKDLDWLVPHQANLRIITATAKKLEMDMSQVVVTLDKYANNSAATVPVALDEAVRDGRIQRGQ
LLLLEAFGGGWTWGSALVRF-COOH Further sequences in the invention are described in co-pending applications or issued patents as follows:

TABLE 3

| Organism | Gene | Pat. No. Appln. No., or Docket No. | Issue Date or Filing Date |
|---|---|---|---|
| Staphylococcus aureus | FabD | 5,827,689 | 27 Oct. 98 |
| " | FabH | 60/054,884 | 7 Aug. 97 |
| " | FabH | 08/970,647 | 14 Nov. 97 |
| " | FabG | 09/238,481 | 28 Jan. 99 |
| " | FabZ | 09/339,614 | 24 Jun. 99 |
| " | FabI | 08/790,043 | 28 Jan. 97 |
| | | 09/292,411 | 15 Apr. 99 |
| | | 09/292,412 | 15 Apr. 99 |
| " | FabF | GM10238 | 31 Aug. 99 |
| Streptococcus pneumoniae | FabD | 09/308,397 | 14 Nov. 97 |
| " | FabG | 09/239,052 | 27 Jan. 99 |
| " | FabH | 5,759,832 | 02 Jun. 98 |
| | | 5,783,432 | 21 Jul. 98 |
| | | 5,885,572 | 23 Mar. 99 |
| | | 09/074,570 | 07 May 98 |
| | | 09/074,569 | 07 May 98 |
| | | 09/214,995 | 13 Jan. 99 |
| " | FabZ | 09/196,388 | 19 Nov. 98 |
| " | FabF | 09/376,689 | 18 Aug. 99 |
| Pseudomonas aerugenosa | FabG | 09/177,964 | 22 Oct. 98 |
| Streptococcus pneumoniae | FabK | 60/— | 6 Oct. 00 |
| | FabK | 60/— | 6 Oct. 00 |

Deposited Materials

A deposit comprising a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on 11 Apr. 1996 and assigned deposit number 40794. The deposit was described as *Streptococcus pneumoniae* 0100993 on deposit On 17 Apr. 1996 a *Streptococcus pneumoniae* 0100993 DNA library in *E. coli* was similarly deposited with the NCIMB and assigned deposit number 40800. The *Streptococcus pneumoniae* strain, deposit is referred to herein as "the deposited strain" or as "the DNA of the deposited strain."

A deposit comprising a *Staphylococcus aureus* WCUH 29 strain has been deposited with the National Collections of Industrial and Marine Bacteria Ltd. (herein "NCIMB"), 23 St. Machar Drive, Aberdeen AB2 1RY, Scotland on 11 Sep. 1995 and assigned NCIMB Deposit No. 40771, and referred to as *Staphylococcus aureus* WCUH29 on deposit. The *Staphylococcus aureus* strain deposit is referred to herein as "the deposited strain" or as "the DNA of the deposited strain."

The deposited strains comprise full length gene for the gene products described above. The sequence of the polynucleotides comprised in the deposited strain, as well as the amino acid sequence of any polypeptide encoded thereby, are controlling in the event of any conflict with any description of sequences herein.

The deposits of the deposited strains have been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strains are provided merely as convenience to those of skill in the art and is not an admission that a deposit is required for enablement, such as that required under 35 U.S.C. §112. A license may be required to make, use or sell the deposited stain, and compounds derived therefrom, and no such license is hereby granted.

In one aspect of the invention there is provided an isolated nucleic acid molecule encoding a mature polypeptide expressible by the *Streptococcus pneumoniae* 0100993 strain or *Staphylococcus aureus* WCUH 29 strain, which polypeptide is comprised in the respective deposited strain. Further provided by the invention are polynucleotide sequences in the deposited strain, such as DNA and RNA, and amino acid sequences encoded thereby. Also provided by the invention are polypeptide and polynucleotide sequences isolated from the deposited strain.

Polypeptides

Fab polypeptide of the invention is substantially phylogenetically related to other proteins of the fab family.

In one aspect of the invention there are provided polypeptides of an organism of the invention, particularly *streptococci, staphylococci, Escherichia coli* or *Haemophilus influenzae* referred to herein as "fab" and "fab polypeptides" as well as biologically, diagnostically, prophylactically, clinically or therapeutically useful variants thereof, and compositions comprising the same.

Among the particularly preferred embodiments of the invention are variants of fab polypeptide encoded by naturally occurring alleles of a fab gene.

A "fab polypeptide reference sequence" has the sequence of SEQ ID NO: 2, 3, 5, 6, 8, 10, 12, 14, 16, 18, 20, 22, 24, 26, 28, 30 or 32 or a corresponding sequence starting from a useful internal initiating codon.

The present invention further provides for an isolated polypeptide that: (a) comprises or consists of an amino acid sequence that has at least 95% identity, most preferably at least 97–99% or exact identity, to that of a fab polypeptide reference sequence over the entire length of the fab polypeptide reference sequence; (b) a polypeptide encoded by an isolated polynucleotide comprising or consisting of a polynucleotide sequence that has at least 95% identity, even more preferably at least 97–99% or exact identity to a fab polypeptide reference sequence over the entire length of the fab polypeptide reference sequence; (c) a polypeptide encoded by an isolated polynucleotide comprising or consisting of a polynucleotide sequence encoding a polypeptide that has at least 95% identity, even more preferably at least 97–99% or exact identity, to the amino acid sequence of a fab polypeptide reference sequence, over the entire length of the fab polypeptide reference sequence.

The polypeptides of the invention include a polypeptide of a polypeptide reference sequence (in particular a mature polypeptide) as well as polypeptides and fragments, particularly those that have a biological activity of fab, and also those that have at least 95% identity to a polypeptide of a polypeptide reference sequence and also include portions of such polypeptides with such portion of the polypeptide generally comprising at least 30 amino acids and more preferably at least 50 amino acids.

The invention also includes a polypeptide consisting of or comprising a polypeptide of the formula:

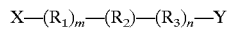

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 2 or modified forms thereof. In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where III and/or n is greater than 1, can be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from streptococci, staphylococi, Escherichia coli or Haemophihis influenzae, however, it can preferably be obtained from other organisms of the same taxonomic genus, or another organism of the invention. A polypeptide of the invention can also be obtained, for example, from organisms of the same taxonomic family or order.

A fragment is a variant polypeptide having an amino acid sequence that is entirely the same as part but not all of any amino acid sequence of any polypeptide of the invention. As with fab polypeptides, fragments can be "free-standing," or comprised within a larger polypeptide of which they form a part or region, most preferably as a single continuous region in a single larger polypeptide.

Preferred fragments include, for example, truncation polypeptides having a portion of an amino acid sequence of a polypeptide reference sequence or of variants thereof, such as a continuous series of residues that includes an amino- and/or carboxyl-terminal amino acid sequence. Degradation forms of the polypeptides of the invention produced by or in a host cell, particularly a streptococci, staphylococci, Escherichia coli or Haemophilus influenzae, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of a fab polypeptide reference sequence, or an isolated polypeptide comprising an amino acid sequence having at least 15, 20, 30, 40, 50 or 100 contiguous amino acids truncated or deleted from the amino acid sequence of the fab polypeptide reference sequence.

Fragments of the polypeptides of the invention can be employed for producing the corresponding full-length polypeptide by peptide synthesis; therefore, these variants can be employed as intermediates for producing the full-length polypeptides of the invention.

Polynucleotides

It is an object of the invention to provide polynucleotides that encode fab polypeptides, particularly polynucleotides that encode a polypeptide herein designated fab.

In a particularly preferred embodiment of the invention the polynucleotide comprises a region encoding fab polypeptides comprising a sequence set out in a polynucleotide reference sequence that includes a full length gene, or a variant thereof. This invention provides that this full length gene is essential to the growth and/or survival of an organism that possesses it, such as from streptococci staphylococci, Escherichia coli or Haemophilus influenzae.

A "fab polynucleotide reference sequence" has the coding sequence of SEQ ID NO: 1, 4, 7, 9, 11, 13, 15, 17, 19, 21, 23, 25, 27, 29 or 31 or a corresponding segment thereof from a useful initiation codon up to (but excluding) the stop codon.

As a further aspect of the invention there are provided isolated nucleic acid molecules encoding and/or expressing fab polypeptides and polynucleotides, particularly from an organism of the invention, especially a streptococci, staphylococci, Escherichia coli or Haemophilus influenzae fab polypeptides and polynucleotides, including, for example, unprocessed RNAs, ribozyrne RNAs, mRNAs, cDNAs, genormic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a fab polypeptide having a deduced amino acid sequence of a polypeptide reference sequence and polynucleotides closely related thereto and variants thereof.

In another particularly preferred embodiment of the invention there is a fab polypeptide from an organism of the invention, particularly *streptococci, staphylococci Escherichia coli* or *Haemophilus influenzae* comprising or consisting of an amino acid sequence of a polypeptide reference sequence, or a variant thereof.

Using the information provided herein, such as a fab polynucleotide reference sequence, a polynucleotide of the invention encoding fab polypeptide can be obtained using standard cloning and screening methods, such as those for cloning and sequencing chromosomal DNA fragments from an organism particularly bacteria, *streptococci, staphylococci, Escherichia coli* or *Haemophilus influenzae* cells as starting material, followed by obtaining a full length clone. For example, to obtain a polynucleotide sequence of the invention, such as a polynucleotide sequence given in Table 2, one typically uses a library of clones of chromosomal DNA of an organism of the invention, particularly *streptococci, staphylococci, Escherichia coli* or *Haemophilus influenzae* in *E. coli* or some other suitable host, which is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (See in particular Screening By Hybridization 1.90 and Sequencing Denatured Double-Stranded DNA Templates 13.70). Direct genormic DNA sequencing can also be performed to obtain a full length gene sequence. Illustrative of the invention, each fab polynucleotide reference sequence was discovered in a DNA library derived from an organism of the invention, particularly *streptococci, staphylococci Escherichia coli* or *Haemophilus influenzae.*

Moreover, each DNA sequence set out in a fab polynucleotide reference sequence contains an open reading frame encoding a protein having about the number of amino acid residues set forth in a polypeptide reference sequence with a deduced molecular weight that can be calculated using amino acid residue molecular weight values well known to those skilled in the art. The polynucleotide of a fab polynucleotide reference sequence, encodes a fab polypeptide reference sequence.

In a further aspect, the present invention provides for an isolated polynucleotide comprising or consisting of: (a) a polynucleotide sequence that has at least 95% identity, even more preferably at least 97–99% or exact identity to a fab polynucleotide reference sequence over the entire length of the fab polynucleotide reference sequence; (b) a polynucleotide sequence encoding a polypeptide that has at least 95% identity, even more preferably at least 97–99% or 100% exact, to the amino acid sequence of a fab polypeptide reference sequence, over the entire length of a fab polynucleotide sequence.

A polynucleotide encoding a polypeptide of the present invention, including homologs and orthologs from species other than *streptococci, staphylococci, Escherichia coli* or *Haemophilus influenzae,* can be obtained by a process that comprises the steps of screening an appropriate library under stringent hybridization conditions with a labeled or detectable probe consisting of or comprising the sequence of a fab polynucleotide reference sequence or a fragment thereof; and isolating a full-length gene and/or genomic clones comprising said polynucleotide sequence.

The invention provides a polynucleotide sequence identical over its entire length to a coding sequence (open reading frame) in a fab polynucleotide reference sequence. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention can also comprise at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence can also comprise additional coding sequence encoding additional amino acids. For example, a marker sequence that facilitates purification of a fused polypeptide can be encoded. In certain embodiments of the invention, the marker sequence is a hexa-histidine peptide, as provided in the pQE vector (Qiagen, Inc.) and described in Gentz et al., *Proc. Natl. Acad Sd., USA* 86: 821–824 (1989), or an HA peptide tag (Wilson et al., *Cell* 37: 767 (1984), both of that can be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotides a fab polynucleotide reference sequence, that encode a fab polypeptide.

The invention also includes a polynucleotide consisting of or comprising a polynucleotide of the formula:

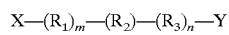

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from Table 2 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, can be either a heteropolymer or a homopolymer, preferably a heteropolymer. Where, in a preferred embodiment, X and Y together define a covalent bond, the polynucleotide of the above formula is a closed, circular polynucleotide, that can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from an organism of the invention, particularly *streptococci, staphylococci, Escherichia coli* or *Haemophilus influenzae*, however, it can preferably be obtained from other organisms of the same taxonomic genus. A polynucleotide of the invention can also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of an organism of the invention, particularly *streptococci, staphylococci, Escherichia coli* or *Haemophilus influenzae* fab having an amino acid sequence set out in a polypeptide reference sequence. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also can comprise coding and/or non-coding sequences.

The invention further relates to variants of the polynucleotides described herein that encode variants of a polypeptide having a deduced amino acid sequence of a polypeptide reference sequence. Fragments of polynucleotides of the invention can be used, for example, to synthesize full-length polynucleotides of the invention.

Further particularly preferred embodiments are polynucleotides encoding fab variants, that have the amino acid sequence of fab polypeptide of a polypeptide reference sequence in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of fab polypeptide.

Preferred isolated polynucleotide embodiments also include polynucleotide fragments, such as a polynucleotide comprising a nucleic acid sequence having at least 15, 20, 30, 40, 50 or 100 contiguous nucleic acids from a fab polynucleotide reference sequence, or a polynucleotide comprising a nucleic acid sequence having at least 15, 20, 30, 40, 50 or 100 contiguous nucleic acids truncated or deleted from the 5' and/or 3' end of the polynucleotide sequence of a fab polynucleotide reference sequence.

Further preferred embodiments of the invention are polynucleotides that are at least 95% or 97% identical over their entire length to a polynucleotide encoding fab polypeptide having an amino acid sequence set out in a polypeptide reference sequence, and polynucleotides that are complementary to such polynucleotides. Polynucleotides that comprise a region that is at least 95% are especially preferred. Furthermore, those with at least 97% are highly preferred among those with at least 95%, and among these, those with at least 98% and at least 99% are particularly highly preferred, with at least 99% being the more preferred.

Preferred embodiments are polynucleotides encoding polypeptides that retain substantially the same biological function or activity as a mature polypeptide encoded by a DNA of a fab polynucleotide reference sequence.

In accordance with certain preferred embodiments of this invention there are provided polynucleotides that hybridize, particularly under stringent conditions, to fab polynucleotide sequences, such as those polynucleotides in Table 2.

The invention further relates to polynucleotides that hybridize to the polynucleotide sequences provided herein. In this regard, the invention especially relates to polynucleotides that hybridize under stringent conditions to the polynucleotides described herein. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization can also be used with the polynucleotide sequences provided by the invention.

The invention also provides a polynucleotide consisting of or comprising a polynucleotide sequence obtained by screening an appropriate library comprising a complete gene for a polynucleotide sequence set forth in a fab polynucleotide reference sequence under stringent hybridization conditions with a probe having the sequence of said polynucleotide sequence set forth in the fab polynucleotide reference sequence or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, can be used as a hybridization probe for RNA, cDNA and genomic DNA to isolate full-length cDNAs and genomic clones encoding fab and to isolate cDNA and genormic clones of other genes that have a high identity, particularly high sequence identity, to a fab gene. Such probes generally will comprise at least 15 nucleotide residues or base pairs. Preferably, such probes will have at least 30 nucleotide residues or base pairs and can have at least 50 nucleotide residues or base pairs. Particularly preferred probes will have at least 20 nucleotide residues or base pairs and will have less than 30 nucleotide residues or base pairs.

A coding region of a fab gene can be isolated by screening using a DNA sequence provided in a fab polynucleotide reference sequence to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention can be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of a fab polynucleotide reference sequence can be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is a mature protein plus additional amino or carboxyl-terminal amino acids, or amino acids interior to a mature polypeptide (when a mature form has more than one polypeptide chain, for instance). Such sequences can play a role in processing of a protein from precursor to a mature form, can allow protein transport, can lengthen or shorten protein half-life or can facilitate manipulation of a protein for assay or production, among other things. As generally is the case in vivo, the additional amino acids can be processed away from a mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences can be an inactive form of the polypeptide. When prosequences are removed such inactive precursors generally are activated. Some or all of the prosequences can be removed before activation. Generally, such precursors are called proproteins.

As will be recognized, the entire polypeptide encoded by an open reading frame is often not required for activity. Accordingly, it has become routine in molecular biology to map the boundaries of the primary structure required for activity with N-terminal and C-terminal deletion experiments. These experiments utilize exonuclease digestion or convenient restriction sites to cleave coding nucleic acid sequence. For example, Promega (Madison, Wis.) sell an Erase-a-base™ system that uses Exonuclease III designed to facilitate analysis of the deletion products (protocol available at www.promega.com). The digested endpoints can be repaired (e.g., by ligation to synthetic linkers) to the extent necessary to preserve an open reading frame. In this way, the nucleic acid of a fab polynucleotide reference sequence readily provides contiguous fragments of a fab polypeptide reference sequence to provide an activity, such as an enzymatic, binding or antibody-inducing activity. Nucleic acid sequences encoding such fragments of a polypeptide reference sequence and variants thereof as described herein are within the invention, as are polypeptides so encoded.

As is known in the art, portions of the N-terminal and/or C-terminal sequence of a protein can generally be removed without serious consequence to the function of the protein. The amount of sequence that can be removed is often quite substantial. The nucleic acid cutting and deletion methods used for creating such deletion variants are now quite routine. Accordingly, any contiguous fragment of a polypeptide reference sequence which retains at least 20%, preferably at least 50%, of an activity of the polypeptide encoded by the gene for a polypeptide reference sequence is within the invention, as are corresponding fragment which are 70%, 80%, 90%, 95%, 97%, 98% or 99% identical to such contiguous fragments. In one embodiment, the contiguous fragment comprises at least 70% of the amino acid residues of a polypeptide reference sequence, preferably at least 80%, 90% or 95% of the residues.

In addition to the substitutions, deletions or insertions described above, one highly preferred embodiment of the invention encompasses segments of nucleic acid that encode all or part of a Fab Polypeptide reference sequence. When the nucleic acid is intended for use with an organism that uses the most standard genetic code, this means that the codons encoding the following amino acids can be substituted from within the groups of trinucleotides defined in the corresponding entry below Table 4:

TABLE 4

| Coded AMINO ACID | Trinucleotides |
| --- | --- |
| Ala—Alanine | GCX |
| Arg—Arginine | CGX or AGR |
| Asn—Asparagine | AAY |
| Asp—Aspartic Acid | GAY |
| Cys—Cysteine | TGY |
| Gln—Glutamine | CAR |
| Glu—Glutamic Acid | GAR |
| Gly—Glycine | GGX |
| His—Histidine | CAY |
| Ile—Isoleucine | ATH |
| Leu—Leucine | CTX |
| Lys—Lysine | AAR |
| Met—Methionine | ATG |
| Phe—Phenylalanine | TTY |
| Pro—Proline | CCX |
| Ser—Serine | TCX or AGY |
| Thr—Threonine | ACX |
| Trp—Tryptophan | TGG |
| Tyr—Tyrosine | TAY |
| Val—Valine | GTX |

In the above table: X represents any A, G, T/U or C; R represents A or G, Y represents C or T/U; and H represents A, C or T/U, but not G. Also, any recital of "T" above can be substituted with "U."

In sum, a polynucleotide of the invention can encode a mature protein, a mature protein plus a leader sequence (that can be referred to as a preprotein), a precursor of a mature protein having one or more prosequences that are not the leader sequences of a preprotein, or a preproprotein, that is a precursor to a proprotein, having a leader sequence and one or more prosequences, that generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention can be prepared by processes well known to those skilled in the art from genetically engineered host cells comprising expression systems. Accordingly, in a further aspect, the present invention relates to expression systems that comprise a polynucleotide or polynucleotides of the present invention, to host cells that are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of *streptococci, staphylococci, enterococci E. coli, streptomyces, cyanobacteria, Bacillus subtilis,* and *streptococci, staphylococci, Escherichia coli* or *Haemophilus influenzeae;* fungal cells, such as cells of a yeast, *Kluveromyces, Saccharomyces,* a basidiomycete, *Candida albicans* and *Aspergillus,* insect cells such as cells of *Drosophila* S2 and *Spodoptera* Sf9, animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as. SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids. The expression system constructs can comprise control regions that regulate as well as engender expression. Generally, any system or vector suitable to maintain, propagate or express polynucleotides and/or to express a polypeptide in a host can be used for expression in this regard. The appropriate DNA sequence can be inserted into the expression system by any of a variety of well-known and routine techniques, such as, for example, those set forth in Sambrook e al., *MOLECULAR CLONING, A LABORATORY MANUAL,* (supra).

In recombinant expression systems in eukaryotes, for secretion of a translated protein into the lumen of the endoplasmic reticulum into the periplasmic space or into the extracellular environment, appropriate secretion signals can be incorporated into the expressed polypeptide. These signals can be endogenous to the polypeptide or they can be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein can be employed to regenerate active conformation when the polypeptide is denatured during isolation and/or purification.

Antagonists and Agonists—Assays and Molecules

Compounds that may be screened for binding using a method of the invention (herein also "bioactive agent(s)") may be identified or selected from a variety of sources, for example, cells, cell-free preparations, known or newly synthesized compounds, chemical libraries, and natural product mixtures.

Bioactive agents of the invention include, among others, small organic molecules, peptides, polypeptides and antibodies that bind to a polynucleotide and/or polypeptide of the invention and thereby inhibit or extinguish its activity or expression. Bioactive agents may be a small organic molecule, a peptide, a polypeptide, a closely related protein or antibody that binds the same sites on a binding molecule without inducing kinase-induced activities.

Antagonists of the invention further include small molecules that bind to and occupy the binding site of a kinase thereby preventing binding to cellular binding molecules, such that normal biological activity is prevented. Examples of small molecules include but are not limited to small organic molecules, peptides or peptide-like molecules. Other antagonists include antisense molecules (see Okano, *J. Neurochem.* 56 560 (1991); *OLIGODEOXYNUCLEOTIDES AS AN ANTISENSE INHIBITORS OF GENE EXPRESSION,* CRC Press, Boca Raton, Fla. (1988), for a description of these molecules).

Bioactive agents of the invention that are small molecules preferably have a molecular weight below 2,000 daltons, more preferably between 300 and 1,000 daltons, and most preferably between 400 and 700 daltons. It is particularly preferred that these small molecules are organic molecules.

Polypeptides and polynucleotides of the invention can also be used to assess the binding of small molecule substrates and ligands in, for example, cells, cell-free preparations, chemical libraries, and natural product mixtures. These substrates and ligands can be natural substrates and ligands or can be structural or functional mimetics. See, e.g., Coligan et al., *Current Protocols in Immunology* 1(2): Chapter 5 (1991).

Polypeptides and polynucleotides of the present invention are responsible for many biological functions, including many disease states, in particular the Diseases herein mentioned. It is therefore desirable to devise screening methods to identify compounds that agonize (e.g., stimulate) or that antagonize (e.g., inhibit) the function of the polypeptide or polynucleotide. Accordingly, in a further aspect, the present invention provides for a method of screening compounds to identify those that agonize or that antagonize the function of a polypeptide or polynucleotide of the invention, as well as related polypeptides and polynucleotides. In general, agonists or antagonists (e.g., inhibitors) can be employed for therapeutic and prophylactic purposes for such Diseases as herein mentioned. Compounds can be identified from a variety of sources, for example, cells, cell-free preparations, chemical libraries, and natural product mixtures. Such agonists and antagonists so-identified can be natural or modified substrates, ligands, receptors, enzymes, etc, as the case can be, of fab polypeptides and polynucleotides; or can be structural or functional mimetics thereof (see Coligan et al., *Current Protocols in Immunology* 1(2):Chapter5 (1991)).

The screening methods can simply measure the binding of a bioactive agent to the polypeptide or polynucleotide, or to cells or membranes bearing the polypeptide or polynucleotide, or a fusion protein of the polypeptide by means of a label directly or indirectly associated with the bioactive agent. Alternatively, the screening method can involve competition with a labeled competitor. Further, these screening methods can test whether the bioactive agent results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the bioactive agent is observed. Constitutively active polypeptide and/or constitutively expressed polypeptides and polynucleotides can be employed in screening methods for inverse agonists, in the absence of an agonist or antagonist, by testing whether the bioactive agent results in inhibition of activation of the polypeptide or polynucleotide, as the case can be. Further, the screening methods can simply comprise the steps of mixing a bioactive agent with a solution comprising a polypeptide or polynucleotide of the present invention, to form a mixture, measuring fab polypeptide and/or polynucleotide activity in the mixture, and comparing the fab polypeptide and/or polynucleotide activity of the mixture to a standard. Fusion proteins, such as those made from Fc portion and fab polypeptide, as herein described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16):9459–9471 (1995)).

The polynucleotides, polypeptides and antibodies that bind to and/or interact with a polypeptide of the present invention can also be used to configure screening methods for detecting the effect of added compounds on the production of mRNA and/or polypeptide in cells. For example, an ELISA assay can be constructed for measuring secreted or cell associated levels of polypeptide using monoclonal and polyclonal antibodies by standard methods known in the art. This can be used to discover agents that can inhibit or enhance the production of polypeptide (also called antagonist or agonist, respectively) from suitably manipulated cells or tissues.

The invention also provides a method of screening compounds to identify those that enhance (agonist) or block (antagonist) the action of fab polypeptides or polynucleotides, particularly those compounds that are bacteristatic and/or bactericidal. The method of screening can involve high-throughput techniques. For example, to screen for agonists or antagonists, a synthetic reaction mix, a cellular compartment or component, such as a membrane, cell envelope, cytoplasmic extract or cell wall, or a preparation of any thereof, comprising fab polypeptide and a labeled substrate or ligand of such polypeptide is incubated in the absence or the presence of a candidate molecule that can be a fab agonist or antagonist. The ability of the candidate molecule to agonize or antagonize the fab polypeptide is reflected in deceased binding of the labeled ligand or decreased production of product from such substrate. Molecules that bind gratuitously, i.e., without inducing the effects of fab polypeptide are most likely to be good antagonists. Molecules that bind well and, as the case can be, increase the rate of product production from substrate, increase signal transduction, or increase chemical channel activity are agonists. Detection of the rate or level of, as the case can be, production of product from substrate, signal transduction, or chemical channel activity can be enhanced by using a reporter system. Reporter systems that can be useful in this regard include but are not limited to calorimetric, labeled substrate converted into product, a reporter gene that is responsive to changes in fab polynucleotide or polypeptide activity, and binding assays known in the art.

In one embodiment of the invention the fab polypeptides, or polynucleotides encoding the fab polypeptides, of the invention provide Fab enzymes involved in the core cycle of bacterial fatty acid biosynthesis. The Fab polypeptides of the present invention include the full length polypeptides and/or biologically active fragments thereof. The preferred fragments contain the substrate binding site and, more preferably, are of a size which allows for their use in the screening methods of the present invention. Another aspect of this embodiment provides reaction conditions sufficient for the action of enzymes, including Fab enzymes, appropriate for bacterial fatty acid biosynthsesis. Sufficient conditions for bacterial fatty acid biosynthesis can include the addition to the above proteins, acyl carrier protein (ACP), biotinylated-ACP, acyl carrier protein synthase (ACPS) or acyl ACPS (AAS). Incubation conditions, such as salt concentrations, pH, stabilizers, and the like are well known in the art for the enzymes, as illustrated in Heath and Rock, J. Biol. Chem. 271, 1833–1836, 1996. it will be recognized that optimal conditions can vary with the mixture of enzymes used. Suitable conditions can be determined by ordinary experimentation.

Recombinant ACP is expressed in host bacteria with at least a portion of the ACP containing the 4'-phosphopantetheine prosthetic group. The holoprotein can be isolated from the remainder by standard chromatography techniques, such as chromatography using reverse phase HPLC, gel filtration media and ion exchange media such as DEAE Sepharose Illustrative ACP sequences are presented above and the E. coli gene for an ACP is described, for example, in GenBank Accession No. M84991. Recombinant ACP can be produced, for example, as described in Jones et al., Biochem. Soc. Trans. 21: 202S–202S, 1993. ACP synthase, which adds the prosthetic group to ACP using CoA as the source substrate, can be isolated from a source bacteria (e.g. E. coli) by overexpressing the ACP synthase in E. coli and purifying the overexpressed enzyme by conventional methods. The E. coli ACP synthase gene is described, for example in GenBank Accession No. L14681, and can be recombinantly expressed as described, for example, in Jackowski et al., J Biol Chem, 269(4): 2921–8, 1994.

The term "enzyme" includes polymorphic variants that are silent mutations naturally found within the microorganism population of a strain or species. The enzymes in the preferred embodiment of the invention are fatty acid biosynthesis enzymes, however there is no intent to limit the invention to these enzymes. The term fatty acid biosynthesis enzymes (and its equivalent term fatty acid biosynthetases) is intended to include those components of proteins or polypeptides capable of synthesizing fatty acids via the three-carbon intermediate, malonyl CoA. The proteins include acyl carrier protein (ACP), malonyl-CoA:ACP transacylase (i.e., fabD), β-ketoacyl-ACP synthase III (i.e., fabH), NADPH-dependent β-ketoacyl-ACP reductase (i.e., fabg), β-hydroxyacyl-ACP dehydrase (i.e., fabA or fabZ), NADH- or NADPH-dependent enoyl-ACP reductase or enoyl-ACP reductase (i.e., fabI), β-ketoacyl-ACP synthase I (i.e., fabB ), β-ketoacyl-ACP synthase II (i.e., fabF), and acetyl CoA-ACP transacetylase. The ACP of *E. coli* and of other organisms contains the prosthetic group 4'-phosphopantetheine, to which the growing fatty acid chain is covalently linked by a thioester bond. The term "enzymes" is art recognized for purposes of this invention and can refer to whole intact enzyme or portions or fragments thereof.

The present invention further pertains to a method for identifying an antimicrobial compounds that interact with a mutant Fab polypeptide by contacting the mutant Fab polypeptide with a compound under conditions which allow interaction of the compound with the mutant Fab polypeptide to occur. In this method, the presence or absence of interaction of the compound with the mutant Fab polypeptide is detected as an indication of whether the compound is an antimicrobial compound.

The language "mutant of a Fab polypeptide" is intended to include polypeptides which differ from the Fab polypeptide in an alteration of at least one amino acid residue but retain their ability to be useful within the screening assays of the present invention. The mutant Fab polypeptides of the present invention include the full length mutant Fab polypeptide and/or biologically active fragments thereof. The preferred fragments contain the substrate binding portion and are of a size which allows for their use in the screening methods of the present invention.

A particularly preferred embodiment of the invention is a screen, which can be a High Throughput Screen (HTS) for biological agents affecting fatty acid biosynthesis. Enzymes provided in this embodiment can include, for example, FabD, FabH, FabG, FabZ, FabI and FabF. Substrates for these enzymes can be provided by a reaction mixture that includes holo-ACP, a bacterial enzymatic pathway comprising two or more of FabD, FabH, FabG, FabZ and Fab I, as well as any substrates (e.g. malonyl CoA) or cofactors required for the operation of the enzymes and, in some embodiments, FabF. In a preferred aspect of the screen, a NADH-specific enoyl-ACP reductase is used as the enoyl-ACP reductase, FabI. Further provided by the screen are reaction conditions sufficient for the action of these enzymes on substrates. Enzymes can be derived from *Staphylococcus aureus* or *Streptococcus pneumoniae*, or other bacteria. In certain preferred aspects FabI or ACP, are derived from *Escherichia coli* or *Haemophilus influenzae*. Enzymes from *E. coli, Streptococcus pneumoniae, Staphylococcus aureus* or *Haemophilus influenzae* or other homologues can be used to determine specificity of hits. Human FAS1 or other eukaryotic pathways can form the basis of the selectivity screen. Intermediate substrates in the reacting step can be provided in the screen, wherein the intermediate substrates are not derived from said malonyl CoA and are provided in an amount adapted to maintain such intermediate substrates at a concentration at least approaching the $K_m$ of the respective enzyme that acts on the substrate during the assay timeframe.

The screen can be used by contacting the reaction mixture with a biological agent, conducting a high throughput measurement of the activity of the enzymatic pathway and determining if the contacting altered the activity of the enzymatic pathway. Measurement of the activity of the enzymatic pathway can involve measurement of the activity of enoyl-ACP reductase, FabI. Methods of high throughput measurement can include spectrophotometrically measuring the consumption of NADH or providing [$^3$H]NADH as a cofactor to the enzymatic pathway and capturing a radioactive product on a support that provides a scintillant.

In a further embodiment of the present invention, there is provided to the screen NADPH in a substantially constant amount such that the NADH consumption by enoyl-ACP reductase (FabI) can be quantitated accurately and without interference, or an amount effective to reduce NADH consumption by more NADPH-dependent enzymes. An NADPH regenerating enzyme system can be provided to the reacting step of the screen. In a further aspect of the invention there can be provided, or included in the screen, any of the following: a β-ketoacyl-ACP synthase III derived from *E. coli* or *Haemophilus influenzae* as the β-ketoacyl-ACP synthase III, a malonyl-CoA:ACP transacylase derived from *Streptococcus* or *Staphylococcus*, a β-ketoacyl-ACP synthase III derived from *Streptococcus, Staphylococcus, Haemophilus influenzae* or *Escherichia*, a NADPH-dependent β-ketoacyl-ACP reductase derived from *Streptococcus* or *Staphylococcus*, a β-hydroxyacyl-ACP dehydrase derived from *Streptococcus* or *Staphylococcus*, and an enoyl-ACP reductase derived from *Staphylococcus, Haemophilus influenzae* or *Escherichia*. In another aspect of the present invention β-ketoacyl-ACP synthase II is part of the enzymatic pathway.

Figure 2:
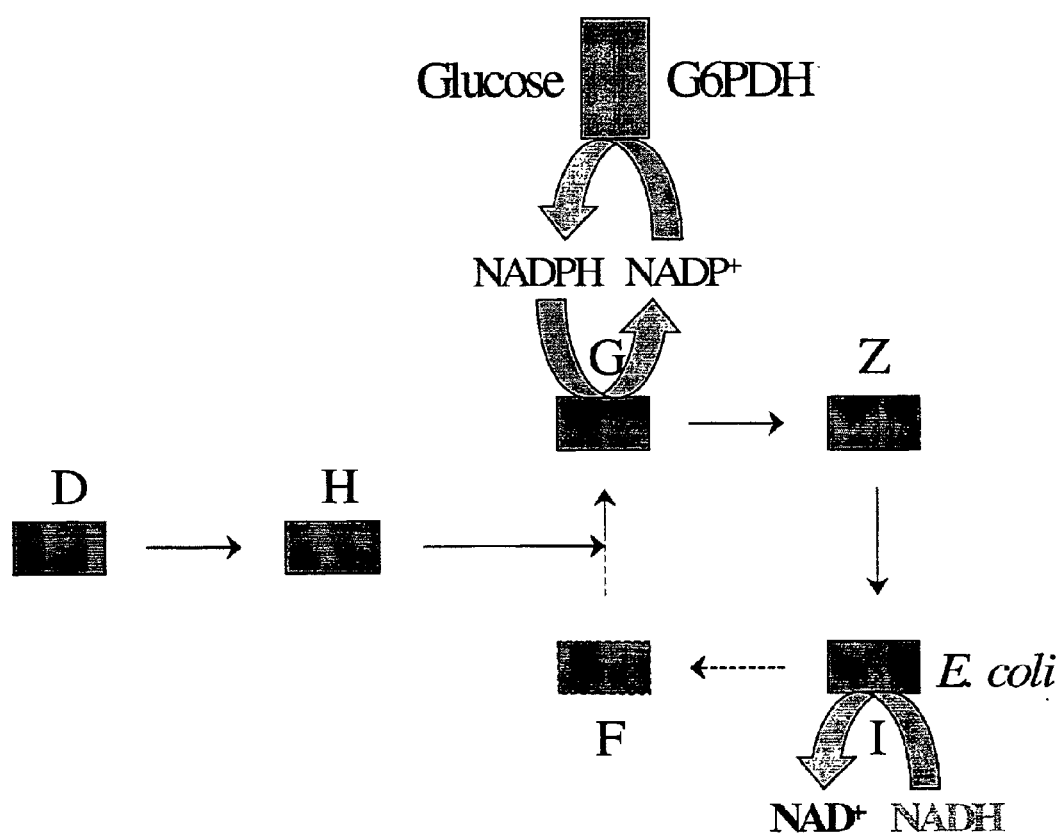
FIG. 2 illustrates a configuration for a continuous assay.

FIG. 2 shows a preferred configuration for a continuous assay monitoring the oxidation of NADH at FabI, which is the assay of choice. A preferred point for measuring flux through the pathway is FabI. In the Figure, the similarly sized boxes representing each of the enzymes in the pathway reflects a preference for balancing their concentrations so that each is equally rate-limiting. This allows inhibition of any step to be readily detected. Estimation of the basic kinetic parameters for each enzyme can be conducted as is known in the art prior to the assembly of the pathway so that critical substrates and intermediates can be maintained at or below Km levels. Computer simulation of the pathway can be used to make such estimations.

Since *S. aureus* FabI utilizes both NADH and NADPH as substrates, use of for example the *E. coli* enzyme, which is specific for NADH, can help discriminate between fluxes through FabI or FabG. Appropriate adjustment of the concentration of NADPH to maintain, for example a substantially constant amount, such that the NADH consumption by enoyl-ACP reductase (FabI) can be quantitated accurately and without interference. An NADPH-regenerating system involving glucose and a large excess of glucose 6-phosphate dehydrogenase is proposed to prevent its utilization from interfering with the detection of the signal from NADH.

Since FabF is downstream from FabI, inhibitors of FabF would most likely go undetected, even in the context of a cyclical pathway. Elimination of FabF converts the partially linear, partially cyclical pathway to a simple linear pathway that can simplify assay configuration, and limit the number of potential intermediates, which can be produced as a result of multiple turns of the cycle. A separate HTS for FabF using a coupled, spectrophotometric assay through FabG can be conducted.

Figure 3:
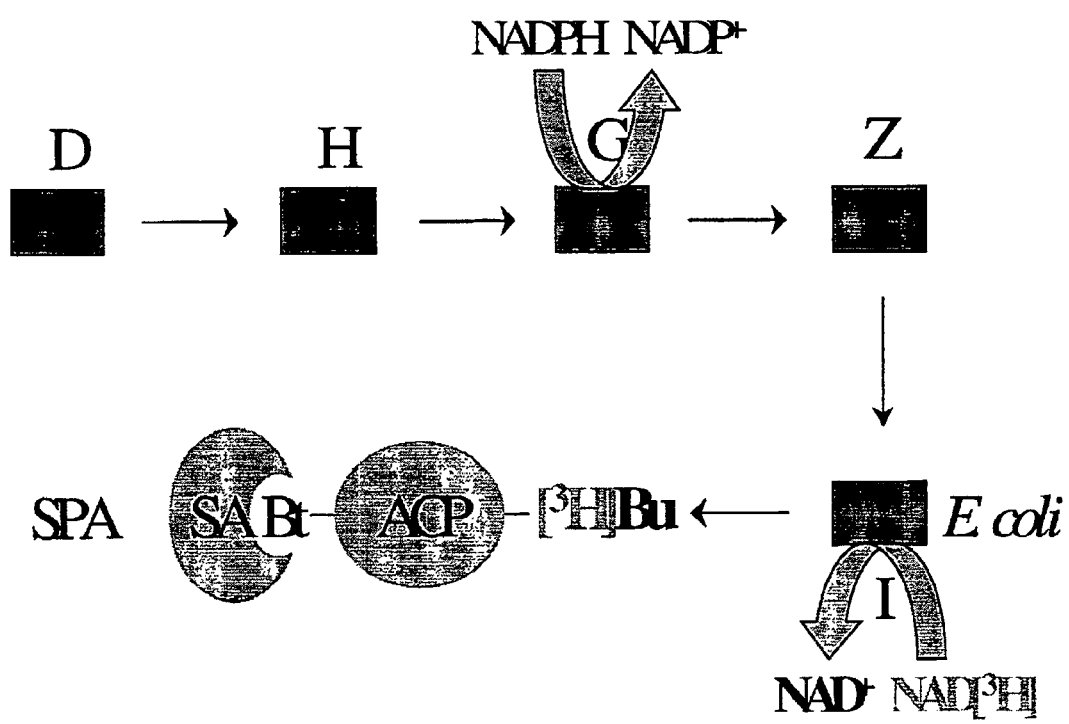
FIG. 3 illustrates data from an SPA-based screening assay.

An alternative preferred configuration, which is an SPA-based screening assay is shown in FIG. 3. This assay utilizes biotinylated apo-ACP as an initiating substrate. Radiolabel is incorporated into the acyl group from NAD[$^3$H] through the action of FabI. The radiolabeled, biotinylated acyl-ACP is then captured and detected with streptavidin-coated SPA beads. The pathway is made linear by the omission of FabF in order to produce a single, distinct product for detection. *E. coli* or *Haemophillus influenzae* FabI is also used in a preferred aspect of this assay. Care is taken to assure through controls that no isotope effect significantly affects the assay.

The screen can include, when a bioactive agent affecting the enzymatic pathway is identified applying one or more deconvolution assays for determining which enzymes in the enzyme pathway are affected. Such deconvolution assays comprise contacting the identified bioactive agent with (i) an enzyme in the enzymatic pathway or (ii) two or more, but less than all, enzymes acting sequentially in the enzymatic pathway.

Deconvolution of primary hits can be conducted without the need for screening all hits against each of the component enzymes. Quantitation of reaction intermediates can be done, for example, using mass spectroscopy, or quantitation of acyl-ACPs after separation using conformationally-sensitive gel electrophoresis. Assays for individual enzymes in the pathway will be set up for follow-up and mechanistic analysis. Potential configurations for these are listed below. Note that in all the assays of the invention, including those detailed below, acyl-CoA is substituted for acyl-ACP.

Preferred embodiments of the FAS pathway assays of the invention are as follows:

FabD: Assayed by:
1. A filtration assay of TCA-precipitable product using 2-[$^{14}$C]malonyl CoA as substrate; or
2. An assay that monitors production of malonyl-ACP by coupling through FabH using [$^3$H]acetyl-CoA as substrate. Radiolabeled acetoacetyl-ACP is detected via TCA precipitation or by streptavidin-SPA using biotinylated holo-ACP as the starting substrate. Alternatively, the assay can use acyl-CoA instead of acyl-ACP.

FabH: Assayed by:
1. An assay to monitor production of radiolabeled acetoacetyl-ACP from [$^3$H]acetyl CoA either via TCA precipitation or by streptavidin-SPA using biotinylated malonyl-ACP as the starting substrate, or by coupling to FabG as in FabF below, or by using malonyl-CoA as a malonyl-ACP surrogate.

FabG: Assayed by:
1. A spectrophotometric assay that continuously monitors the consumption of NADP; or
2. Monitor production of radiolabeled 3-hydroxybutyryl-ACP from NADP[$^3$H]. The product is detected either via TCA precipitation or by streptavidin-SPA using biotinylated acetoacetyl-ACP as the starting substrate.

FabZ: Assayed by:
1. A continuous spectrophotometric assay (NADH consumption) coupled through FabI to monitor production of crotonoyl ACP, or
2. Monitor production of crotonoyl-ACP by coupling through FabI using NAD[3H] as substrate. Radiolabeled butyryl-ACP is detected either via TCA precipitation or by streptavidin-SPA using biotinylated 3-hydroxybutyryl-ACP as the starting substrate.

FabI: Assayed by:
1. Continuous spectrophotometric assay to monitor consumption of NADH, or
2. Using NAD[$^3$H] as a substrate, monitor the production of radiolabeled butyryl-ACP either via TCA precipitation or by streptavidin-SPA using biotinylated crotonoyl-ACP as the starting substrate.

FabF: Assayed by:
1. Coupling with FabG in a continuous spectrophotometric assay to monitor the consumption of NADPH, or
2. Coupling with FabG in a spectrophotometric assay for detecting changes in NADH or NAD$^+$ concentration or an assay measuring incorporation of radiolabel from NAD [$^3$H]. Radiolabeled 3-hydroxyhexanoyl-ACP is detected either via TCA precipitation or by streptavidin-SPA using biotinylated butyryl-ACP as the starting substrate, or
3. Monitoring the incorporation of radiolabel from [$^{14}$C]-malonyl-ACP via TCA precipitation.

The screen can comprise a reaction mixture including (a) holo-ACP or $^{14}$C-malonyl-CoA, (b) malonyl CoA, (c) a bacterial enzymatic pathway comprising (i) malonyl-CoA:ACP transacylase, (ii) β-ketoacyl-ACP synthase III, (iii) NADPH-dependent β-ketoacyl-ACP reductase, (iv) β-hydroxyacyl-ACP dehydrase and (v) enoyl-ACP reductase and (d) the cofactors required for the operation of the enzymes; contacting the reaction mixture with the reaction mixture; conducting a measurement of the activity of the enzymatic pathway; and determining if the contacting altered the activity of the enzymatic pathway, wherein at least one of the following applies: (1) the enoyl-ACP reductase is a NADH-specific enoyl-ACP reductase; or (2) the β-ketoacyl-ACP synthase III is a β-ketoacyl-ACP synthase III derived from *E. coli* or *Haemophilus influenzae*; or (3) providing NADPH to the reacting step in a substantially constant amount such that the NADH consumption by FabI can be quantitated accurately and without interference or an amount effective to reduce NADH consumption by more NADPH-dependent enzymes; or (4) the NADPH-dependent β-ketoacyl-ACP reductase is derived from *streptococci* or *staphylococci*.

In a further aspect, the present invention provides methods of treating abnormal conditions such as, for instance, a Disease, related to either an excess of, an under-expression of, an elevated activity of, or a decreased activity of fab polypeptide and/or polynucleotide.

If the expression and/or activity of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide can be administered. Typical examples of such competitors include fragments of the fab polypeptide and/or polypeptide.

Each of the polynucleotide sequences provided herein can be used in the discovery and development of antibacterial compounds. The encoded protein, upon expression, can be used, as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention can be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial fab proteins that mediate tissue damage and/or, to block the normal progression of pathogenesis in infections initiated other than by the implantation of in-dwelling devices or by other surgical techniques.

In accordance with yet another aspect of the invention, there are provided fab agonists and antagonists, preferably bacteristatic or bactericidal agonists and antagonists.

The antagonists and agonists of the invention can be employed, for instance, to prevent, inhibit and/or treat diseases.

Antagonists of the invention include, among others, small organic molecules, peptides, polypeptides and antibodies that bind to a polynucleotide and/or polypeptide of the invention and thereby inhibit or extinguish its activity or expression. Antagonists also can be small organic molecules, a peptide, a polypeptide such as a closely related protein or antibody that binds the same sites on a binding molecule, such as a binding molecule, without inducing fab-induced activities, thereby preventing the action or expression of fab polypeptides and/or polynucleotides by excluding fab polypeptides and/or polynucleotides from binding.

Antagonists of the invention also include a small molecule that binds to and occupies the binding site of the polypeptide thereby preventing binding to cellular binding molecules, such that normal biological activity is prevented Examples of small molecules include but are not limited to small organic molecules, peptides or peptide-like molecules. Other antagonists include antisense molecules (see Okano, J. Neurochem. 56: 560 (1991); OLIGODEOXYNUCLE-OTIDES AS ANTISENSE INHIBITORS OF GENE EXPRESSION, CRC Press, Boca Raton, Fla. (1988), for a description of these molecules). Preferred antagonists include compounds related to and variants of fab.

Other examples of polypeptide antagonists include antibodies or, in some cases, oligonucleotides or proteins that are closely related to the ligands, substrates, receptors, enzymes, etc., as the case can be, of the polypeptide, e.g., a fragment of the ligands, substrates receptors, enzymes, etc.; or small molecules that bind to the polypeptide of the present invention but do not elicit a response, so that the activity of the polypeptide is prevented.

Small molecules of the invention preferably have a molecular weight below 2,000 daltons, more preferably between 300 and 1,000 daltons, and most preferably between 400 and 700 daltons. It is preferred that these small molecules are organic molecules.

Definitions

The following terms shall have, for the purposes of this application, the respective meaning set forth below.

acyl carrier moiety. An acyl carrier moiety is a substance effective to carry the acyl moiety which are acted upon as intermediates towards the biosynthesis of fatty acids in the fatty acid synthesis pathway relevant to the invention. Examples include: (1) holo-ACP; or (2) apoACP, CoA and acyl carrier protein synthase (ACPS) or acyl ACPS (AAS); and (3) acyl-CoA.

bioactive agent. A bioactive agent is a substance such as a chemical that can act on a cell, virus, tissue, organ or organism, including but not limited to insecticides or drugs (i.e., pharmaceuticals) to create a change in the functioning of the cell, virus, organ or organism. Preferably, the organism is a mammal, more preferably a human. In preferred embodiments of the invention, methods of identifying bioactive agents of the invention are applied to organic molecules having molecular weight of about 1500 or less.

cofactors. Cofactors are ancillary substrates (i.e., substrates that do not provide carbon to the product of an enzyme or enzymatic pathway) such as NADH or are reagents that provide enzyme conditions that are favorable to the enzyme-catalyzed reaction, such as reaction-facilitating salts or buffering agents.

enzyme naming. The enzymes used herein are often referred to by certain gene names, such as fabD, fabH, and the like. When the gene name is used herein it should be understood that, except for preferred embodiments, what is referred to is any microbial enzyme having the corresponding enzymatic activity. Known correspondences include the following:

malonyl-CoA:ACP transacylase or fabD

β-ketoacyl-ACP synthase III or fabH

NADPH-dependent β-ketoacyl-ACP reductase or fabG

β-hydroxyacyl-ACP dehydrase or fabA or fabZ (preferred)

NADH- or NADPH-dependent enoyl-ACP reductase or enoyl-ACP reductase or fabI

β-ketoacyl-ACP synthase I or fabB

β-ketoacyl-ACP synthase I or II, such as fabB or fabF (preferred)

high throughput measurement. A high throughput measurement is a measurement of enzyme activity that can be taken in situ in the reaction mixture, without chemical separation, including separation of a solid phase from a liquid phase.

intermediate substrates. Intermediate substrates are substances produced by one step of an enzymatic pathway that are used in a subsequent step.

NADPH regenerating enzyme system. A NADPH regenerating enzyme system is at least one enzyme and at least one substrate therefor effective to convert $NADP^+$ to NADPH. An example of a NADPH regenerating enzyme system is glucose-6-phosphate dehydrogenase, hexokinase, ATP, and glucose.

Disease(s) means any disease caused by or related to infection by a bacteria, including, for example, disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (eg., secretory diarrhoea, splenic abscesses, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric abscesses, toxic shock syndrome), skin (e.g., impetigo, folliculitis, cutaneous abscesses, cellulitis, wound infection, bacterial myositis) bone and joint (e.g., septic arthritis, osteomyelitis).

Host cell(s) is a cell that has been introduced (e.g., transformed or transfected) or is capable of introduction (e.g., transformation or transfection) by an exogenous polynucleotide sequence.

Identity, as known in the art, is a relationship between two or more polypeptide sequences or two or more polynucleotide sequences, as the case can be, as determined by comparing the sequences. In the art, "identity" also means the degree of sequence relatedness between polypeptide or polynucleotide sequences, as the case can be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (BLAST *Manual,* Altschul, S., et al., NCBI NLM NIH Bethesda, Md. 20894; Altschul, S., et al., *J. Mol. Biol.* 215: 403–410 (1990). The well known Smith Waterman algorithm can also be used to determine identity.

Parameters for polypeptide sequence comparison include the following:
Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89: 10915–10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:
Algorithm:
Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case can be, are provided in (1) and (2) below.

(1) Polynucleotide embodiments further include an isolated polynucleotide comprising a polynucleotide sequence having at least a 95, 97 or 100% identity to the reference sequence of a fab polynucleotide reference sequence, wherein said polynucleotide sequence can be identical to the reference sequence of the fab polynucleotide reference sequence or can include up to a certain integer number of nucleotide alterations as compared to the reference sequence, wherein said alterations are selected from the group consisting of at least one nucleotide deletion, substitution, including transition and transversion, or insertion, and wherein said alterations can occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in a fab polynucleotide reference sequence by the integer defining the percent identity divided by 100 and then subtracting that product from said total number of nucleotides in the fab polynucleotide reference sequence, or.

$$n_n \leq x_n - (x_n \cdot y),$$

wherein $n_n$ is the number of nucleotide alterations, $x_n$ is the total number of nucleotides in a polynucleotide reference sequence, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of a polypeptide reference sequence can create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 95, 97 or 100% identity to a polypeptide reference sequence of a polypeptide reference sequence, wherein said polypeptide sequence can be identical to the reference sequence of a polypeptide reference sequence or can include up to a certain integer number of amino acid alterations as compared to the reference sequence, wherein said alterations are selected from the group consisting of at least one amino acid deletion, substitution, including conservative and non-conservative substitution, or insertion, and wherein said alterations can occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in a polypeptide reference sequence by the integer defining the percent identity divided by 100 and then subtracting that product from said total number of amino acids in a polypeptide reference sequence, or:

$$n_a \leq x_a - (x_a \cdot y),$$

wherein $n_a$ is the number of amino acid alterations, $x_a$ is the total number of amino acids in a polypeptide reference sequence, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

Individual(s) means a multicellular eukaryote, including, but not limited to a metazoan, a mammal, an ovid, a bovid, a simian, a primate, and a human.

Isolated means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolalated", as the term is employed herein. Moreover, a polynucleotide or polypeptide that is introduced into an organism by transformation, genetic manipulation or by any other recombinant method is "isolated" even if it is still present in said organism, which organism can be living or non-living.

Organism(s) means a (i) prokaryote, including but not limited to, a member of the genus *Streptococcus, Staphylococcus, Bordetella, Corynebacterium,*

*Mycobacterium, Neisseria Haenophilus, Actinomycetes, Streptomycetes, Nocardia, Enterobacter, Yersinia, Fancisella, Pastuella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma,* and further including, but not limited to, a member of the species or group, Group A *Streptococcus,* Group B *Streptococcus,* Group C *Streptococcus,* Group D *Streptococcus,* Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacteriwn tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Keibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridiun botulinum, Treponema pallidium, Rickettsia rickettsii, Helicobacter pylori* and *Chlamydia trachomitis,* (ii) an archaeon, including but not limited to *Archaebacter,* and (iii) a unicellular or filamentous eukaryote, including but not limited to, a protozoan, a fungus, a member of the genus *Saccharomyces, Kluveromyces,* or *Candida*, and a member of the species *Saccharomyces cenviseae, Kluveromyces lactis,* or *Candida albicans.*

Polypeptide(s) refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides can comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art It will be appreciated that the same type of modification can be present in the samne or varying degree at several sites in a given polypeptide. Also, a given polypeptide can comprise many ypes of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, fonnylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttraslational Protein Modifications: Perspectives and Prospects, pgs. 1–12 in *POST-TRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides can be branched or cyclic, with or without branching. Cyclic, branched and branched circular polypeptides can result from post-translational natural processes and can be made by entirely synthetic methods, as well.

Recombinant expression systems) refers to expression systems or portions thereof or polynucleotides of the invention introduced or transformed into a host cell or host cell lysate for the production of the polynucleotides and polypeptides of the invention.

Variant(s), as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant can or can not alter the amino acid sequence of a polypeptide encoded by the reference polynucleotide. Nucleotide changes can result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide can differ in amino acid sequence by one or more substitutions, additions, deletions in any combination. A substituted or inserted amino acid residue can or can not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gin; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide can be a naturally occurring such as an allelic variant, or it can be a variant that is not known to occur naturally. Non-naturally occurring variants of polynucleotides and polypeptides can be made by mutagenesis techniques, by direct synthesis, and by other recombinant methods known to skilled artisans.

Other Aspects

The nucleic acid sequences described herein, and consequently the protein sequences derived therefrom, have been carefully sequenced. However, those of ordinary skill will recognize that nucleic acid sequencing technology can be susceptible to inadvertent error. Those of ordinary skill in the relevant arts are capable of validating or correcting these sequences based on the ample description herein of methods of isolating the nucleic acid sequences in question, and such modifications that are made readily available by the present disclosure are encompassed by the present invention. Furthermore, those sequences reported herein are believed to define functional biological macromolecules within the invention whether or not later clarifying studies identify sequencing errors. Moreover, please note that sequences recited in the Sequence Listing as "DNA" represent an exemplification of the invention, since those of ordinary skill will recognize that such sequences can be usefully employed in polynucleotides in general, including ribopolynucleotides.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLES

The examples below are carried out using standard techniques, that are well known and routine to those of skill in the art, except where otherwise described in detail. The examples are illustrative, but do not limit the invention.

Example 1

Sequence of E. coli Acyl Carrier Protein

The sequence of the E. coli apo-ACP we have cloned and overexpressed is the same one originally described by Rawlings and Cronan (Rawlings, M. and Cronan, J. E., Jr. [1992] J. Biol. Chem. 267,5751–5754). The nucleotide and protein sequences are given below:
Nucleotide sequence of E. coli ACP [SEQ ID NO: 33]:
ATGAGCACTATCGAAGAACGCGTTAA-
GAAAATTATCGGCGAACAGCTGGGCGTTAA GCAG-
GAAGAAGTTACCAACAATGCT-
TCTTTCGTTGAAGACCTGGGCGCGGATTCTCT
TGACACCGTTGAGCTGGTAATGGCTCTG-
GAGAAGAGTTTGATACTGAGATTCCGGAC GAA-
GAAGCTGAGAAAATCACCACCGTTCAG-
GCTGCCATTGATTACATCAACGGCCA CCAGGCG
Protein sequence of E. coli ACP [SEQ ID NO: 34]:
MSTIEERVKKIIGEQLGVKQEEVTNNASFVEDLGAD
LDTVELVMALEEEFDTEIPDEEAEKITTVQAAIDYI
NGHQA
Position for the attachment of the phosphopantetheinyl prosthetic group is highlighted in red.

Example 2

Structures of the Various Acyl-ACP's

The structures of the acyl-ACP's have been summarized in a review article: Prescott, D. J. and Vagelos, P. R. (1972) Adv. Enzymol. 36, 269–311. Briefly, all of the acyl-ACP's are variants of holo-ACP in which the phosphopantetheinyl group is conjugated with various acyl groups as defined below. Holo-ACP itself is a derivative of apo-ACP, the starting material in our syntheses, where $Ser_{37}$ (highlighted above) is conjugated to the phosphopantetheinyl moiety of coenzyme A. The structure of holo-ACP is also shown in Table 1.

Example 3

Expression and Purification of E. coli apo-ACP

E. coli apo-ACP was over expressed in an E. coli expression system. The cell pellet was suspended in 10 volumes of 20 mM Tris.HCl, 0.1 M NaCl, 5 mM $MgCl_2$, 2 mM $MnCl_2$, pH 7.0. After homogenizing with Avistan at 15,000 psi, the pH and temperature were raised to 85 and 35° C., respectively. These conditions were maintained for 2 hours by intermittently adjusting the pH with NaOH. Following this, the pH was adjusted to 7.0 with HCl, and an equal volume of isopropyl alcohol was added with stirring. Stirring was continued at 4° C. overnight. After centrifugation at 15,000 g, the supernatant was filtered through Whatman 1 paper followed by a 1-$\mu$ Millipore membrane. The clear filtrate was loaded at 20 mL/minute onto Q-Sepharose FF column (5×16 cm) pre-equilibrated with 20 mM Bis-Tris, pH 6.8. The column was washed sequentially with following washes: one column volume of 20 mM Bis-Tris, pH 6.8; two column volumes of 0.1 M NaCl in 20 mM Bis-Tris, pH 6.8; two column volumes of 0.2 M NaCl in 20 mM Bis-Tris, pH 6.8. The apo-ACP was eluted with the following gradient: Buffer A: 20 mM Bis-Tris, pH 6.8; Buffer B: 1 M NaCl in 20 mM Bis-Tris, pH 6.8; at a flow rate of 20 mL/minute, at:

| Time: | 0 | 15 | 110 | 111 | 126 | 127 | 130 |
|---|---|---|---|---|---|---|---|
| % B: | 20 | 20 | 60 | 100 | 100 | 20 | 20 |

Fractions were collected at 2-minute intervals and were monitored by mass spectrometry for identity and purity. The appropriate fractions were pooled and concentrated using a YM-3 membrane.

Example 4

FPLC Separation of ACP Derivatives

Buffer A was comprised of 20 mM Tris.HCl, pH 7.4; Buffer B was comprised of 20 mM Tris-HCl, pH 7.4, 1M NaCl. All chromatography was run at a constant flow rate of 1 mL/minute. Samples were loaded onto a Phamacia Mono Q (5/5) column equilibrated with Buffer A. The column was washed for 5 minutes with 10% Buffer B, and the ACP's or acyl-ACP's were eluted during an 0.5%/minute linear gradient to 50% Buffer B. ACP standards eluted as follows: apo-ACP (34% B), holo-ACP (37% B), malonyl-ACP (39% B). The column was washed with 5 mL 100% Buffer B prior to equilibration with Buffer A.

Example 5

Synthesis of Holo-ACP

Holo-ACP was synthesized via the ACP synthase reaction containing 0.1 M NaHEPES, pH 7.5, 0.1 mM apo-ACP, 0.15 mM CoA, 1 mM DTT, 10 mM $MgCl_2$, 60 $\mu$g/mL ACPS (S.

pneumoniae or E. coli). Holo-ACP synthesis was confirmed by FPLC and functionally as a substrate for the FabD reaction either by monitoring the incorporation of [$^{14}$C] malonyl-CoA into malonyl-ACP or via the FabD:FabH coupled enzyme assay by monitoring the incorporation of [$^3$H]acetyl-CoA into acetoacetyl-ACP.

Example 6

Synthesis of Acetyl-ACP

Acetyl-ACP was synthesized via the ACP synthase reaction which contained 0.1 M NaHEPES, pH 7.5, 10 mM MgCl$_2$, 0.2 mM acetyl-CoA, 0.1 mM apo-ACP, and 60 μg/mL E. coli or S. pneumoniase ACP synthase. Reaction volumes ranged up to 100 mL. Approximately 95–100% conversion of apo-ACP to acetyl-ACP was achieved within a 1-hour incubation at 33° C. as demonstrated by FPLC, which showed the disappearance of the apo-ACP substrate and emergence of a new product peak. Following purification by FPLC as described above, acetyl-ACP was quantitated by measuring its absorbance at 280 nm. Although acetyl-ACP is not a currently recognized intermediate of fatty acid biosynthesis, it was found to be an inhibitor of FabH through the formation of dead end inhibition complexes with enzyme.

Example 7

Synthesis of Malonyl-ACP via FabD (Acyl-CoA:ACP(holo) Transacylase)

In order to achieve conversion of 75% of the reaction malonyl-CoA to malonyl-ACP via FabD transacylase activity within 30 minutes, 33° C., reaction conditions required 0.1M Na phosphate, pH 7.0, 1 mM TCEP, malonyl-CoA:holo-ACP (50:1; respectively), and 250 nM FabD. This reaction was placed over an Ni-NTA agarose spin column (Qiagen) to remove the His-tagged FabD. The ACP's were separated from the reducing agent through a PD-10 column equilibrated with 100 mM Na phosphate, pH 7.0, the protein from the column effluent was place over a 1-mL spin-column of activated thiol-Sepharose 4B (Pharmacia) equilibrated in 100 mM Na phosphate, pH 7.0 to remove contaminating holo-ACP and CoA. Malonyl-ACP was concentrated via centrifugation in an Amicon Centriplus3 to approximately 3–5 mg/mL and was quantitated using the FabH reaction (see below).

Example 8

Synthesis of Malonyl-ACP via ACP Synthase (*Escherichia coli*)

Reaction mixtures contained 0.1 M NaHEPES, pH 7.5, 10 nM MgCl$_2$, 0.5 mM malonyl-CoA, 0.3 mM apo-ACP, and 40–60 μg/mL E. coli ACP synthase. The progress of the reaction was monitored by FPLC, and approximately 95–100% conversion of the apo-ACP to malonyl-ACP was achieved within a 2-hour reaction at 33° C.

Example 9

Synthesis of Acetoacetyl-ACP

E. coli apo-ACP (4.1 g), E. coli ACP synthase (40 mg) and buffer composed of 20 mM Bis-Tris, pH 6.8, 63 mM NaCl and 13 mM MgCl$_2$ (total volume 240 mL) were combined in a stirred reaction vessel and incubated at 22° C. Acetoacetyl-CoA (15 mM in 20 mM Bis-Tris, pH 6.8) was added incrementally in 8-mL (125-mg) aliquots over a 1-hour period until a total of 1 g had been added. Incubation was continued while maintaining the pH at 6.8 by the addition of 6 N HCl. The formation of acetoacetyl-ACP was monitored by mass spectral analysis, which showed that the reaction was complete at 2.75 hours. The reaction mixture was adjusted to pH 6.5 by the addition of 6 N HCl and immediately purified by Q-Sepharose FF chromatography as described above for apo-ACP.

Example 10

Synthesis of D-3-Hydroxybutyryl-ACP

This reagent was synthesized from malonyl-ACP in a coupled enzyme system consisting of 20 mM Bis-Tris, pH 6.8, 50 mM NaCl, 2 mM DTT, 100 mg (0.5 mM, malonyl-ACP, 1.5 mM acetyl-CoA, 1 mM NADPH, 70 nM S. pneumoniae FabH and 300 nM S. pneumoniae FabG in a total volume of approximately 25 mL. The reaction was initiated by the addition of the FabH, and continued for 4 hours at 22° C. while maintaining the pH at 6.8 by the addition of 6 N HCl. After 4 hours, the pH of the reaction was lowered to 6.5 with 6 N HCl, and the product was purified as described above for apo-ACP. The concentration of the D3-hydroxybutyryl-ACP was determined by amino acid analysis and in a functional assay consisting of FabZ coupled through FabI.

Example 11

Synthesis of Crotonoyl-ACP

To a reaction vessel containing 500 mg (58 μmol) of E. coli apo-ACP in 20 mM Bis-Tris, pH 6.8, 5 MM MgCl$_2$, was added 76 mg (81 μmoles) of crotonoyl-CoA and 5 mg of S. pneumoniae ACP synthase. The final volume and pH were adjusted to 100 mL and 6.8, respectively. The pH of the reaction was maintained at 6.8 with NaOH and monitored for completion by mass spectrometry. Conversion was complete within 150 minutes with no detectable by-products. The reaction mixture was loaded at 10 mL/minute onto Q-Sepharose FF column (5×16 cm) pre-equilibrated with 20 mM Bis-Tris, pH 6.8. After washing with one column volume of the equilibration buffer, elution of the crotonoyl-ACP was carried out using the same protocol described for apo-ACP.

Example 12

Synthesis of Butyryl-ACP

Butyryl-ACP was synthesized in reaction mixtures containing 0.1 M NaHEPES, pH 7.5, 10 mM MgCl$_2$, 0.2 mM butyryl-CoA, 0.1 mM apo-ACP, and 20 μg/mL E. coli ACP synthase in total volumes up to 50 mL. Approximately 95–100% conversion of apo-ACP to butyryl-ACP was achieved within 1 hour at 33° C. as demonstrated by FPLC, which showed the disappearance of the apo-ACP substrate and emergence of a new product peak. Following purification by FPLC as described above, butyryl-ACP was quantitated by either measuring its absorbance at 280 nm or in a functional assay utilizing malonyl-ACP and a FabF/FabG coupled, spectrophotometric assay measuring the disappearance of NADPH at 340 nm.

Example 13

FabD Assay

Filtration assay:

[$^{14}$C]Malonyl-ACP formation was specifically measured using [$^{14}$C]malonyl-CoA and holo-ACP. The substrate [$^{14}$C] malonyl A is soluble in 10% TCA while the resulting [$^{14}$C]malonyl-ACP is not. Final reaction conditions typically were 100 mM NaPO$_4$, pH 7.0, 1 mM DTT, 50 µM malonyl-CoA, 8 µM [$^{14}$C]malonyl-CoA (specific activity 56 mCi/mmol), and 25 µM E. coli holo-ACP. The enzyme (S. aureus FabD) was added last to start the reaction which was incubated at 37° C. Ten percent TCA was added to stop the reaction and then it was incubated 20 minutes at room temperature. Stopped reactions were filtered and washed 2 times with 10% TCA on Wallac GF/A filtermats using a TomTec harvester. The filtermats were then dried completely at 60° C. and the radioactivity quantified using Wallac Betaplate scintillation cocktail and a Wallac Microbeta 1450 liquid scintillation counter.

Coupled assay:

A product of the malonyl-CoA:ACP transacylase reaction is free coenzyme A. This fact was exploited by coupling the FabD reaction with an excess of β-ketoglutarate dehydrogenase (Sigma). Reaction mixtures typically contained 100 mM NAPO$_4$, pH 7.0, 1 mM DTT, 0.5 M NAD$^+$, 1 mM β-ketoglutaric acid, 0.5 mU/µl β-ketoglutarate dehydrogenase, 50 µM malonyl-CoA, 25 µM E. coli holo-ACP and 1 nM S. aureus FabD. NAD$^+$ reduction was followed spectroscopically at 340 nm.

Example 14

FabH Assay

The assay followed the incorporation of [$^3$H]acetyl-CoA into the TCA-precipitable [$^3$H]acetoacetyl-ACP. In general, assay mixtures contained either fixed (50 µM [$^3$H-]acetyl-CoA and 20 µM malonyl-ACP) or variable concentrations of substrate and were initiated by the addition of FabH. Incubations were carried out in temperature equilibrated (33° C.) reaction microcentrifuge tubes or Falcon 3077 96-well reaction plates, and incubated for the stated amount of time. Reactions were terminated either by adding sample aliquots from reaction tubes into 3 mL 10% TCA with the addition of 0.2 mg BSA, or by adding 0.15 mL 10% TCA and 0.1 mg BSA directly into the reaction plate. Quenched reaction plates were chilled for 20 minutes prior to filtration. Precipitated proteins were recovered from tubes by filtration through Whatman GF/C filter discs with three rinses of 10% TCA, and a final rinse of with 3 mL 1% TCA The filters were dried and counted in 8 mL Beckman ReadySafe and counted in a Beckman LS6500. Precipitated proteins in reaction plates were recovered by filtration through Packard GF/C Unifilters with a Packard Filtermate with three rinses of the reaction plate with 10% TCA and a final rinse with 1% TCA. Plates were dried, sealed and counted with 30 µL Microscint 0 per well in a Packard TopCount scintillation counter.

Example 15

FabH Coupled Assay

The FabH/FabG coupled assay was done in Costar 384-well plates. A reaction mixture consisting of malonyl-ACP (15 µM), acetyl-CoA (20 µM), NADPH (100 µM) and S. pneumoniae FabG (0.15 µM) was prepared in 100 mM NaPO$_4$, pH 7.0 containing 1 mM TCEP. To the plate was added 1 µL of compound in DMSO solution followed by the reaction mixture (44 µL). The plate containing the reaction mixture and the compound was incubated at 33° C. for 5 minutes while H. influenzae FabH was incubated separately at the same temperature. The reaction was started by adding 5 µL of FabH (0.008 µM final concentration) to the reaction wells, mixing and reading the plate at 340 nm in Spectromax Plus 384 plate reader set at 33° C. Data was collected over 15 minutes.

Example 16

FabG Screening Assay

The FabG assay was run in clear 384-well (Falcon 3902) plates in a total volume of 50 µL. Reaction mixtures contained 100 mM NaHEPES, pH 7.5, 50 µM NADPH, 25 µM acetoacetyl-ACP, and 80 nM S. pneumoniae FabG The NADPH was preincubated with the FabG for 15 minutes prior to their addition to the assay plate in order to generate and stabilize the active form of the enzyme. After initiation, incubations were carried out for 5 minutes at 30° C. while monitoring the decrease in absorbance at 340 nm using a Tecan Spectroflour PLUS™ plate reader.

Example 17

FabG Screening Data

The following is an example of FabG validation metrics was used in this Example. For control wells, an average rate (O.D.(A340/minute) of 0.0032 was used, with a standard deviation of about 0.00003. Blank wells were run at an average rate (O.D.(A340/minute) of 0.00007 with a standard deviation of about 0.00008. The AVR was 0.406. The signal:background ratio was 45:1, at a CV of 0.10 (10%).

Example 18

FabZ/I Coupled Assay

The fabZ/I coupled assay uses S. aureus FabZ (stock conc. 27.5 µM) and E. coli fabI (stock conc. 872 µM). The assay was performed in 384 well plates using Tecan Spectrofluore to measure the absorbance using a 340 nm filter. The final volume of the assay was 50 µl and the reagents were prepared 5× concentrated so that 10 µl of each reagent was added to the wells. To the wells was added buffer (100 mM HEPES, pH 7.5), NADH (100 uM), fabI (200 nM, diluted in 20% glycerol) and fabZ (9.2 nM). The plate was incubated in a heating block at 30° C. for 5–10 minutes. The substrate 3-OH-butyryl-ACP was diluted in 20 mM bis-Tris buffer, pH 6.5 and incubated at 30° C. as well. The reaction was started by adding 3-OH-butyryl-ACP to the reaction wells, mixing and reading the plate at 340 nm. The final concentration of HEPES was 80 mM and bis-Tris was 4 mM. To measure the background oxidation of NADH, blanks were prepared using 40 µl buffer and NADH (100 µM).

Example 19

FabI Screening Assay

Assays were carried out in half-area, 96-&well microtiter plates Compounds were evaluated in 150-µL assay mixtures containing 100 mM NaADA, pH 6.5 (ADA=N-[2-acetamido]-2-iminodiacetic acid), 4% glycerol, 25 µM crotonoyl-ACP, 50 µM NADPH, and an appropriate dilution of S. aureus Fab I (approximately 20 nM). Inhibitors are typically varied over the range of 0.01–10 μM. The consumption of NADPH was monitored for 20 minutes at 30° C. by following the change in absorbance at 340 nm. Initial velocities were estimated from a linear fit of the progress curves. $IC_{50}$'s were estimated from a fit of the initial velocities to a standard, 4-parameter model (Equation 1) and were typically reported as the mean βS.D. of duplicate determinations. The apparent $K_1$ was calculated from Equation 2 assuming the inhibition was competitive with crotonoyl-ACP.

$$v = \frac{\text{Range}}{\left(1 + \frac{[I]}{IC_{50}}\right)^s} + \text{Background} \quad (1)$$

$$Ki_{app} = \frac{IC_{50}}{1 + \frac{[S]}{K_S}} \quad (2)$$

Example 20

FabF Screening Assay

Assays were carried out in 96-well half-area plates in a total volume of 50 μL in a FabG coupled system III containing 100 nM $NaPO_4$, pH 7.0, 100 μM NADPH, 10 μM malonyl-ACP, 10 μM butyryl-ACP, and 600 nM *S. pneumoniae* FabG. Compounds were added to the above mixture at a final concentration of 2 and 20 μM and mixed for 30 seconds on a plate shaker prior to running the assay. The reaction was started by the addition of 100 nM (final concentration) *Streptococcus pneumoniae* FabF. Incubations were carried out for 15 minutes at 31° C., during which time the consumption of NADPH was monitored at 340 nm in a Spectromax 384 absorbance plate reader. Initial velocities were determined from the slope of the progress curves over the first 100–200 seconds, and the % inhibition was estimated from a comparison of the background-corrected, inhibited rates with the corrected, control (non-inhibited) rates.

Example 21

Cloning of *Streptococcus pneamoniae* FabK

The *S. pnewnoniae* fabK, enoyl-ACP reductase gene was PCR amplified from *S .pneumoniae* strain 0100993. The forward and reverse primer sequences were 5' AGGTTGGAGGCCATATGAAAACGCGTATT3' [SEQ ID NO:35] and 5' GGCAGATCCTTAGTCATTTCTTACAACTC3' [SEQ ID NO: 36], respectively. An NdeI site was integrated into the forward primer and a BamHI site into the reverse primer for cloning into pET24b(+). The PCR product was digested with the restriction endonucleases NdeI and BamHI and then ligated into pET24b(+), (also digested with NdeI and BamHI). The resulting plasmid was transformed into subcloning efficiency DH5-alpha cells. The sequence of the pET24bSpfabK expression construct was confirmed by DNA sequencing and the plasmid was transformed into electrocompetent BL21 (DE3) cells harboring the tRNA vector pRR692.

Intact FabK is expressed as 25% total cell protein of which 80% is soluble when induced with 0.1 mM IPTG at 37° C. for three hours.

Example 22

Purification of *S. pneamoniae* FabK

One liter of cells containing the FabK expression construct were grown to an OD600 of 0.6. Expression was induced with 0.1 mM IPTG and the cells were grown for a further 3 hours and then harvested. The cell pellet was resuspended in 10 ml 50 mM Tris pH7.5, 1 mM PMSF, 1 mM Benzamidine, 1 mM DTT (buffer A) and lysed by sonication. Cell debris was removed by centrifugation. The supernatant was loaded onto a Hi-load Q (16/10) column Pharmacia) equilibrated in buffer A. Protein was eluted over a 200 ml gradient of 0–100% buffer B, where buffer B is buffer A+1 M KCl. Fractions containing FabK were identified by their absorbance at A460 and by their FabK activity and pooled.

1.5 M ammonium sulphate was added to the pooled fractions and these were then loaded onto a Hi-load Phenyl sepharose (16/10) column (Pharmacia) equilibrated in 50 mM Tris pH 7.5, 1 mM PMSF, 1 mM Benzamidine, 1 mM DTT, 1.5 M amionium sulphate. Proteins were eluted with a gradient of ammonium sulphate (1.5 to 0 M) over 200 ml. Fractions containing FabK were identified as above and pooled. The pooled fractions were buffer exchanged into 100 mM Tris, pH 7.5, 2 mM DTT and glycerol was then added to 50%. The protein was stored at −20° C. It is preferred that the enzyme be stored with $NH_4Cl$, which has been found to stabilize the enzyme.

The amino acid sequence of a FabK of the invention:
MKTRITELLKIDYPIFQGGMAWVADGD-
LAGAVSKAGGLGIIGGGNAPKEVVKAN-
NIDKIKSLTDKPFGV NIMLLSPFVEDIVDLVIEE-
GVKVVTTGAGNPSKYMERFHEAGIIVIPVVPSVALA
KRMEKIGADAVIA XMEAGGHIGKLTTMTLVRQ-
VATAISIPVIAAGGIADGEGAAAGFML-
GAEAVQVGTRFVVAKESNAHP NYEKILKARDIDT-
TISQHFGHAVRAIKNQLTRDFELAEKDAFQEDPDLEI
FEQMGAGALAKAVVH GDVDGGSVMAGQIAGLVS-
KEETAEEILKDLYYGAAKKIQEEASRWAGVVRND
[SEQ ID NO: 37]

Example 23

FabK Characterization

The identity of the protein was confirmed by N-terminal sequencing and MALDI mass spectrometry. The optical spectrum of the protein was characteristic of flavoproteins, showing an absorbance in the 450 nm region. The FAD cofactor was removed by denaturation of the protein and quantified. The ratio of FAD:protein was shown to be approximately 1:1.

Example 24

Assaying the Aactivity of FabK

FabK catalyses the reduction of enoyl-ACPs with the concommitant oxidation of NADH. Crotonoyl-ACP can be prepared as described below. The reduction of crotonoyl-ACP to butyryl-ACP can be monitored by following the change in absorbance at 340 nm as NADH is oxidised.

Assays were carried out in Costar 3696 half-area plates in a fmal assay volume of 150 μl on a Spectramax platereader. Substrates, NADH and crotonoyl ACP, were incubated with FabK enzyme in 100 nM N-[2-acetamido]-2 iminodiacetic acid (ADA), pH 6.5, 100 mM $NH_4Cl$, 4% glycerol at 30° C. and the reaction monitored at 340 nm. This assaying can also be performed using crotonyl CoA, NADPH or an NADH analogue as a substrate.

Example 25

Activation by Monovalent Cations

FabK was found to be activated by monovalent cations. The greatest activation was found to be with $NH_4^+$ at 100

Example 26

Compound Screening

Using the above assay, compounds can be tested for inhibition of FabK. 30 μl of a bioactive agents is added to a well of the plate. 30 μl of a 250 μM stock of NADH is then added to the well. 60 μl of a 67.5 μM stock of Crotonoyl ACP is added to the well. The plate is incubated at 30° C. for 5 minutes. 30 μl of a 6.25 nM stock of enzyme is then added to the well (also preincubated at 30° C.) to initiate the reaction. The plate is then monitored at A340 nm for 30 minutes at 30° C. Positive controls are reactions without compound. Negative controls are reactions without enzyme and without compound. Final concentrations in the assay mixture are 25 μM crotonoyl ACP, 50 μM NADH, 1.25 nM enzyme.

Example 27

Synthesis of Crotonoyl-ACP

Crotonoyl-ACP was synthesised using *S. pneumoniae* ACP synthase to catalyse the addition of a crotonoyl group from crotonoyl CoA to *E. coli* apo-acyl carrier protein (ACP).

To a reaction vessel containing 500 mg (58 μmol) of *E. coli* apo-ACP in 20 mM Bis-Tris, pH 6.8, 5 mM $MgCl_2$, was added 76 mg (81 μmoles) of crotonoyl-CoA and 5 mg of *S. pneumoniae* ACP synthase. The final volume and pH were adjusted to 100 mL and 6.8, respectively. The pH of the reaction was maintained at 6.8 with NaOH and monitored for completion by mass spectrometry. Conversion was complete within 150 minutes with no detectable by-products. The reaction mixture was loaded at 10 mL/minute onto a Q-Sepharose FF column (5×16 cm) pre-equilibrated with 20 mM Bis-Tris, pH 6.8. Crotonoyl-ACP was eluted over 2200 ml using a 0.2M–6M NaCl gradient at a flow rate of 20 ml/minute. Fractions were monitored by mass spectrometry for identity and purity. The appropriate fractions were pooled and concentrated using a YM-3 membrane.

Example 28

FabI Assay Method

FabI enzyme, and methods of making and using it, is disclosed in patent applications numbered PCT/US00/12104 and EP1997000306506.

FabI catalyses the reduction of enoyl-ACPs with the concommitant oxidation of NAD(P)H. Crotonoyl-ACP can be prepared as described in patent applications numbered PCT/US00/12104 and EP1997000306506. The reduction of enoyl-ACPs can be monitored by following the change in absorbance at 340 nm as NADH is oxidised. Enoyl ACPs (eg., crotonoyl-ACP) can be replaced by enoyl-CoAs (e.g., crotonoyl-CoA)

Assays were carried out in Costar 3696 half-area plates in a final assay volume of 150 μl on a Spectramax platereader. Substrates, NADH and crotonoyl ACP, were incubated with FabI enzyme in 100 mM N-[2-acetamido]-2 iminodiacetic acid (ADA), pH 6.5, 4% glycerol at 30° C. and the reaction monitored at 340 nm. This assaying can also be performed using crotonyl CoA, NADPH or an NADH analogue as a substrate, or using a substrate suitable for FabK, such as those described above.

Using the above assay, compounds can be tested for inhibition of FabI. 30 μl of a bioactive agents is added to a well of the plate. 30 μl of a 250 uM stock of NADH is then added to the well. 60 μl of a 67.5 uM stock of Crotonoyl ACP is added to the well. The plate is incubated at 30° C. for 5 minutes. 30 μl of a 6.25 nM stock of enzyme is then added to the well (also preincubated at 30° C.) to initiate the reaction. The plate is then monitored at A340 nm for 30 minutes at 30° C. Positive controls are reactions without compound. Negative controls are reactions without enzyme and without compound. Final concentrations in the assay mixture are 25 μM crotonoyl ACP and 50 μM NADH.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

---

What is claimed is:

1. A high throughput screening method for biological agents affecting fatty acid biosynthesis, wherein the method comprises:
   (A) providing a reaction mixture comprising
      (1) (a) an acyl carrier moiety or (b) enzymes and precursors sufficient to generate the acyl carrier moiety;
      (2) a bacterial enzymatic pathway comprising at least two consecutively acting enzymes selected from the group consisting of:
         (a) malonyl-CoA:ACP transacylase,
         (b) β-ketoacyl-ACP synthase III,
         (c) NADPH-dependent β-ketoacyl-ACP reductase,
         (d) β-hydroxyacyl-ACP dehydrase, and
         (e) enoyl-ACP reductase; and
      (3) first substrates and cofactors required for activity of the enzymes;
   (B) contacting the reaction mixture with a bioactive agent;
   (C) conducting a high throughput measurement of the activity of the enzymatic pathway; and
   (D) determining if the contacting alters the activity of the enzymatic pathway.

2. The method of claim 1, wherein the bacterial enzymatic pathway comprises at least three consecutively acting enzymes selected from:
   (a) malonyl-CoA:ACP transacylase,
   (b) β-ketoacyl-ACP synthase III,
   (c) NADPH-dependent β-ketoacyl-ACP reductase,
   (d) β-hydroxyacyl-ACP dehydrase, and
   (e) enoyl-ACP reductase.

3. The method of claim 1, wherein the bacterial enzymatic pathway comprises at least four consecutively acting enzymes selected from:
   (a) malonyl-CoA:ACP transacylase,
   (b) β-ketoacyl-ACP synthase III,
   (c) NADPH-dependent β-ketoacyl-ACP reductase,
   (d) β-hydroxyacyl-ACP dehydrase, and
   (e) enoyl-ACP reductase.

4. The method of claim 1, wherein the bacterial enzymatic pathway comprises at least five consecutively acting enzymes selected from:
   (a) malonyl-CoA:ACP transacylase,
   (b) β-ketoacyl-ACP synthase III,
   (c) NADPH-dependent β-ketoacyl-ACP reductase,
   (d) β-hydroxyacyl-ACP dehydrase, and
   (e) enoyl-ACP reductase.

5. The method of claim 1, wherein the high throughput measurement measures the activity of enoyl-ACP reductase.

6. The method of claim 1, wherein the high throughput measurement comprises:
   (1) photometrically measuring consumption of NADH; or
   (2) providing [3H]NADH as a cofactor to the enzymatic pathway and capturing a radioactive product on a support that provides a scintillant.

7. The method of claim 1, further comprising: providing intermediate substrates in a reacting step, wherein the intermediate substrates are not derived from said first substrates and are provided in an amount adapted to maintain such intermediate substrates at a concentration at least approaching the $K_m$ of a respective enzyme that acts on the substrate during an assay timeframe.

8. The method of claim 7, further comprising: selecting at least one of the enzymes from a corresponding enzyme produced by *Staphylococcus aureous, Haemophilus influenzae* or *Streptococcus pneumoniae*.

9. The method of claim 8, further comprising: providing as the enoyl-ACP reductase a NADH-specific enoyl-ACP reductase.

10. The method of claim 9, further comprising: providing to the reacting step NADPH in a constant amount such that the NADH consumption by enoyl-ACP reductase (FabI) can be quantitated accurately and without interference, or an amount effective to reduce NADH consumption by more NADPH-dependent enzymes.

11. The method of claim 10, further comprising: providing to the reacting step an NADPH regenerating enzyme system.

12. The method of claim 8, further comprising: providing as the β-ketoacyl-ACP synthase III a β-ketoacyl-ACP synthase III derived from *E. coli* or *H. influenzae*.

13. The method of claim 1, wherein the malonyl-CoA:ACP transacylase is derived from *Streptococcus* or *Staphylococcus*, the β-ketoacyl-ACP synthase III is derived from *Streptococcus*, *Staphylococcus* or *Escherichia*, the NADPH-dependent β-ketoacyl-ACP reductase is derived from *Streptococcus* or *Staphylococcus*, the β-hydroxyacyl-ACP dehydrase is derived from *Streptococcus* or *Staphylococcus*, and the enoyl-ACP reductase is derived from *Staphylococcus* or *Escherichia*.

14. The method of claim 1, wherein the NADPH-dependent β-ketoacyl-ACP reductase is derived from *Streptococcus*, *Staphylococcus* or *Pseudomonas*.

15. The method of claim 1, further comprising: β-ketoacyl-ACP synthase II as part of the enzymatic pathway.

16. The method of claim 1, further comprising: when a bioactive agent affecting the enzymatic pathway is identified, applying one or more deconvolution assays for determining which enzymes in the enzyme pathway are affected, said deconvolution assays comprising contacting the identified bioactive agent with (i) an enzyme in the enzymatic pathway or (ii) two or more, but less than all, enzymes acting sequentially in the enzymatic pathway.

17. A screening method for biological agents affecting fatty acid biosynthesis:

(A) providing a reaction mixture comprising
  (1) (a) an acyl carrier moiety or (b) enzymes and precursors sufficient to generate the acyl carrier moiety;
  (2) a bacterial enzymatic pathway comprising at least two consecutively acting enzymes selected from:
    (a) malonyl-CoA:ACP transacylase,
    (b) β-ketoacyl-ACP synthase III,
    (c) NADPH-dependent β-ketoacyl-ACP reductase,
    (d) β-hydroxyacyl-ACP dehydrase, and
    (e) enoyl-ACP reductase; and
  (3) first substrates and cofactors required for activity of the enzymes;

(B) contacting the reaction mixture with a bioactive agent;

(C) conducting a high throughput measurement of the activity of the enzymatic pathway;

and determining if the contacting alters the activity of the enzymatic pathway, wherein at least one of the following applies:
  (1) the enoyl-ACP reductase is a NADH-specific enoyl-ACP reductase; or
  (2) the β-ketoacyl-ACP synthase III is a β-ketoacyl-ACP synthase III derived from *E. coli* or *H. influenzae*; or
  (3) NADPH is provided to the reacting step in a constant amount such that the NADH consumption by enoyl-ACP reductase (FabI) can be quantitated accurately and without interference, or an amount effective to reduce NADH consumption by more NADPH-dependent enzymes; or
  (4) the NADPH-dependent β-ketoacyl-ACP reductase is derived from *Streptococci*, *Staphylococci* or *Pseudomonas*.

* * * * *